(12) United States Patent
Gupta et al.

(10) Patent No.: US 9,107,569 B2
(45) Date of Patent: Aug. 18, 2015

(54) MEDICAL INSTRUMENT FOR EXAMINING THE CERVIX

(75) Inventors: Vipin Gupta, Bangalore (IN); Caifeng Shan, Eindhoven (NL); Pallavi Vajinepalli, Bangalore (IN); Payal Keswarpu, Bangalore (IN); Marinus Bastiaan Van Leeuwen, Eindhoven (NL); Celine Firtion, Surat (IN); Shankar Mosur Venkatesan, Bangalore (IN); Jelte Peter Vink, Waaire (NL)

(73) Assignee: Koninklijke Philips N.V., Eindhoven (NL)

( * ) Notice: Subject to any disclaimer, the term of this patent is extended or adjusted under 35 U.S.C. 154(b) by 61 days.

(21) Appl. No.: 14/004,907

(22) PCT Filed: Mar. 12, 2012

(86) PCT No.: PCT/IB2012/051149
§ 371 (c)(1),
(2), (4) Date: Sep. 13, 2013

(87) PCT Pub. No.: WO2012/123881
PCT Pub. Date: Sep. 20, 2012

(65) Prior Publication Data
US 2014/0005477 A1   Jan. 2, 2014

Related U.S. Application Data

(60) Provisional application No. 61/567,158, filed on Dec. 6, 2011.

(30) Foreign Application Priority Data

Mar. 16, 2011 (EP) ..................................... 11305291

(51) Int. Cl.
*G06K 9/00* (2006.01)
*A61B 1/00* (2006.01)
(Continued)

(52) U.S. Cl.
CPC ............. *A61B 1/00009* (2013.01); *A61B 1/303* (2013.01); *G06T 7/0016* (2013.01);
(Continued)

(58) Field of Classification Search
CPC ...................................................... A61B 5/4331
See application file for complete search history.

(56) References Cited

U.S. PATENT DOCUMENTS

2002/0065468 A1   5/2002   Utzinger et al.
2003/0144585 A1   7/2003   Kaufman et al.
(Continued)

OTHER PUBLICATIONS

Durant-Whyte, H., et al.; Simultaneous Localisation and Mapping (SLAM): Part I The Essential Algorithms; 2006; Robotics and Automation Magazine; 13(2)99-110.
(Continued)

*Primary Examiner* — Atiba O Fitzpatrick

(57) ABSTRACT

The invention provides for a medical instrument for examining the cervix comprising an optical examination system, a processor for controlling the medical instrument, and a memory containing machine executable instructions. Execution of the instructions causes the processor to: acquire a cervical image using the optical examination system; calculate a set of interest point locations using a digital filter; calculate a filtered set of interest point locations using the set of interest point locations and a morphological filter; calculate a reduced set of interest points locations using the filtered set of interest point locations and a neighborhood based filter; calculate a classified set of interest point locations reduced set of interest points and a trained classification module; calculate a set of punctation locations using the classified set of interest point locations and a second neighborhood based filter; and calculate punctation mark regions using the punctation point locations.

15 Claims, 45 Drawing Sheets

(51) Int. Cl.
*A61B 1/303* (2006.01)
*G06T 7/00* (2006.01)

(52) U.S. Cl.
CPC .......... *G06T2207/10016* (2013.01); *G06T 2207/10021* (2013.01); *G06T 2207/10056* (2013.01); *G06T 2207/20036* (2013.01); *G06T 2207/20081* (2013.01); *G06T 2207/30004* (2013.01); *G06T 2207/30096* (2013.01)

(56) References Cited

U.S. PATENT DOCUMENTS

| | | |
|---|---|---|
| 2009/0034824 A1 | 2/2009 | Li et al. |
| 2009/0046905 A1 | 2/2009 | Lange et al. |
| 2009/0076368 A1 | 3/2009 | Balas |
| 2010/0092064 A1 | 4/2010 | Li |

OTHER PUBLICATIONS

Garcia-Arteaga, J. D., et al.; Automatic Landmark Detection for Cervical Image Registration Validation; 2009; IEEE Trans. Medical Imaging; 28(3)454-468.

Harris, C., et al.; A Combined Corner and Edge Detector; 1998; Alvey Vision Conf.; pp. 147-151.

IARC Screening Group; Appendix 5: The modified Reid colposcopic index (RCI) http://screening.iarc.fr/colpoappendix5.php downloaded Sep. 11, 2013.

Lange, H.; Automatic glare removal in reflectance imagery of the uterine cervix; 2005; Proc SPIE; 5747; pp. 2183-2192.

Li, W., et al.; Automated image analysis of uterine cervical images; 2007; Proc. SPIE; 6514, Medical Imaging: Computer-Aided Diagnosis; p. 65142.

Li, W., et al.; Detection and Characterization of Abnormal Vascular Patterns in Automated Cervical Image Analysis; 2006; LNCS; 4292:627.

Lowe, D. G.; Distinctive Image Features from Scale-Invariant Keypoints; 2004; International Journal of Computer Vision; 60(2)91-110.

Massad, L. S., et al.; Interobserver Agreement in the Assessment of Components of Colposcopic Grading; 2008; 111(6)1279-1284.

Park, S. Y., et al.; Domain-Specific Image Analysis for Cervical Neoplasia Detection Based on Conditional Random Fields; 2011; IEEE Trans. on Medical Imaging; 30(3)867-878.

Wu, T., et al.; Clinical study of quantitative diagnosis of early cervical cancer based on the classification of acetowhitening kinetics; 2010; Journal of Biomedical Optics; 15(2)26001-1-26001-7.

Yang, S., et al.; A multispectral digital Cervigram analyzer in the wavelet domain for early detection of cervical cancer; 2004; Proc. SPIE 5370: Medical Imaging; Image Processing 1833.

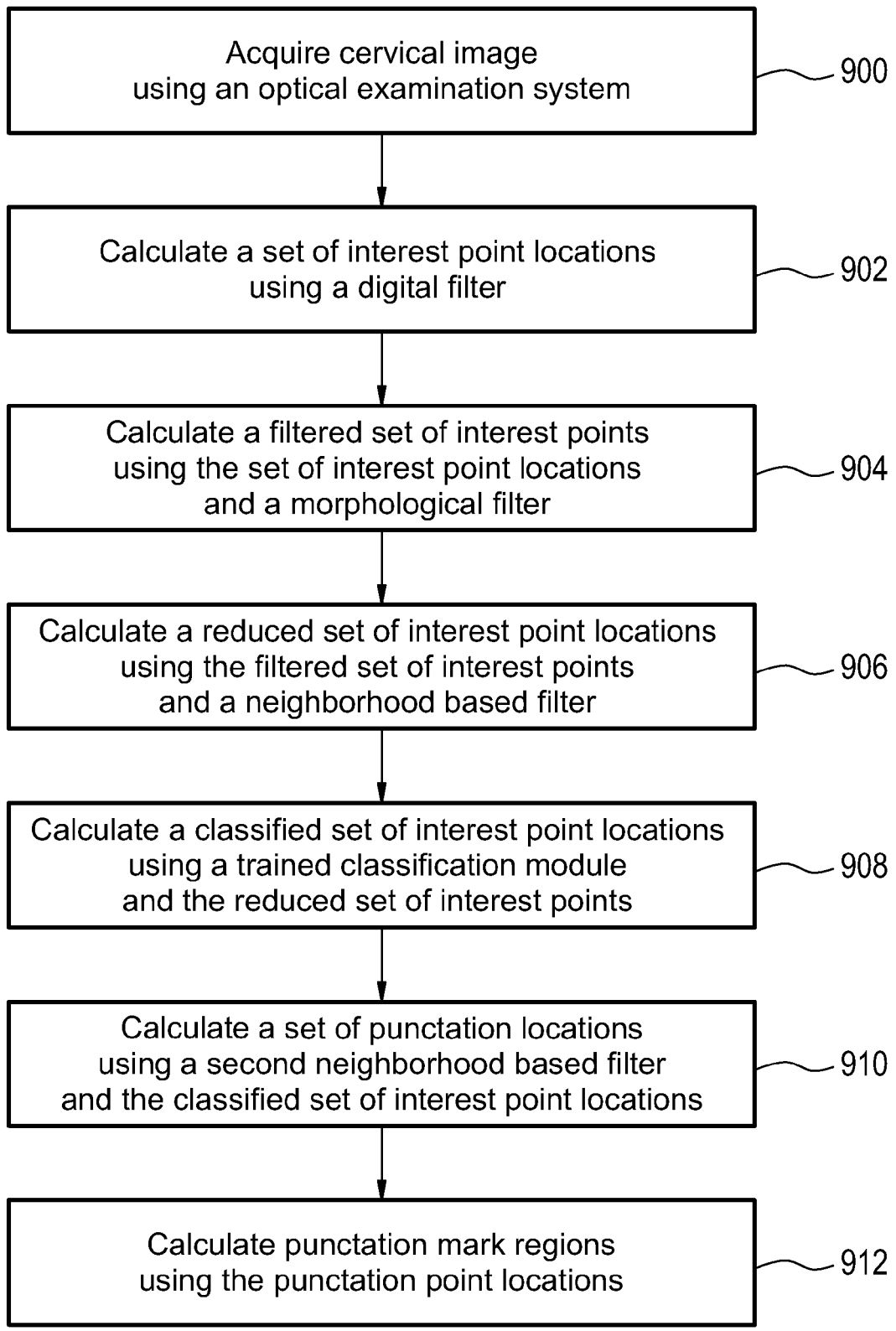

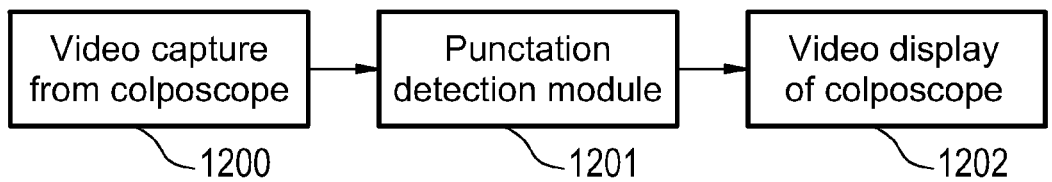
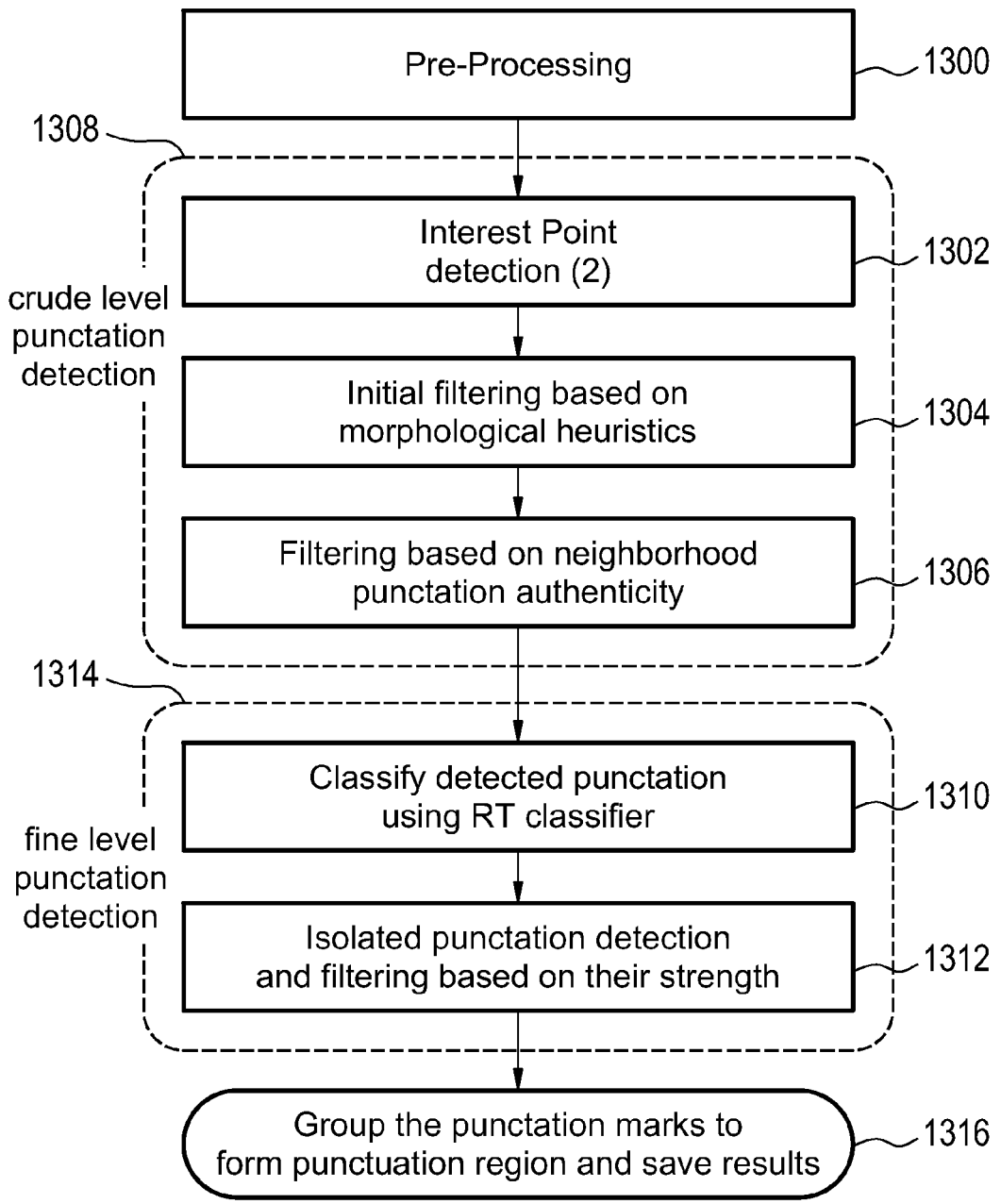

a)

b)

FIG. 20
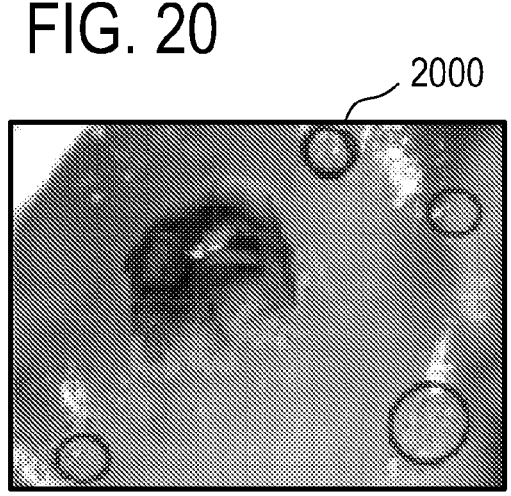
FIG. 21
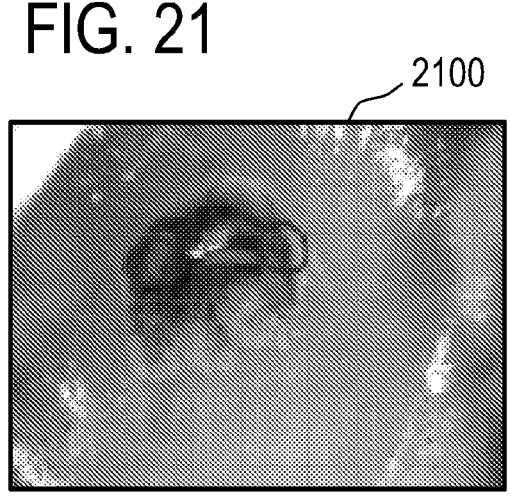
FIG. 22
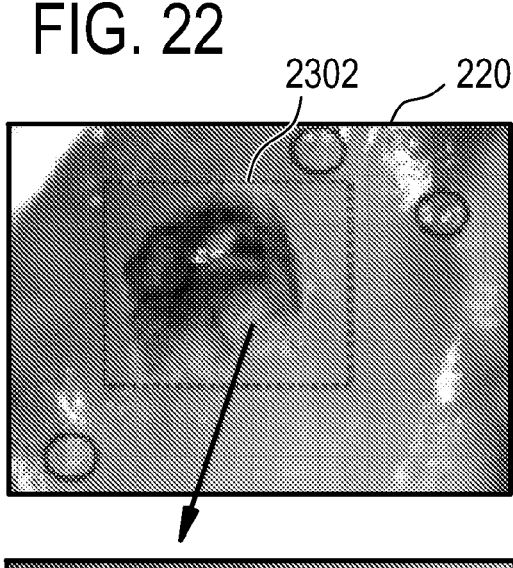
FIG. 23
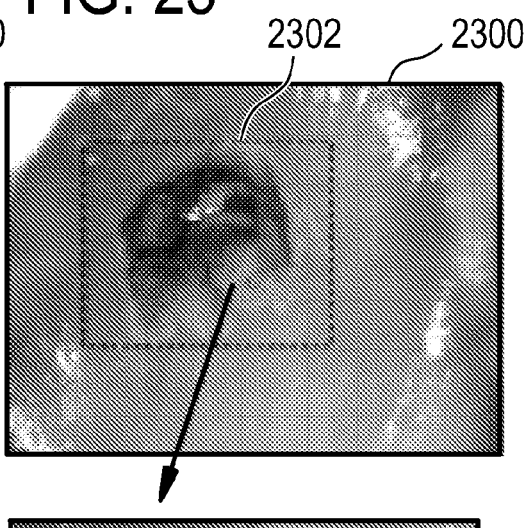
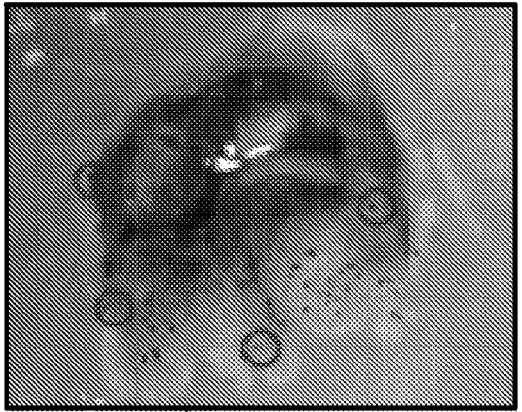
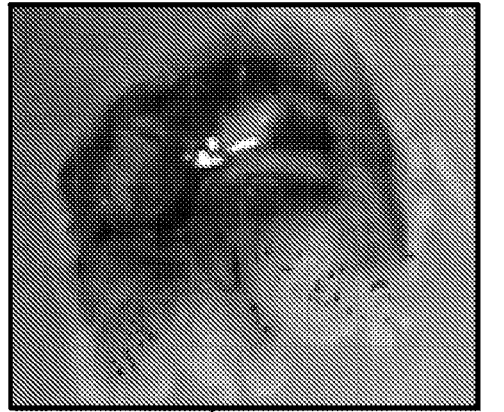

| RCI (overall score) | Histology |
|---|---|
| 0 - 2 | Likely to be CIN 1 |
| 3 - 4 | Overlapping lesion: likely to be CIN 1 or CIN 2 |
| 5 - 8 | Likely to be CIN 2-3 |

6200 — 6202

MEDICAL INSTRUMENT FOR EXAMINING THE CERVIX

CROSS REFERENCE TO RELATED APPLICATIONS

This application is a national filing of PCT application Serial No. PCT/IB2012/051149, filed Mar. 12, 2012, published as WO 2012/123881 A2 on Sep. 20, 2012 which claims the benefit of U.S. provisional application Ser. No. 61/567,158 filed Dec. 6, 2011, and EP provisional application serial no. 11305291.4 filed Mar. 16, 2011, both of which are incorporated herein by reference.

FIELD OF THE INVENTION

The invention relates to the field optical examination of the cervix, particularly to the field of colposcopy.

BACKGROUND OF THE INVENTION

Cancer arising from the cervix is the number one cancer in women in many countries. About 30% of cancers in women are due to cervical cancer with more than 100,000 new cases diagnosed every year, e.g., in India.

After a positive screening test for cervical cancer, colposcopic examination is routinely used as the second diagnostic step by gynecologists for identification of abnormal areas of the cervix. A colposcope is a low-power, stereoscopic, binocular field microscope with a powerful light source used for magnified visual examination of the uterine cervix to help in the diagnosis of cervical cancer.

A routine test for cervical cancer applied worldwide, and in which a colposcope is used, involves the reaction of tissue to the administration of acetic acid and iodine solution to the cervix.

A colposcope is used to identify visible clues suggestive of abnormal tissue. It functions as a lighted binocular microscope to magnify the view of the cervix, vagina, and vulvar surface. Low power (2× to 6×) may be used to obtain a general impression of the surface architecture. Medium (8× to 15×) and high (15× to 25×) powers are utilized to evaluate the vagina and cervix. The higher powers are often necessary to identify certain vascular patterns that may indicate the presence of more advanced precancerous or cancerous lesions. Various light filters are available to highlight different aspects of the surface of the cervix.

Acetic acid (usually 3-5%) is applied to the cervix by means of, e.g., cotton swabs, or spray.

Areas with a high risk of neoplasia, or cancer, will appear as varying degrees of whiteness, because acetowhiteness correlates with higher nuclear density. The term "acetowhiteness" is used in contradistinction to areas of hyperkeratosis or leukoplakia which appear white before the application of acetic acid. The transformation zone is a critical area on the cervix where many precancerous and cancerous lesions most often arise. The ability to see the transformation zone and the entire extent of any visualized lesion determines whether an adequate colposcopic examination is attainable.

Areas of the cervix which turn white after the application of acetic acid or have an abnormal vascular pattern are often considered for biopsy. Iodine solution is applied to the cervix to help highlight areas of abnormality, and distinguish metaplastic regions from suspicious lesions.

After a complete examination, the colposcopist determines the areas with the highest degree of visible abnormality and may obtain biopsies from these areas using a long biopsy instrument. Most doctors and patients consider anesthesia unnecessary. However, some colposcopists now recommend and use a topical anesthetic such as lidocaine or a cervical block to diminish patient discomfort, particularly if many biopsy samples are taken.

Extensive training is needed to correctly interpret a colposcope test according to the above protocol. In emerging markets like India and China lack of trained resources and expertise limit the usage of this effective diagnostic tool. The same situation applies for industrialized countries, where qualified medical personnel are in short supply.

Colposcopy diagnosis requires expertise and involves detection of specific image features for precise diagnosis of uterine cervix diseases. This makes automation in this area challenging. Of the several features considered to make a diagnosis one of the important features is the punctation marks present on the cervix region: they are a marker of abnormal vessels' architecture and their presence is significantly correlated to the existence of pre- and cancerous lesions of the cervix.

SUMMARY OF THE INVENTION

The invention provides for a medical instrument, a computer program product, a method of operating the medical instrument and a method of video registration in the independent claims. Embodiments are given in the dependent claims.

The present invention may provide for a method to identify the punctation marks present in the colposcopy image robustly. Embodiments of the invention may provide for a hierarchical filtration approach followed by a learning based framework to detect different kinds of punctation (fine/coarse/diffused) and segment those areas for diagnostic assistance. Embodiments of the invention may divide the punctation detection into two stages: (1) Crude level punctation detection: It is based on interest point detection followed by several steps of object filtration to remove falsely detected objects. (2) Fine level Punctation detection: A learning based framework is used to classify the crudely detected punctation robustly. The last step is to define regions containing punctation marks. Tests were performed on 35 datasets with varying severity of precancerous lesions and an average accuracy of 98.2% on a test set was achieved.

Current colposcopy examinations are subjective and depend on the knowledge and experience of a gynaecologist for the interpretation. It is thus an object of the present invention to eliminate subjectivity from the process. It is another object of the present invention to increase usability of colposcopy by reducing the learning curve and assisting in diagnosis. It is another object of the present invention to provide better confidence to the user (gynaecologist). It is still another object of the present invention to provide a quantitative measure for the degree of cancer severity.

These objects are achieved by a system or a method according to the present invention.

According to the invention, a system for optical examination of the cervix is provided, said system comprising optical magnification means, illumination means, dispensing means for administration of at least one stimulation and/or contrasting agent, imaging means and image processing means. Said image processing means further comprises key frame extraction means, optionally, glare removal means, object detection means (also called "object detector") and opacity change detection means.

Glare as used herein may refer to specular reflection. As such the glare removal means may be a specular reflection removal means in some embodiments.

In a preferred embodiment, the system further comprises operator interfacing means for data input and data output. Such interfacing means is, for example, a display screen, a keyboard, a mouse, a touch screen, a touchpad, a joystick or likewise.

Preferably, said stimulation and/or contrasting agents are selected from the group consisting of acetic acid and/or iodine solution, preferably Lugol's solution or Schiller's solution. As becomes evident from the specification of the present invention, the skilled person may find alternative stimulating and/or contrasting agents in the respective literature by routine work. Such alternative stimulating and/or contrasting agents are thus comprised by the scope of protection provided by the present invention.

In another preferred embodiment, the imaging means comprises either a digital imaging device, or a non-digital camera and a frame grabber. Said digital imaging device is preferably a digital camera. Said digital or non-digital camera comprises, preferably, a CCD (Charge Coupled Device) or a CMOS (Metal Oxide Semiconductor) camera.

In another preferred embodiment, the optical magnification means is a colposcope. A colposcope may be a low-power, stereoscopic, binocular field microscope with a powerful light source, which is used for magnified visual examination of the uterine cervix to help in the diagnosis of cervical cancer. A colposcope does not need to be stereoscopic.

In another preferred embodiment, the system further comprises a computer workstation for controlling at least one of the means selected from the group consisting of an optical magnification means, illumination means, dispensing means for administration of stimulation agents, imaging means, imaging processing means, and/or operator interfacing means.

In another embodiment of the present invention, a method of optical examination of the cervix of a patient is provided, said method comprising the steps of:
a) applying, at least once, a stimulating and/or contrasting agent to the cervix;
b) acquiring magnified images of the cervix before and after each application of a stimulation agent;
c) identifying essential anatomical objects in the images, i.e., Os, columnar region and transformation zone; and
d) generating an opacity difference score.

Said patient, is preferably, a mammal, particularly preferred a primate, and more particularly preferred a human. It is important to mention that the above mentioned steps do not necessarily have to be carried out in the given order.

In another preferred embodiment of the present invention, the stimulating and/or contrasting agent is at least one selected from the group consisting of opacity difference score detection agent and/or transformation zone detection agent.

The opacity difference score detection agent has two different purposes: First, essential anatomical objects can be identified after stimulation and/or contrasting with said agent. Second, the opacity difference score detection agent serves to create opacity difference scores, which are indicative of neoplastic or cancerous processes, as the degree of acetowhiteness correlates with higher nuclear density in the respective tissues.

The transformation zone detection agent has, preferably, a deep color (iodine solution, for example, has a deep purple or brown color, also termed "mahogany brown"), and serves as a contrasting agent to detect the transformation zone in the cervix, or the area, or shape, of the latter, respectively.

Said opacity difference score detection agent is, preferably, acetic acid, while said transformation zone detection agent is, preferably, iodine solution, such as Lugol's solution or Schiller's solution. Consequently, in yet another preferred embodiment of the method according to the present invention, at least one image, or frame, is acquired before and after application of the opacity difference score detecting agent, (for convenience, these images will be called "pre- and post-acetic acid images" in the following, although said terms will also be used in connection with other opacity difference score detection agents), and/or before and after application of the transformation zone detection agent, (for convenience, these images will be called "pre- and post-iodine solution images" in the following, although said terms will also be used in connection with other transformation zone detection agents).

For the skilled person, alternative stimulating and/or contrasting agents can be derived from the respective literature by routine work, as a matter of course. Alternative agents which can be used to detect areas of higher nuclear density are, for example Methylene blue. Such alternative stimulating and/or contrasting agents are thus comprised by the scope of protection provided by the present invention. This applies also for the terms "pre- and post-acetic acid images" and/or before "pre- and post-iodine solution images". In case an alternative is used for either acetic acid or iodine solution, these terms will be changed accordingly.

In other preferred embodiments of the method according to the present invention, at least one of the following steps is carried out:
a) in the post-acetic acid image and/or in the post-acetic acid image, Os and columnar regions are identified;
b) in the post-iodine solution image, a tentative transformation zone is identified;
c) said tentative transformation zone is mapped to the pre-acetic acid image and the post-acetic acid image;
d) an actual transformation zone is identified by subtracting, in the pre- and post-acetic acid image, the Os and columnar regions from the tentative transformation zone.

The identification of the actual transformation zone is thus a two step approach: (i) In the first step (step b) of the above list, post-iodine solution images are processed to tentatively detect the transformation zone, based on the color changes that the effected cervical zone depicts on the application of the iodine solution. The post-iodine solution image obtained from the key frame extractor is segmented using color based K-means clustering into two clusters. The smaller of the two clusters is selected. The convex hull of this cluster is defined as the tentative transformation zone; (ii) In a second step (step c) of the above list, the tentative transformation zone is mapped to the pre- and post-acetic acid images and then the detected Os and columnar epithelium regions (detected according to step a) of the above listing, are subtracted to define the actual transformation zone (see step d) of the above listing. The pre- and post-acetic acid images can be registered before identifying the transformation zone. The respective image analysis process is shown in FIGS. 6 and 7.

In a particularly preferred embodiment of the method according to the present invention, the opacity difference score is generated by image processing of at least one pre-acetic acid image and one post-acetic acid image. For said processing, preferably only the actual transformation zone data of these images are used based on the prior identification of the actual transformation zone.

In another preferred embodiment of the method according to the present invention, the actual transformation zone (or, preferably, its shape and/or overall area), as determined according to the method of the present invention, and/or the opacity difference score as determined according to the method of the present invention, is indicative of a neoplastic and/or cancerous process.

Very often, the actual transformation zone, as determined after iodine solution staining, and mapping the latter to the post-acetic acid image, can also indicate a cancerous region. According to this definition, the opacity difference score as determined by image processing of at least one pre-acetic acid image and one post-acetic acid image serves to determine the degree of whiteness in the cancerous region, and thus the degree, or severity, of the cancer.

In another embodiment, the shape and/or the total area of the actual transformation zone can be indicative of cancer. The opacity difference score can thus be used to confirm, or revoke, the suspicious neoplastic or cancerous region.

It is particularly preferred that the acquisition of magnified images of the cervix, the identification of essential anatomical objects and/or the generation of opacity difference scores is performed with the help of imaging means and/or image processing means.

Preferably, a colposcope is used for this purpose.

It is furthermore preferred that the acquisition of magnified images of the cervix comprises the steps of:
capturing an image stream;
identifying sequences of interrelated images from said image stream;
identifying key images from these sequences; and
pre-processing the images.

The identification of sequences of interrelated images and/or the identification of key frames comprises, preferably, the steps of:
identifying shot boundaries;
classifying shots; and
selecting key frames.

Furthermore, it is preferred that the identification of essential anatomical objects in the images comprises the steps of:
segmenting pre- and post-acetic acid images using K-means clustering of pixels based on their color into 2 clusters;
labeling smallest cluster as Os+columnar epithelium regions together;
Iteratively removing small and disjoint clusters within both Os and columnar epithelium regions; and
separating Os and columnar epithelium using minimum variance quantization.

In a particularly preferred embodiment, the generation of opacity difference score comprises the steps of:
identifying image pixels with dominant opacity changes in the transformation zone of post-acetic acid images,
mapping said image pixels to the corresponding pixels of the pre-acetic acid images, and
obtaining the opacity difference score using the following formula:

$$OpacityDifferenceScore = \frac{1}{N}\left(\sum (I(i, j) - J(i, j)) \times r(i, j)\right).$$

It is furthermore preferred that the method according to the invention further comprises at least one step selected from the group consisting of a PAP test and/or a molecular test for the Human Papilloma virus.

The PAP test (named after Dr. George Papanicolaou, who has developed it in the first half of the last century) is a screening test used in gynaecology to detect premalignant and malignant processes. A speculum is used to gather cells from the outer opening of the cervix of the uterus and the endocervix. The cells are examined histologically for abnormalities, particularly for neoplastic or cancerous processes of the cervix.

The human papilloma virus (HPV) is a member of the papillomavirus family of viruses that is capable of infecting humans. HPV infection is the cause for nearly all cases of cervical cancer. The presence of viral nucleic acids in a sample taken from the cervix is indicative for HPV infection of the cervix, and is thus a measure for the risk of a patient to develop neoplastic or cancerous processes in the cervix. Modern molecular diagnostic techniques, like PCR, allow for the quick detection of HPV in a sample. One such test is manufactured by Qiagen and is distributed as the digene HC2 HPV DNA test.

The combination of the method according to the invention and one of the two tests set forth above further increases accuracy, sensitivity, and reproducibility of cancer detection in the cervix.

Furthermore, the use of a system according to the invention for carrying out a method according to the invention is provided.

In one aspect the invention provides for system for optical examination of the cervix, said system comprising optical magnification means, illumination means, dispensing means for administration of at least one stimulation and/or contrasting agent, imaging means, and image processing means, said image processing means further comprising:
a key frame extraction means;
optionally, a glare removal means;
an object detection means; and
an opacity change detection means.

In another embodiment the system further comprises operator interfacing means for data input and data output.

In another embodiment the optical magnification means is a colposcope.

In another embodiment said system further comprises a computer workstation for controlling at least one of the means selected from the group consisting of: an optical magnification means, an illumination means, a dispensing means for administration of stimulation agents, an imaging means, an imaging processing means, and/or an operator interfacing means.

In another aspect the invention provides for a method of optical examination of the cervix of a patient, said method comprising the steps of:
a) applying, at least once, a stimulating and/or contrasting agent to the cervix;
b) acquiring magnified images of the cervix before and after each application of a stimulation agent;
c) identifying essential anatomical objects in the images, i.e., Os, columnar region and transformation zone; and
d) generating an opacity difference score.

In another embodiment the stimulating and/or contrasting agent is at least one selected from the group consisting of: an opacity difference score detection agent and/or a transformation zone detection agent.

In another embodiment the opacity difference score detection agent is acetic acid and/or the transformation zone detection agent is iodine solution.

In another embodiment at least one image is acquired before and after application of the opacity difference score detecting agent ("pre- and post-acetic acid images") and/or before and after application of the transformation zone detection agent ("pre- and post-iodine solution images").

In another embodiment of the method, wherein:
a) in the post-acetic acid image, Os and columnar regions are identified;
b) in the post-iodine solution image, a tentative transformation zone is identified;
c) said tentative transformation zone is mapped to the post-acetic acid image; and
d) an actual transformation zone is identified by subtracting, in the pre- and post-acetic acid image, the Os and columnar regions from the tentative transformation zone.

In another embodiment the opacity difference score is generated by image processing of at least one pre-acetic acid image and one post-acetic acid image.

In another embodiment:
a) the actual transformation zone, and/or
b) the opacity difference score
is indicative of a neoplastic, or cancerous, process.

In another embodiment the identification of essential anatomical objects in the images comprises the steps of:
segmenting pre- and post-acetic acid images using K-means clustering of pixels based on their color into 2 clusters;
labeling smallest cluster as Os+columnar epithelium regions together;
iteratively removing small and disjoint clusters within both Os and columnar epithelium regions; and
separating Os and columnar epithelium using minimum variance quantization.

In another embodiment the generation of opacity difference score comprises the steps of
identifying image pixels with dominant opacity changes in the transformation zone of post-acetic acid images;
mapping said image pixels to the corresponding pixels of the pre-acetic acid images; and
obtaining the opacity difference score using the following formula:

$$OpacityDifferenceScore = \frac{1}{N}(\sum (I(i, j) - J(i, j)) \times r(i, j)).$$

In another embodiment said method further comprises conducting a PAP test and/or a molecular test for human papilloma virus.

In another aspect the invention provides for a system according to an embodiment of the invention for carrying out a method according to an embodiment of the invention.

In one aspect the invention provides for a medical instrument for examining the cervix. The medical instrument comprises an optical examination system for acquiring a cervical image. A cervical image as used herein encompasses an image which is descriptive of a cervix. The medical instrument further comprises a processor for controlling the medical instrument. The medical instrument further comprises a memory containing machine-executable instructions for execution by the processor. Execution of the instructions causes the processor to acquire the cervical image using the optical examination system. Execution of the instructions further causes the processor to calculate a set of interest point locations using a digital filter. In some embodiments the digital filter is a Harris Corner Detector.

Execution of the instructions further causes the processor to calculate a filtered set of interest points located using the set of interest point locations and a morphological filter. The morphological filter uses optical properties of the set of interest points to determine which ones should be filtered. For instance punctation marks should be dark with respect to the background and be point-like in nature.

Execution of the instructions further causes the processor to calculate a reduced set of interest point locations using the filtered set of interest point locations and a neighborhood-based filter. Typically punctation marks occur together in groups. Excluding punctation marks or filtered points of interest that are far away from other punctation marks helps to eliminate false positives.

In another embodiment execution of the instructions further causes a classified set of interest point locations using a trained classification module and the reduced set of interest points. A trained pattern detection software module can be used to detect or determine if a punctation mark is similar to existing or previously known punctation marks.

In another embodiment execution of the instructions further causes the processor to calculate a set of punctation locations using a second neighborhood-based filter and the classified set of interest point locations. The second neighborhood-based filter examines groupings of the punctation marks and uses them to help eliminate false positives. Execution of the instructions further causes the processor to calculate punctation mark regions using the punctation point locations.

In another embodiment the trained classification module is a randomized tree classification module.

In another embodiment execution of the instructions further causes the processor to generate a set of excluded locations within the cervical image with a pre-processing filter before calculating the first set of interest point locations. The digital filter uses the set of excluded locations to generate the set of interest points.

In another embodiment execution of the instructions further causes the processor to acquire a second cervical image using the optical examination system. Execution of the instructions further causes the processor to calculate a second set of interest point locations using the digital filter. Execution of the instructions further causes the processor to calculate a second filtered set of interest point locations using the second set of interest point locations and the morphological filter. Execution of the instructions further causes the processor to calculate a second reduced set of interest point locations using the second filtered set of interest point locations and the neighborhood-based filter. Execution of the instructions further causes the processor to calculate a second classified set of interest point locations using the trained classification module and the second reduced set of interest points. Execution of the instructions further causes the processor to calculate a second set of punctation locations using the second neighborhood-based filter and the second classified set of interest point locations. The punctation mark regions using the punctation point location and the second punctation point locations.

In another embodiment the first cervical image is a first pre-acetic acid image.

In another embodiment the first cervical image is a first green filter image.

In another embodiment the first cervical image is a first post-acetic acid image. The second cervical image is a second pre-acetic acid image.

In another embodiment the second cervical image is a second pre-acetic acid image.

In another embodiment the second cervical image is a second green filter image.

In another embodiment the second cervical image is a second post-acetic acid image.

In another embodiment execution of the instructions further causes the processor to register the first image and the second image using an image registration module. In the image registration features in the first image are identified in the second image.

In another embodiment execution of the instructions causes the processor to acquire the first cervical image and the second cervical image by acquiring video data comprising multiple image frames. Execution of the instructions causes the processor to select the first cervical image and the second cervical image from the multiple image frames. Execution of the instructions further causes the processor to receive the video data comprising multiple image frames. Execution of the instructions further causes the processor to determine a transformation model between each pair of consecutive image frames selected from the multiple image frames. Execution of the instructions further causes the processor to calculate a cumulative transformation model from the transformation model between each pair of consecutive image frames. Execution of the instructions further causes the processor to register each of the multiple image frames using the cumulative transformation model. Execution of the instructions further causes the processor to provide the registration of the first cervical image and the second cervical image using the cumulative transformation model. Essentially the video data is comprised of many different image frames. A transformation model is used to calculate the change between each of the adjacent image frames. A cumulative transformation model is then used to calculate a registration between the first cervical image and the second cervical image. This may have the advantage of providing a more accurate registration between the first cervical image and the second cervical image.

In another embodiment execution of the instructions further causes the processor to detect a failure determining the transformation model between the at least one pair of consecutive image frames. A failure may be for example the ability to determine a transformation model between a pair of consecutive image frames. Execution of the instructions further causes the processor to calculate a first image segmentation from a first image frame selected from the video data before the failure. Execution of the instructions further causes the processor to calculate a second image segmentation from a second image frame selected from the video data after the failure. The image segmentation in both cases may be calculated using a standard image segmentation software module. For instance the image segmentation module may contain specialized code for recognizing certain ornithological features of the cervix in the image. It may also use such things as a deformable model or other modeling means to perform the image segmentation.

Execution of the instructions further causes the processor to determine a second transformation between the first image frame and the second image frame. Execution of the instructions further causes the processor to correct the cumulative transformation model using the second transformation. Essentially the first and second image segmentations provide a way of registering the second image frame to the first image frame. The image segmentations may therefore be used to calculate a transformation between the first image frame and the second image frame. This may then be used as a bridge to repair or correct the cumulative transformation model.

In some embodiments the second transformation model is determined in the same way as the transformation model between adjacent frames is determined.

In another embodiment execution of the instructions further causes the processor to detect a failure of determining a transformation between the at least one pair of consecutive image frames. Execution of the instructions further causes the processor to choose a first image from the video data before the failure. Execution of the instructions further cause the processor to choose a second image frame from the video data after the failure. Execution of the instructions further causes the processor to determine a second transformation between the first image and the second image. Execution of the instructions further causes the processor to correct the cumulative transformation model using the second transformation. In some embodiments the second transformation can be performed the same way as the transformation model between the pairs of consecutive image frames is determined.

In another embodiment the first cervical image is a pre-contrast and/or pre-stimulating agent image. The second cervical image is a post-contrast and/or post-stimulating agent image. Execution of the instructions further causes the processor to identify essential anatomical objects in the image. For example the essential anatomical objects may be, but are not limited to Os, columnar region, and transformation zone. Execution of the instructions further cause the processor to generate an opacity difference score. These steps of the processor may for instance be used for performing a method of optical examination of the cervix of a patient. The method may comprise the steps of applying, at least once a stimulating and/or contrasting agent into the cervix. The method may further comprise acquiring magnified images of the cervix before and after each application of the stimulating agent. The method may further comprise identifying essential anatomical objects in the image, i.e. Os, columnar region and transformation zone. The method may further comprise the step of generating an opacity difference score.

In another embodiment the second cervical image is a zoom image showing a zoomed region at least partially within the first cervical image.

In another embodiment execution of the instructions further causes the processor to display the punctation mark regions superimposed on the first cervical image on a display.

In another aspect the invention provides for a computer program product comprising machine-executable instructions for execution by a processor for controlling the medical instrument for examining the cervix. The medical instrument comprises an optical examination system for acquiring a cervical image. Execution of the instructions causes the processor to acquire the cervical image using the optical examination system. Execution of the instructions further causes the processor to calculate a set of interest point locations using a digital filter. Execution of the instructions further causes the processor to calculate a filtered set of interest point locations using the set of interest point locations and a morphological filter. Execution of the instructions further cause the processor to calculate a reduced set of interest point locations using the filtered set of interest point locations and a neighborhood-based filter. Execution of the instructions further causes the processor to calculate a classified set of interest point locations using a trained classification module and the reduced set of interest points.

Execution of the instructions further causes the processor to calculate a set of punctation locations using a second neighborhood-based filter and the classified set of interest point locations. Execution of the instructions further causes the processor to calculate punctation mark regions using the punctation point locations.

In another aspect the invention provides for a method of video registration comprising the step of receiving video data comprising multiple image frames. The method further comprises the step of determining a transformation between each pair of consecutive image frames selected from the multiple image frames. The method further comprises the step of calculating a cumulative transformation model from the transformation between each pair of consecutive image frames. The method further comprises the step of registering each of the multiple image frames using the cumulative transformation. This embodiment may be beneficial because it provides an efficient way of registering frames within the video data to each other.

In another embodiment a Lucas-Kanade tracking algorithm is used to determine the transformation.

In another embodiment the transformation is determined by tracking SIFT features.

In another embodiment the transformation is determined by a simultaneous localization and mapping algorithm to drive feature matches.

In another embodiment the method further comprises the step of detecting a failure of determining a transformation between the at least one pair of consecutive image frames. The method further comprises the step of calculating a first image segmentation from a first image frame selected from the video data before the failure. The method further comprises the step of calculating a second image segmentation from a second image frame selected from the video data after the failure. The method further comprises the step of determining a second transformation between the first image frame and the second image frame. The method further comprises the step of correcting the cumulative transformation using the second transformation.

In some embodiments the determination of the second transformation can be performed the same way as the determination of the transformation between each pair of consecutive image frames.

In another embodiment the method further comprises the step of detecting a failure to determine a transformation between the at least one pair of consecutive image frames. The method further comprises the step of omitting the unreliably determined transformation from the cumulative transformation model.

In another embodiment the method further comprises the step of detecting a failure determining a transformation between the at least one pair of consecutive image frames. The method further comprises the step of calculating a first image segmentation from a first image frame selected from the video data before the failure. The method further comprises the step of calculating a second image segmentation from a second image frame selected from the video data after the failure. The first and second image segmentation may be determined using a third image segmentation technique. The method further comprises the step of correcting the cumulative transformation model using the first image segmentation and the second image segmentation.

In another embodiment the method further comprises the step of detecting a failure to determine a transformation between the at least one pair of consecutive image frames. The method further comprises the step of choosing a first image frame from the video data before the failure. The method further comprises the step of choosing a second image frame from the video data after the failure.

The method further comprises the step of determining a second transformation between the first image and the second image. The method further comprises the step of correcting the cumulative transformation model using the second transformation.

In some embodiments the second transformation can be performed the same way as the transformation which determines the transformation between each pair of consecutive images.

In another embodiment the first image segmentation is a first contour. The second image segmentation is a second contour. Execution of the instructions further causes the processor to determine a transformation between the first contour and the second contour. The cumulative transformation is corrected using the transformation.

In another embodiment the transformation is determined using contour-based matching.

In another embodiment the first image segmentation and the second image segmentation is performed in a region of interest.

In another embodiment the method further comprises the step of receiving the region of interest. This may be the receiving of the region of interest from another computer system or from a user interface being manipulated by a user. It may also include receiving the region of interest as determined by a software module.

In another embodiment the region of interest is received from an operator.

In another embodiment the transformation is determined by locating feature correspondences between each pair of consecutive image frames using a feature identification algorithm. The transformation is further determined by calculating the transformation using the feature correspondences.

In another embodiment the feature identification algorithm is operable for mapping identical features between the adjacent frames using warping and translation.

In another aspect the invention provides for a computer program product for performing any one of the aforementioned methods of video registration.

In another aspect the invention provides for a medical instrument comprising an optical examination system for acquiring a cervical image. The medical instrument further comprises a processor for controlling the medical instrument. The medical instrument further comprises a memory containing machine executable instructions for execution by the processor. Execution of the instructions causes the processor to acquire a saline cervical image. The saline cervical image is a cervical image acquired after the cervix has been washed with a saline solution. Execution of the instructions further cause the processor to acquire multiple acetowhite cervical images using the optical examination system. The multiple acetowhite cervical images are cervical images that have been acquired after the cervix has been washed with an acetic acid solution. The multiple acetowhite cervical images may be acquired at different times so that the acetowhite kinetics can be examined or determined. Execution of the instructions further causes the processor to acquire an iodine cervical image using the optical examination system. The iodine cervical image is a cervical image acquired after an iodine bath or solution has been applied.

Execution of the instructions further causes the processor to calculate an acetowhite kinetic score using the acetowhite cervical images. Execution of the instructions further causes the processor to calculate an acetowhite margin score using the acetowhite cervical images. Execution of the instructions further causes the processor to calculate a vascular pattern score using the acetowhite cervical images and the saline cervical image. The vascular pattern is noted in both the acetowhite cervical images and the saline cervical images. If a vascular pattern disappears in the acetowhite cervical images that were present in the saline cervical images it may indicate the presence of a cancerous tumor.

Execution of the instructions further causes the processor to calculate an iodine staining score using the iodine cervical image. The iodine staining score is a score determined by the location of iodine uptake by tissues in the cervix. Execution of the instructions further causes the processor to determine a colposcopy index score by summing the acetowhite kinetic scores, the acetowhite margin score, the vascular pattern score, and the iodine staining score. This embodiment may be advantageous because the determination of the colposcopy index score may provide an aid in either training a physician to perform a diagnosis or in assisting a physician in diagnosing a cervical cancer.

In another embodiment the medical instrument further comprises a display and a user interface. The display may be a display configured for displaying information or graphics. The user interface encompasses any device which may be used for inputting data or a response by a user.

In another embodiment execution of the instructions further causes the processor to display at least one of the acetowhite cervical images on the display. Execution of the instructions further causes the processor to display the acetowhite kinetic score on the display. Execution of the instructions further causes the processor to receive a corrected acetowhite kinetic score from the user interface. The colposcopy index score is at least partially determined using the corrected acetowhite kinetic score. This embodiment may be advantageous because a physician or the healthcare provider may want to review at least one of the acetowhite cervical images and the acetowhite kinetic score. The physician or healthcare provider may then agree or disagree with the acetowhite kinetic score. This may be useful in training physicians; it may also be useful in training the operation and function of the medical instrument. For instance the acetowhite kinetic score may be determined using an opacity index for the time-dependent acetowhite cervical images. Receiving the corrected acetowhite kinetic score may provide empirical data which may be used to increase the accuracy of the scoring process of the acetowhite kinetics.

In another aspect execution of the instructions further causes the processor to display at least one of the acetowhite cervical images on the display. Execution of the instructions further causes the processor to display the acetowhite margin score on the display. Execution of the instructions further causes the processor to receive a corrected acetowhite margin score from the user interface. The colposcopy index score is at least partially determined using the corrected acetowhite margin score. This embodiment may be advantageous because again it may provide a training opportunity for physicians or other healthcare providers and also the receiving of the corrected acetowhite margin score may be used to provide empirical data which may provide a more accurate scoring process of the acetowhite cervical images.

In another embodiment execution of the instructions further causes the processor to display at least one of the acetowhite cervical images on the display. Execution of the instructions further causes the processor to display the vascular pattern score on the display. Execution of the instructions further causes the processor to receive a corrected vascular pattern score from the user interface. The colposcopy index score is at least partially determined using the corrected vascular pattern score. Again this embodiment may be useful for training physicians or healthcare providers and also the receiving of the corrected vascular pattern score may be useful for improving the algorithm for scoring the vascular patterns.

In another embodiment execution of the instructions further causes the processor to display at least one of the acetowhite cervical images on the display. Execution of the instructions further causes the processor to display the iodine staining score on the display. Execution of the instructions further causes the processor to receive a corrected iodine staining score from the user interface. The colposcopy index score is at least partially determined using the corrected iodine staining score. This embodiment may be beneficial because it may provide a method of helping to train physicians and/or healthcare providers. Also the receiving of the corrected iodine staining score may provide for a more accurate scoring of the iodine staining. The iodine staining score may be derived from dividing different regions of the cervix into iodine uptake positive regions and iodine uptake negative regions. The corrected iodine staining score may be used to help correct the proper identification of regions which have uptake in iodine and also their location relative to the transformation zone.

In another embodiment execution of the instructions further causes the processor to determine an opacity index score for the acetowhite cervical images. The acetowhite kinetic score is calculated at least partially using the opacity index score.

In another embodiment execution of the instructions further causes the processor to calculate a time-dependent opacity index for the acetowhite cervical images. The opacity index score is determined from the time-dependent opacity index by binning the time-dependent opacity index into a predetermined opacity index range. Essentially the opacity index of each of the acetowhite cervical images may be determined. This may be plotted or stored as the time-dependent opacity index. Then using a set of predetermined opacity index ranges or criteria the time-dependent opacity index may be binned into one of several different scores. This binning may use empirically determined criteria. For instance a physician could make a diagnosis using a set of acetowhite cervical images and then using the physician's diagnosis on a large number of sets of acetowhite cervical images the proper binning for the particular opacity index score could be determined.

In another embodiment execution of the instructions further causes the processor to select at least one of the acetowhite cervical images. Execution of the instructions further causes the processor to identify a transformation zone in the at least one of the acetowhite cervical images. Execution of the instructions further causes the processor to identify acetowhite margins in the at least one of the acetowhite cervical images. The acetowhite margin score is calculated at least partially using the location of the transformation zone and the acetowhite margins.

In another embodiment execution of the instructions further causes the processor to threshold the at least one acetowhite cervical image to determine an acetowhite boundary sharpness. The acetowhite margin score is calculated at least partially using the acetowhite boundary sharpness.

In another embodiment if the acetowhite margins are outside of the transformation zone the acetowhite margin score is assigned a first value. If the acetowhite margins are within the transformation zone the acetowhite margin score is assigned a second value or a third value by comparing the acetowhite boundary sharpness to a predetermined threshold. This embodiment may be advantageous because empirically used data may be used to accurately determine an acetowhite margin score.

In another embodiment execution of the instructions further causes the processor to identify mosaics, the punctation mark regions, and/or atypical vessels in the saline cervical image. Execution of the instructions further causes the processor to identify post-acetic acid mosaics, post acetic acid punctation mark regions, and/or post-acetic acid atypical vessels in the acetowhite cervical image selected from the acetowhite cervical images. The post-acetic acid mosaics, post acetic acid punctation mark regions, and post-acetic acid atypical vessels are simply the mosaics, punctation mark regions, and atypical vessels identifiable after an acetic acid bath or wash has been applied to the cervix. The vascular pattern score is calculated using the difference between any one of the following: the mosaics and the post-acetic acid mosaics, the punctation mark regions, and the post-acetic acid punctation mark regions, and the atypical vessels and the post-acetic acid atypical vessels, and combinations thereof. This may be advantageous because if these structures disappear after acetic acid has been applied it may be indicative of the presence of a cancer in the cervix.

In another embodiment execution of the instructions further cause the processor to identify a transformation zone in the iodine cervical image. Execution of the instructions further causes the processor to create a color histogram of the iodine cervical image. Execution of the instructions further cause the processor to threshold the iodine cervical image into iodine positive and iodine negative regions using the color histogram. The iodine staining score is calculated at least partially by identifying iodine positive regions in the transformation zone.

In another embodiment the iodine staining score is assigned a first iodine value if the transformation zone is iodine positive. The iodine staining score is assigned a second iodine value if the transformation zone is iodine positive and iodine negative. The iodine staining score is assigned a third value if an acetowhite region is iodine negative.

In another embodiment execution of the instructions further causes the processor to receive an annotation using the user interface. Execution of the instructions further causes the processor to display the annotation on the display. This may be particularly useful in training physicians and healthcare providers; it may also be useful in providing information to physicians regarding a specific patient's health.

In another embodiment execution of the instructions further causes the processor to store the annotation in a patient record. In some embodiments the annotations may be stored with the image. This may be useful because an expert physician or healthcare provider can put annotations or remarks into the patient record which a different physician or healthcare provider may use and find useful in diagnosing or treating a subject.

DEFINITIONS

As used herein, the term "optical magnification means" relates to a device, or algorithm, which is capable of magnifying an optical image, for example a magnification lens, a microscope, or a digital image processing system in which the magnification is carried out digitally, or electronically.

As used herein, the term "colposcope" refers to a low-power microscope with a powerful light source, which is used for magnified visual examination of the uterine cervix to help in the diagnosis of cervical cancer. In some cases, the colposcope may be a stereographic and binocular field microscope. In other cases the colposcope is a monocular microscope.

The term "Os" relates to the external orifice of the cervix, which is an interior narrowing of the uterine cavity. It corresponds to a slight constriction known as the isthmus that can be observed on the surface of the uterus about midway between the apex and base.

The term "columnar region" relates to a region of the epithelium of the cervix. The ectocervix is composed of non-keratinized stratified squamous epithelium. The endocervix (more proximal, within the uterus) is composed of simple columnar epithelium, i.e., the "columnar region".

The term "transformation zone" relates to the area adjacent to the border of the endocervix and ectocervix. The transformation zone undergoes metaplasia numerous times during normal life. This metaplastic potential, however, increases the risk of cancer in this area—the transformation zone is the most common area for cervical cancer to occur.

The term "tentative transformation zone" relates to the transformation zone as provisionally detected after iodine solution staining.

The term "actual transformation zone" relates to the transformation zone as determined after mapping the tentative transformation zone to the post-acetic acid image. The actual transformation zone is often also called "cancerous region" due to high risk of neoplastic, or cancerous, processes.

The term "dispensing means" relates to a device which is useful for applying, in a controlled manner with respect to time, volume and position, at least one stimulation and/or contrasting agent to a given object. Preferably, such dispensing means is a syringe, a pipette or the like.

The term "frame grabber" means a device which has the capability to convert the output of an analogue video frame imaging device or analogue scan converter into a digital image for further image processing.

The term "key frame extraction means" relates to a device or an algorithm that can automatically identify at least one pre-acetic acid image, post-acetic acid image and post-Iodine solution image.

The term "glare removal means" relates to a device, or an algorithm, which is capable of removing glare in a digital image, for example.

The term "image processing means" (or image processor) relates to a digital image processing device, or software, which is capable of inputting, computing, and outputting digital image data.

The term "opacity change detection means" (or opacity change detector) relates to a digital image processing device, or software, which is capable detecting opacity changes in at least two corresponding images, e.g., as described in the present specification.

The term "object detection means" (or object detector) relates to a digital image processing device, or software, which is capable of detecting and/or identifying objects in a digital image.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, punched tape, punch cards, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. The memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage devices. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, one or more switches, one or more buttons, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

BRIEF DESCRIPTION OF THE DRAWINGS

These and other aspects of the invention will be apparent from and elucidated with reference to the embodiments described hereinafter. In the drawings:

FIG. 9 shows a flow diagram which illustrates a method according to an embodiment of the invention;

FIG. 12 shows the relationship of several software modules within an embodiment of the invention;

FIG. 13 shows a flow diagram which illustrates a method according to an embodiment of the invention;

FIG. 20 shows image 1900 after morphological filtering;

FIG. 21 shows image 2000 after neighbourhood filtering;

FIG. 22 shows image 2100 after using an RT classifier;

FIG. 23 shows image 2200 after using a second neighbourhood filter;

FIG. 44 illustrates a user interface according to an embodiment of the invention;

FIG. 53 illustrates a different view of the user interface shown in FIG. 49;

FIG. 56 illustrates a different view of the user interface shown in FIG. 49;

FIG. 58 illustrates a different view of the user interface shown in FIG. 49;

FIG. 59 illustrates a different view of the user interface shown in FIG. 49;

FIG. 60 illustrates a different view of the user interface shown in FIG. 49;

DETAILED DESCRIPTION OF EMBODIMENTS

A colposcope according to the invention (see FIG. 1), has a key frame extractor, pre-processor, object detector and opacity change detector. Key frame extractor takes as input the video that comes from the colposcope which is displayed to the gynaecologist. The images (pre-acetic acid, post-acetic acid and post-iodine solution) containing the cervical region at the same optical magnification are extracted (in the present application, the words frames and images are used interchangeably). In the pre-processor, glare caused by specular reflection in the images is removed, according to which a feature image is extracted from a color image that provides a good glare to background ratio. The glare containing regions in the feature image are detected and extended to cover all pixels that have been affected by the glare. The glare in the affected regions is then removed by filling in an estimate of the underlying image features.

The de-glared image is then sent to the object detector. The object detector processes the images to identify the Os, columnar epithelium and the transformation zone, based on segmentation techniques that use the color and intensity information.

Figure 2:
FIG. 2 shows a flow diagram of the method according to the invention.
Figure 3:
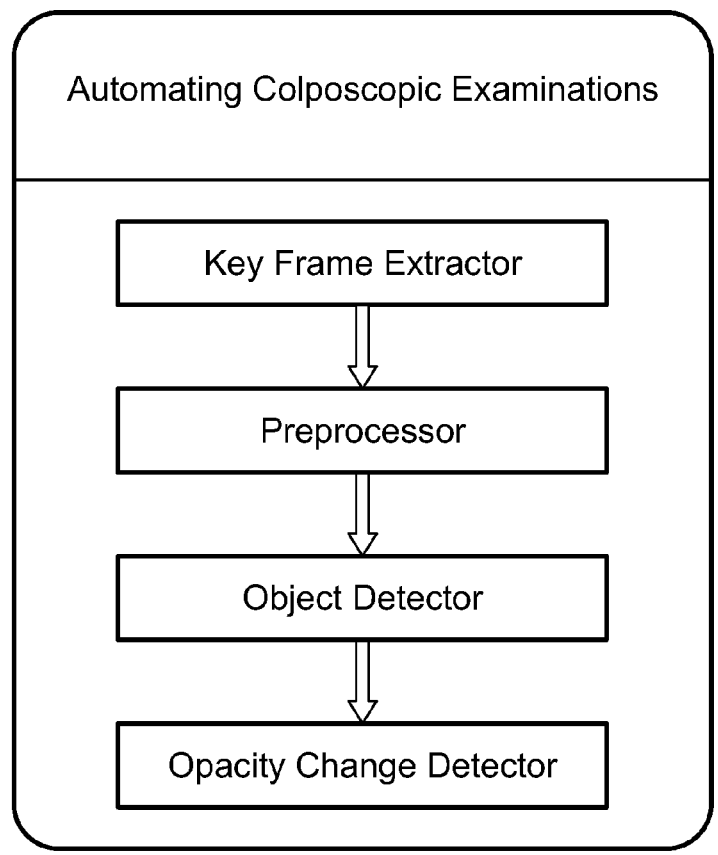
FIG. 3 shows a flow diagram for the method to automate colposcope images.

This information is then used by the opacity change detector to estimate the degree of whiteness in the transformation zone and thus the degree of cancer. The flow diagrams of the proposed method are shown in FIGS. 2 and 3.

The key frame extractor takes as input the 2D video that comes out of the colposcope. It divides the videos into shots by identifying the shot boundaries and then extracting the relevant images from each shot. The types of images extracted are the pre-acetic acid images, post-acetic acid images and post-iodine solution images having the same magnification factor.

Shot Boundary Identifier

Figure 4B:
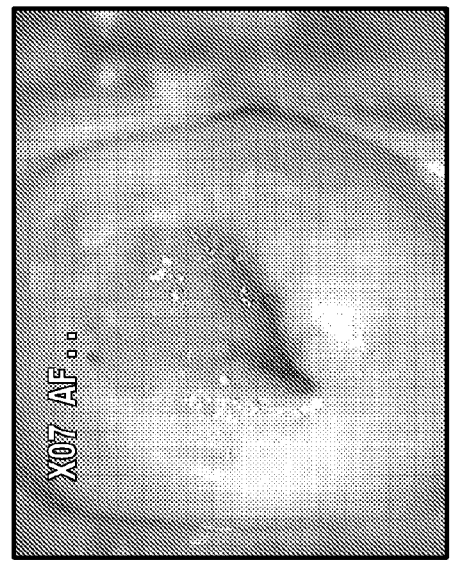
FIG. 4b shows a raw colposcopic image.
Figure 4D:
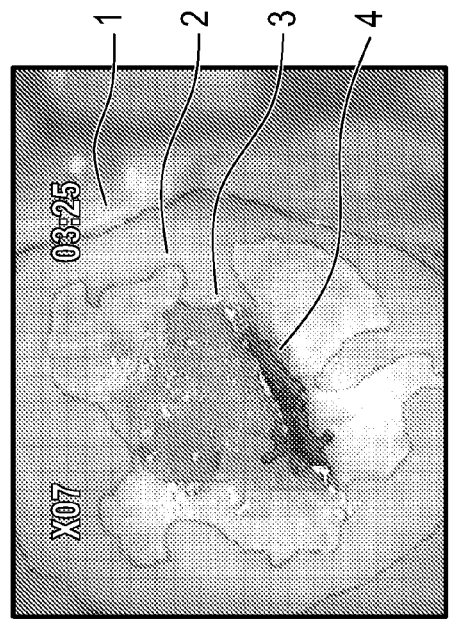
FIG. 4d shows the objects in a colposcopic image identified with methods according to the invention, i.e., Cervix (1), Transformation zone (2), Columnar epithelium (3) and Os (4)
Figure 4A:
FIG. 4a shows a colposcopic image showing the process when acetic acid is applied to the cervix.

While performing colposcopy, viewing the cervix at different magnification levels and application of different chemicals, like acetic acid (see FIG. 4a) or iodine solution, to the cervix can be considered as different shots in general video processing applications. A shot/view is defined as a sequence of interrelated images captured from the colposcope, which represents a continuous action in time and space. A "view boundary" is defined herein as the point of switching over from one view to another while performing the colposcopy. Classical shot boundary detection algorithms proposed in context of general purpose video applications can be used to detect shot boundaries. Color features have been used for shot detection.

Key Frame Selection

Once the shots are identified, key images are automatically selected from each shot. The key frames are from the following shots: pre-acetic acid, post-acetic acid and post-iodine solution. Each frame or image in a shot is described with a set of features based on color, texture, area of the cervix, etc. A score, a is assigned to each frame which is a function of the set of features used. The frame with maximum a is selected as the key frame in a shot.

Preprocessor

Figure 4C:
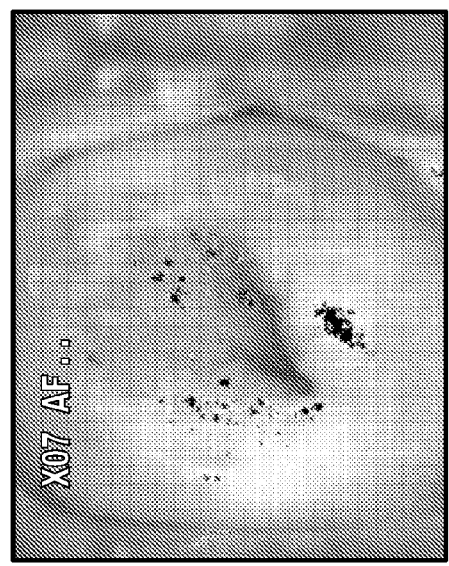
FIG. 4c shows the same image with glare pixels removed.
Figure 5B:
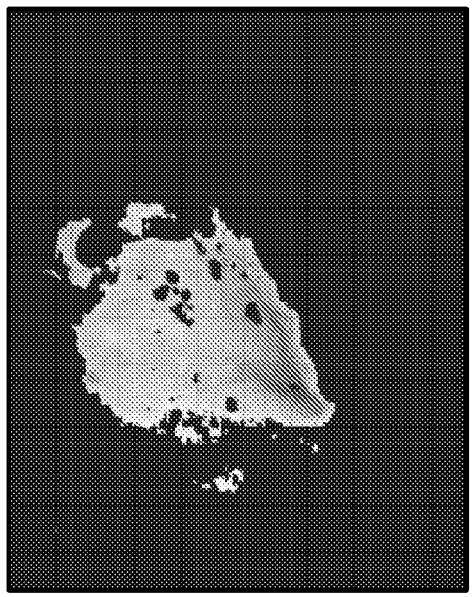
FIG. 5b shows the Os and Columnar epithelium regions identified together.
Figure 5D:
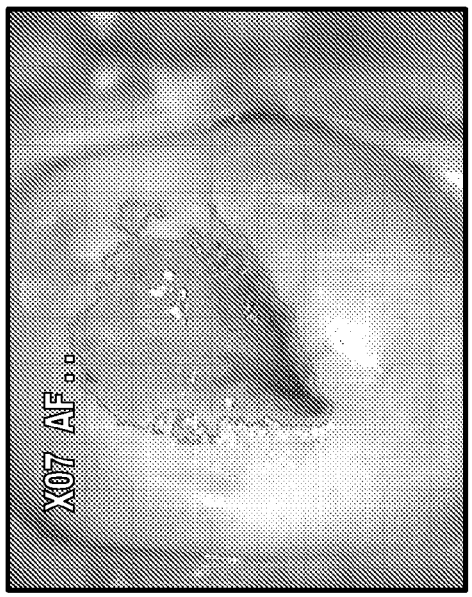
FIG. 5d shows the Os and columnar epithelium demarked after removing the small and disjointed clusters.
Figure 5A:
FIG. 5a shows a colposcopic image taken after acetic acid has been applied.
Figure 5C:
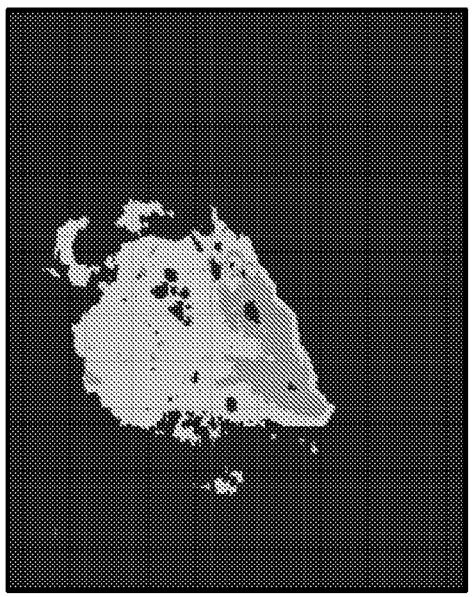
FIG. 5c shows the Os and columnar regions separated.

The preprocessor takes as input the key images selected by the key frame extractor. Quality of cervical images is attributed to many factors including glare/glint/specular reflection. The glare eliminates the color information in affected pixels and thus makes image analysis algorithms unreliable. It is therefore essential to remove the glare from colposcope images which is done in the preprocessor. The glare regions are detected as small, saturated and high contrast regions. An image, T, is opened in RGB color space. The G component of the RGB color space is used as feature space as it provides a good glare to background ratio. Local maxima for a histogram generated by the G component are identified that represent saturated values. A mask for the glare pixels is generated and applied on the image T to remove the glare pixels from it (see FIG. 4c).

Object Detector

The object detector takes as input the key frame images from which the glare pixels have been filtered out. The object detector aims at identifying relevant objects of the cervix (1), like the Os (4), columnar epithelium (3) and the transformation zone (2), see FIG. 4d.

Os and Columnar Region Detection

Os and columnar regions are identified using the following steps:

Segmenting post-acetic colposcope images using K-means clustering of pixels based on their color into 2 clusters;

Smallest cluster is labeled as Os+columnar epithelium region;

Separate Os and columnar epithelium using minimum variance quantization; and

Iteratively remove small and disjoint clusters within both Os and columnar epithelium regions.

The respective image analysis process is shown in FIG. 5.

Transformation Zone Detection

Figure 6A:
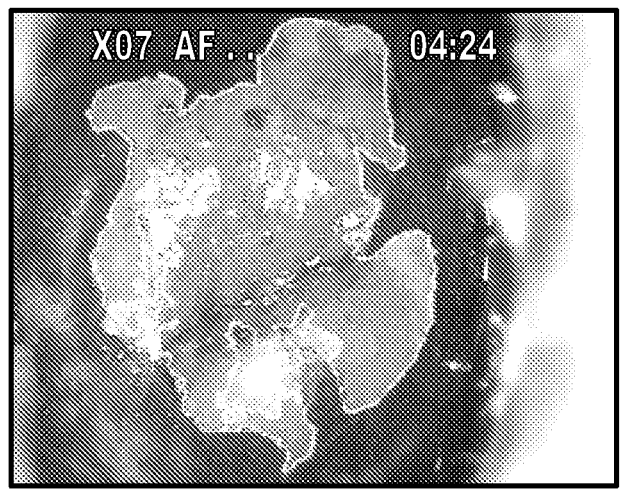
FIG. 6a shows a tentative transformation zone identified in post-iodine solution image (black line)
Figure 6B:
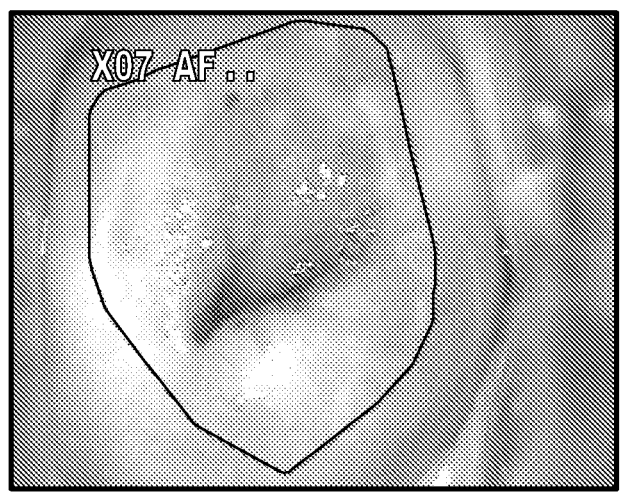
FIG. 6b shows the tentative transformation zone mapped to the post-acetic acid
images.
Figure 6C:
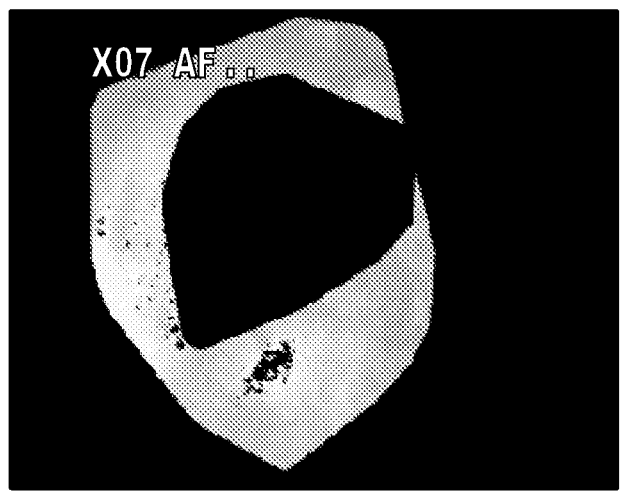
FIG. 6c shows the actual transformation zone.

Detecting transformation zone in the post-acetic acid images is a two step approach. In the first step, post-iodine solution images are processed to tentatively detect the transformation zone based on the color changes that the affected cervical zone depicts on the application of iodine solution. The post-iodine solution image obtained from the key frame extractor is segmented using color based K-means clustering into two clusters. The smaller of the two clusters is selected. The convex hull of this cluster is defined as the tentative transformation zone. This is followed by a second step where the tentative transformation zone is mapped to the pre- and post-acetic acid images and then the detected Os and columnar epithelium regions are subtracted to define the actual transformation zone. The pre- and post-acetic acid images can be registered before identifying the transformation zone. The respective image analysis process is shown in FIG. 6.

Opacity Change Detector

This module takes as input the transformation zones identified in the pre- and post-acetic acid images and generate an opacity difference score for all post-acetic acid images with respect to the pre-acetic acid images. Broadly, in the post-acetic acid images, pixels in the transformation zone which show dominant opacity changes are identified and they are compared with their corresponding pixels in pre-acetic acid image. The steps to generate the opacity difference score are as follows:

convert the RGB values of the transformation zone in post-acetic acid images to Lab color space (L component closely matches human perception of lightness/whiteness);

cluster pixels in the transformation zone to two levels of whitish regions, i.e., dominant opacity change and minor opacity change (to match opaque white, and translucent white practiced clinically);

remove the pixels with minor opacity change; and identify the corresponding pixels of the dominant opacity change in the pre-acetic acid image.

Finally each post-acetic acid image is given an opacity difference score with respect to the pre-acetic acid image using the following formula:

$$OpacityDifferenceScore = \frac{1}{N}\left(\sum (I(i, j) - J(i, j)) \times r(i, j)\right)$$

where:

I=Image with dominant pixels in pre-acetic acid image;
J=Image with dominant pixels in post-acetic acid image;
N=Number of pixels with dominant opacity changes;
r=Binary image with dominant opacity changes; and
(i,j)=A pixel in the spatial domain of image I/J/r.

The respective image analysis process is shown in FIGS. 7 and 8.

FIG. 9 shows a flow diagram which illustrates a method according to an embodiment of the invention. In step 900 a cervical image is acquired using an optical examination system. Next in step 901 a set of interest point locations is calculated using a digital filter. Next in step 902 a filtered set of interest point locations are calculated using the set of interest point locations and a morphological filter. In step 903 a reduced set of interest point locations is calculated using the filtered set of interest point locations and a neighborhood-based filter. Next in step 904 a classified set of interest point locations is calculated using a trained classification module and the reduced set of interest points. Next in step 906 a set of punctation locations is calculated using a second neighborhood-based filter and the classified set of interest point locations. Finally in step 908 punctation mark regions are calculated using the punctation point locations.

Figure 10:
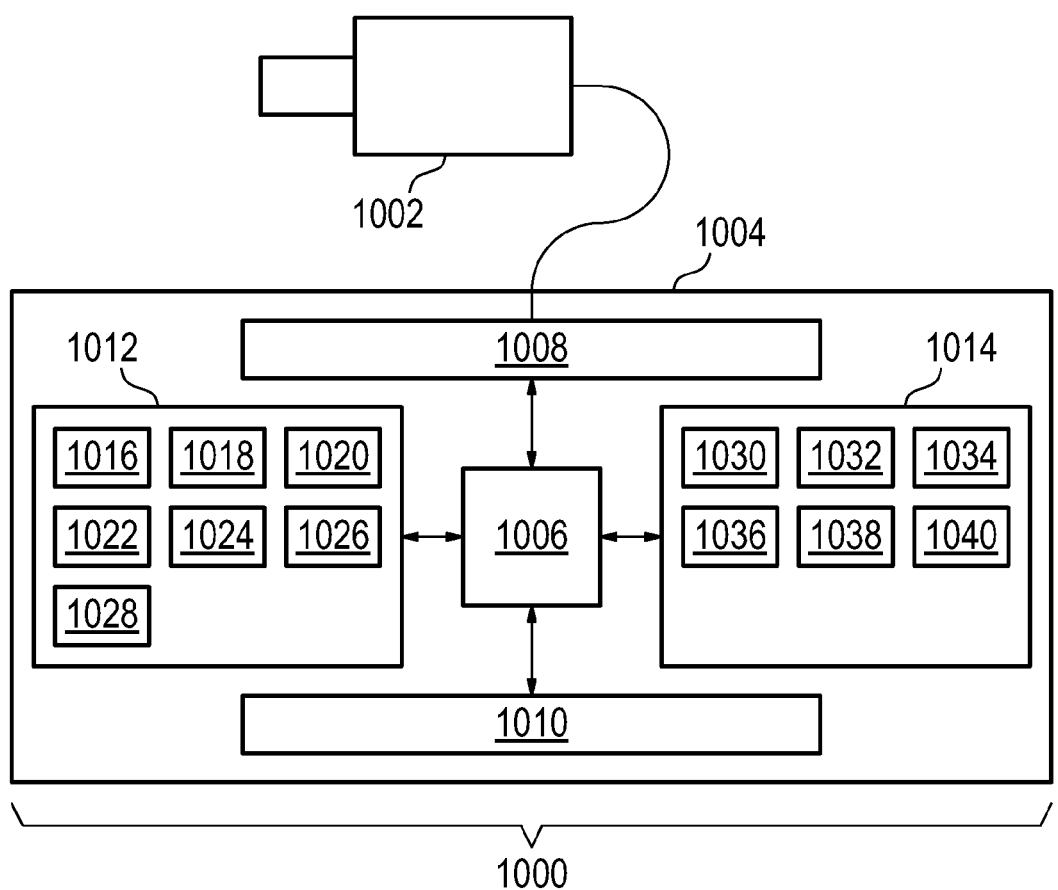
FIG. 10 illustrates a medical instrument according to an embodiment of the invention.

FIG. 10 shows a medical instrument 1000 according to an embodiment of the invention. The medical instrument comprises an optical examination system 1002 and a computer 1004. The computer 1004 comprises a processor 1006. The processor 1006 is connected to a hardware interface 1008, a user interface 1010, computer storage 1012 and computer memory 1014. The optical examination system 1002 is connected to the hardware interface 1008. This enables the optical examination system 1002 to transfer images to the computer 1004. Within the computer storage 1012 is stored a cervical image 1016 acquired with the optical examination system 1002. Also within the computer storage 1012 is a set of interest points 1018 calculated from the cervical image 1016. Within the computer storage 1012 there is also a filtered set of interest points 1020 which has been calculated using the set of interest points 1018. Within the computer storage 1012 is a reduced set of interest points 1022 calculated from the filtered set of interest points 1020. Within the computer storage 1012 there is a classified set of interest points 1024 calculated from the reduced set of interest points 1022. Within the computer storage 1012 there is a set of punctation locations 1026 calculated from the classified set of interest points 1024. Finally within the computer storage 1012 there are punctation mark regions 1028 which have been calculated from the set of punctation locations 1026.

Within the computer memory 1014 there is a control module. The control module contains computer-executable code for controlling the operation and function of the medical instrument 1000. Within the computer storage 1014 there is a digital filter 1032. The digital filter 1032 was used to calculate the set of interest points 1018 from the cervical image 1016. Within the computer memory 1014 there is a morphological filter 1034. The morphological filter 1034 contains computer-executable code which is used to calculate the filtered set of interest points 1020 from the set of interest points 1018. Within the computer memory 1014 there is a neighborhood-based filter 1036. The neighborhood-based filter 1036 contains computer executable code which was used to calculate the reduced set of interest points 1022 from the filtered set of interest points 1020. Within the computer memory 1014 there is a trained classification module 1038. The trained classification module 1038 contains computer-executable code which is used to calculate the classified set of interest points 1024 from the reduced set of interest points 1022. The computer memory 1014 further contains a second neighborhood-based filter 1040. The second neighborhood-based filter 1040 contains computer-executable code which is used to calculate the set of punctation locations 1026 from the classified set of interest points 1024. The control module 1030 or computer code is then used to calculate the punctation mark regions 1028 from the set of punctation locations 1026.

Cervical cancer is a predominant killer of women in the developing world. Its high mortality is primarily due to lack of awareness and lack of screening and diagnostic resources in these areas. Colposcopy is an essential step in diagnosis of cervical cancer at an early stage (precancerous lesions or micro-invasive cancers). It involves looking at cervix region and acquiring cervix images appropriately using a colposcope. Colposcopic examination is done in several steps including microscopic analysis without preparation, analysis after use of green filter, acetic acid and Lugol's iodine, and is a skilled process. A gynecologist examines each image or video carefully to collect all findings for cumulative scoring based on defined indices like Reid's index.

Colposcopy's interpretation is difficult and hence colposcopy has a high inter and intra operator variability; it is also estimated that to be perform it, a gynaecologist needs to have done at least 50 such examinations under supervision. Hence, it is crucial to have an automated system to detect abnormal features in images and give an accurate and objective colposcopy assessment. The punctation and mosaic patterns have heavy weight in computing the Reid's index.

Punctation appears when tips of the terminal vessels in the stroma reach the surface of the epithelium through stromal papillae. They appear as red dots in the acetowhite region. The punctation is classified in to two types: 1) Fine punctation 2) Coarse punctation. Fine punctation is indicative of normal or low grade region whereas coarse punctation indicates a high grade pre-cancerous lesion.

The punctation detection is one of the major components of automated colposcopy image analysis for diagnosing or screening cervical cancer. These features can present in groups or in isolation in the image. It is a challenging task due to overlapping and noisy factors like specular reflections, complex nature of the surface and mucus secretion. Another main challenge is the diversity in appearance of punctation marks at various stages on the colposcopy procedure. It is also their small size and intensity of punctation which makes it a challenging task A robust method to detect and segment punctation areas in colposcopic image acquired at various stages like pre-acetic acid, green filter, post-acetic acid images is described. The results of the approach may be used in at least two ways:

to assist a colposcopist in grading the lesion for improved diagnosis and to feed in to an automated colposcopy system.

Embodiments of the invention may overcome the following problems or disadvantages:

Detection of subtle punctation patterns. It guides colposcopist to zoom/magnify image appropriately based on subtle punctation detection.

The appearance of punctation marks at various stages on the colposcopy procedure. Embodiments of the invention may provide a method to detect and segment punctation areas in colposcopic image acquired at various stages like pre-acetic acid, green filter, post-acetic acid images.

Poor sensitivity and specificity of current methods are overcome by the present invention. Embodiments of the invention may provide a method to objectively detect the subtle punctation as well as it is robust to various confusing patterns like white glands, specular reflections, etc.

The lack of skilled resources. Embodiments of the invention may provide at least part of automated system helping to achieve easy interpretation of colposcopy findings.

Poor efficiency of the manual procedure. Embodiment of the invention may provide system with increased efficiency by automatic detection of punctation pattern.

The punctation patterns in colposcopy images are difficult to locate. Sometimes, because of their subtle nature they remain hidden from a doctor's eye. For example, the following case of a patient diagnosed as CIN2 illustrates it well.

Figure 11:
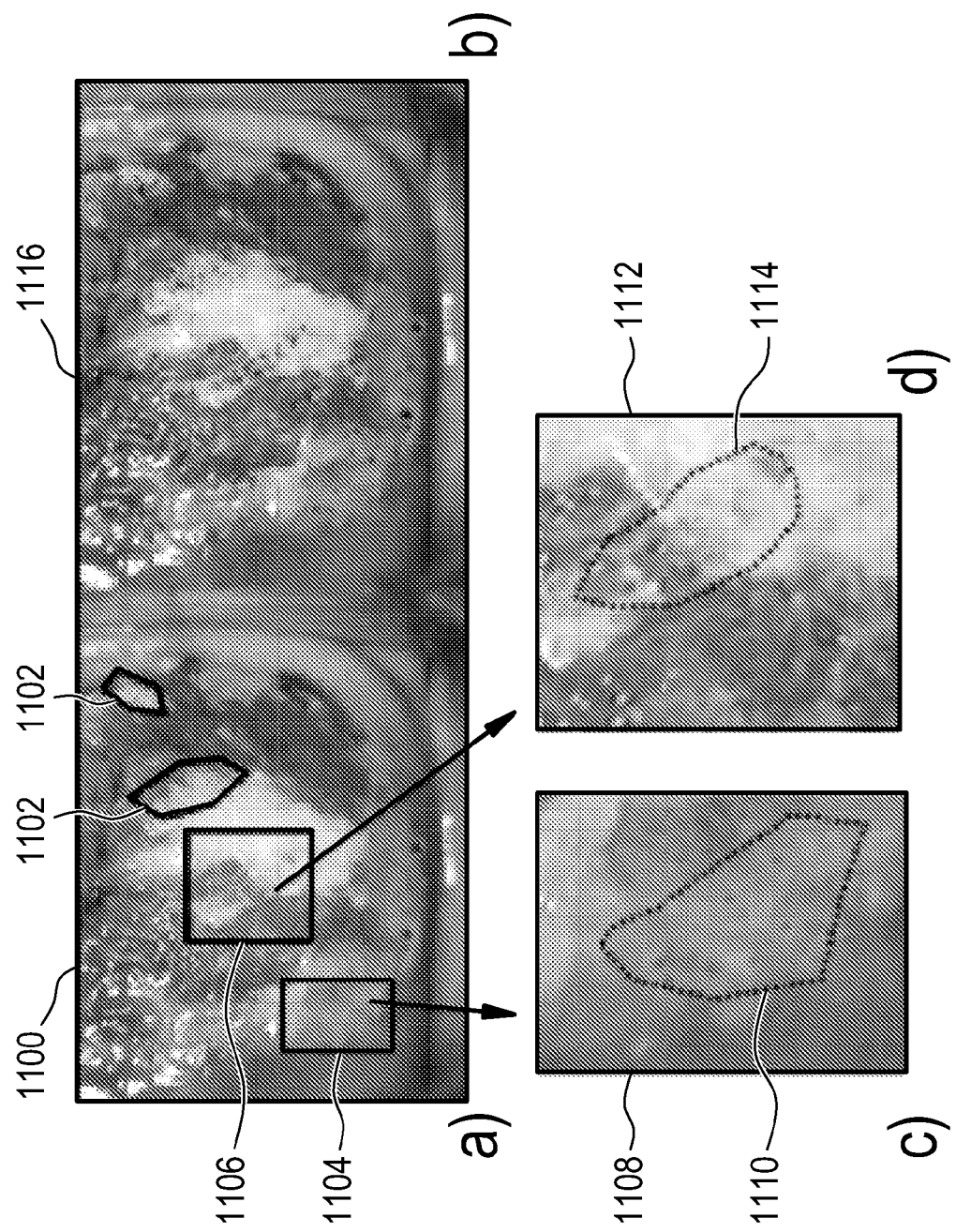
FIG. 11 shows a cervical image.

FIG. 11 shows a cervical image 1100. The regions marked 1102 show regions with easily located punctation points. Region 1104 and 1106 marked in image 1100 show regions with punctation marks that are not so easily visible. Image 1108 is a blowup zoom-in of region 1104. A punctation region 1110 is shown within image 1108. Image 1112 is a zoom-in of region 1106. Within image 1112 there is a punctation region marked 1114. Image 1116 shows image 1100 with punctation points emphasized.

FIG. 11 illustrates the subtle nature of punctation patterns: image 1100 Shows original image with enclosed 'easy to perceive' punctation marks, image 1116 Shows detected punctation marks, and images 1108 and 1112 show zoomed regions of hard to detect, with naked eye, punctation patterns with highlighted punctation regions.

FIG. 11 illustrates the need of a system to detect those subtle punctation patterns to identify the pre-cancerous cases. Other alternative to detect these patterns is to zoom in the colposcope to take images of different regions, which involves more colposcopist time, makes the process less efficient.

Hence, embodiments of the invention may make the colposcopy image analysis more efficient and accurate to detect the subtle punctation patterns.

Other disadvantage of current manual practice is the subjectivity of the process. Generally, colposcopist need to give a score for various abnormal features based on their presence/absence, granularity and other criteria. It is evident that there are chances to miss the features or to err in identifying them. Embodiments of the invention may overcome this human subjectivity by automatic interpretation of punctation patterns.

Embodiments of the invention may have the following features:

A punctation detection module which is inbuilt into a video colposcope;

A punctation detection module that sits in between the video capture module and the visual display module of the colposcope;

A punctation detection module that is based on the idea of using corner detection followed by multiple rejection steps involving heuristics based on local analysis and neighborhood punctation point's credibility to discriminate between correct punctation and false ones;

A punctation detection module that has two major stages for detecting punctation robustly; (a crude level and fine level). It filters the false positives like white glands, and specular reflections etc.

A punctation detection module that has two more components to detect isolated punctations and punctations in a group;

A punctation detection module detecting punctation in different colposcopy images viz a viz pre-acetic, post-acetic, green-filter, and zoomed/magnified images;

A punctation detection module that highlights the region in the cervix where punctations are present.

A detailed block diagram of the punctation detection module is shown in FIG. 12. FIG. 12 shows the relationship of several software modules within an embodiment of the invention. Module 1200 is a video capture module which captures video from a colposcope. This then passes data to a punctation detection module 1201. The punctation detection module 1201 then passes data to a video display of colposcope 1202. The colposcopy images may be pre-processed (1300) as it can contain the following regions:

shiny/whitish regions which can be the result of specular reflections or acetowhitening;
blood regions, which are exceptionally red or dark red;
very dark regions because of cervical OS;
external objects and neighborhood regions of cervix;
cervix region of Interest masking.

For the diagnosis of cervical cancer it may be beneficial to find punctation in cervix region, hence input to our system is the segmented cervix region. The mask image is computed containing all true or searchable regions. This helps in getting rid from external objects problem.

Crude level Punctation Detection (steps 1308) may consists of several steps of detecting punctation marks and gives reasonable detection accuracy with good sensitivity and medium specificity. The accuracy is further enhanced in fine level punctation detection.

Figure 7A:
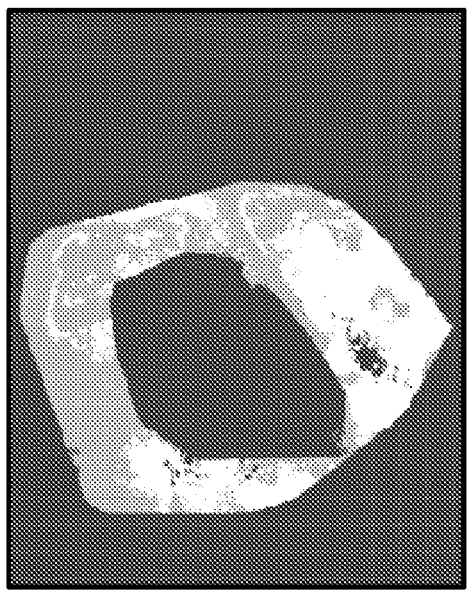
FIG. 7a shows the transformation zone in post-acetic acid image.
Figure 7B:
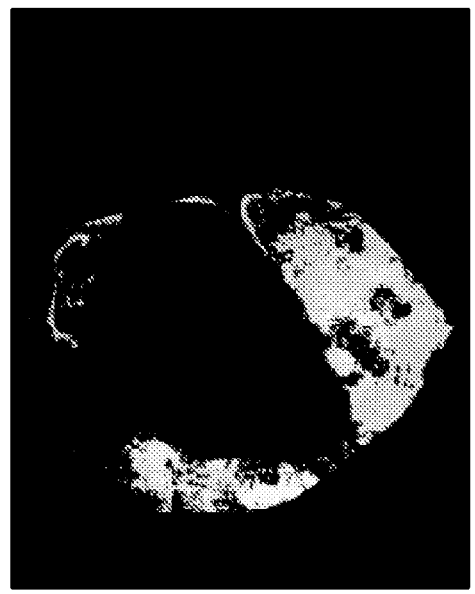
FIG. 7b shows the clustering transformation zone to dominant and minor opacity changes.
Figure 7C:
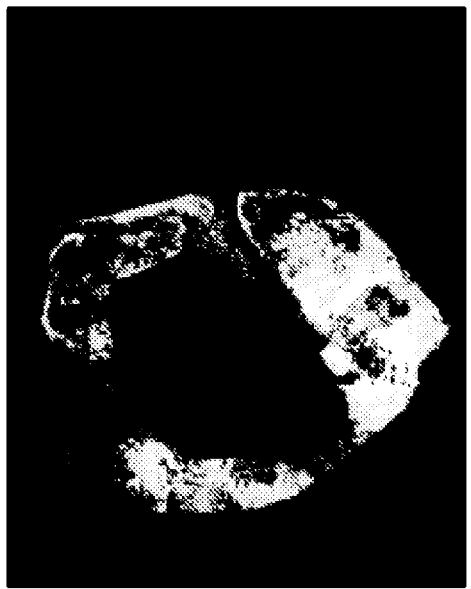
FIG. 7c shows pixels in post-acetic transformation zone with dominant opacity changes.
Figure 7D:
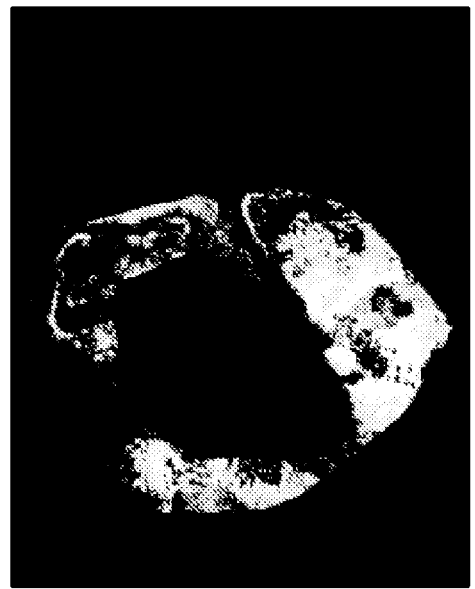
FIG. 7d shows corresponding pixels in pre-acetic acid image.
Figure 8A:
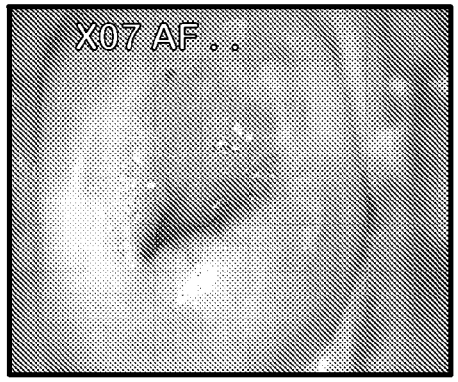
FIG. 8a shows a pre-acetic acid image.
Figure 8D:
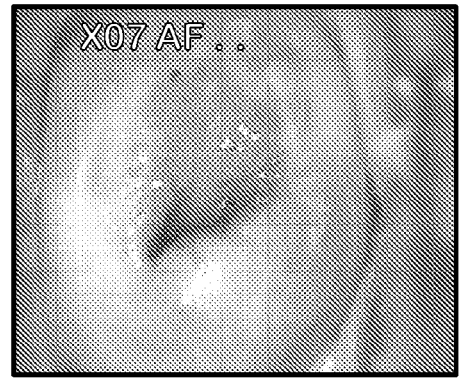
FIG. 8d shows a pre-acetic acid image.
Figure 8B:
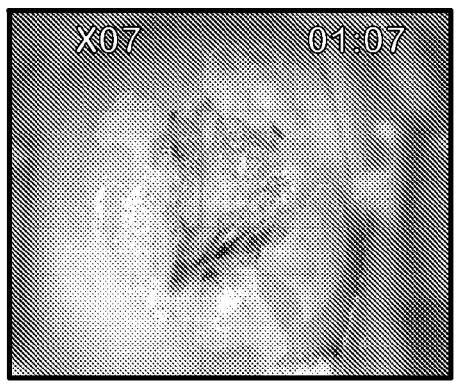
FIG. 8b shows a post-acetic acid image after 1 min.
Figure 8E:
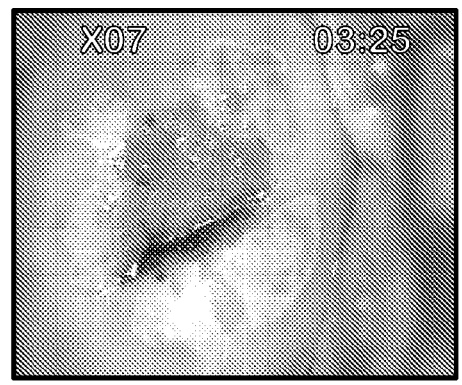
FIG. 8e shows a post-acetic acid image after 3 min.
Figure 8C:
FIG. 8c shows a opacity image with opacity difference score=18.46.
Figure 8F:
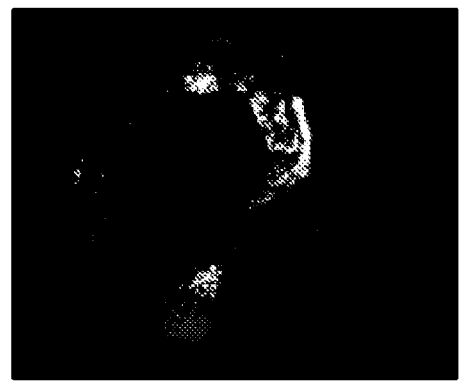
FIG. 8f shows an opacity image with opacity difference score of 43.28.

Interest Point (IP) detection (step 1302) may be used to detect initial crude level punctation estimate. A Harris corner detector may also be used. The IPs on the mask image may be computed in the last step. It is very sensitive but have poor specificity related to punctation detection i.e. many IPs are detected which are false punctation. 1022 IPs are shown in FIG. 7b. These IPs are labeled as SET1.

Morphological Operations based filtration: The set of interest points detected may be refined in last step by applying morphological heuristics. There are many points, peaks, lines etc. which are detected in the last step. One important cue we used is the dark nature of punctation with respect to background and its point like nature. The images are put into a binary form to look for the IP being dark/bright, its orientation and aspect ratio etc. This step gives a lot of reduction from 1022 to 384 points. We call filtered points as SET2.

Neighborhood punctation authenticity based filtration: It was observed that mostly punctation appears in group. The points present in SET1 may or may not be present in SET2. Below is the method step-by-step:

a) Select a point 'y' in SET2;
b) The points in the neighborhood ('N(y)') of point 'y' are analyzed and checked how many of them are present in SET1 and not in SET2, this number is called NF, number of false points;
c) Similarly, for point 'y' in SET2, neighborhood points ('N(y)') are analyzed in SET1 and checked how many of them are present in SET1 and in SET2, these are called $N_C$, number of correct points;
d) If $N_F \gg N_c$, the selected point in SET2 is filtered;
e) This procedure is repeated for all points in SET2. It is detailed in equations below:

$$N_c = \sum_{x \in N(y)} (x \in SET1 \ \& x \in SET2)$$

$$N_f = \sum_{\infty \in N(y)} (x \in SET1 \ \& \ | \ (x \in SET2)).$$

This step removes falsely detected punctation near specular reflections/corners etc. This step gives around 50% reduction from 384 to 185 points.

The crude level punctation detection step gives us very likely candidates for punctation marks. However, clinically there is still much false detection such as white glands, white rings, points on the boundaries etc. All of them are strong similarities to true punctation marks. It is not possible to filter them with any classical heuristic based approach, which is mostly affected by noise and robust. Hence, a learning based framework was deployed fine level Punctation Detection (steps 1314). Randomized trees were randomized to train with sufficiently large number of examples containing true and false punctation examples.

1.) Randomized Trees: The RT (Randomized trees) are built with bagging approach and each RT is trained with randomly selected features.

a. Training: The training and construction of classifier in shown in FIG. 13. 3000 samples were collected from 25 datasets. An optimal set of trees were found by checking the test error rate with increase in number of trees.

b. Testing: To test a sample, a feature vector was used to test it using all RTs. Each RT is given a vote, and the consensus is assigned to the candidate. The average of these votes was computed as probabilistic measure of a point being a true punctation mark. This measure is called strength of the given candidate. The points showing low strength were filtered. This step gives a reduction from 185 points (crudely detected) to 145 points.

2.) Isolated Punctation detection and filtering: As known and mentioned that punctation has relevance more when it occurs in groups. This final step eliminates the false punctation by detecting if it is in isolation and if the strength is low. As after several refinement stages, few false positives left which are in isolation. Hence, this step gets rid of many of the remnants of false detected punctations. This step gives a reduction from 145 points to 45 points.

3.) Punctation Grouping and region demarcation: The final set of detected punctation points is grouped together using an image closing operation to form punctation regions.

The detailed flowchart containing main elements is shown in FIG. 12. In the following figures, the construction of a RT (Randomized tree) is illustrated and how to select optimal number of trees.

FIG. 13 shows a flow diagram which illustrates a method according to an embodiment of the invention. First in step 1300 there is pre-processing of the image. Next in step 1302 interest point detection is performed. Next in step 1304 initial filtering based on morphological heuristics is performed. Next in step 1306 filtering based on punctation of authenticity is performed. Steps 1302, 1304, and 1306 are considered to be crude level punctation detection 1308. Next step 1310 is performed. In step 1310 a RT classifier is used to classify punctation marks. Next in step 1312 isolated punctation marks are filtered. Steps 1310 and 1312 are considered to be fine-level punctation detection 1314. In step 1316 the punctation marks are grouped to form punctation regions and the results are saved.

Figure 14:
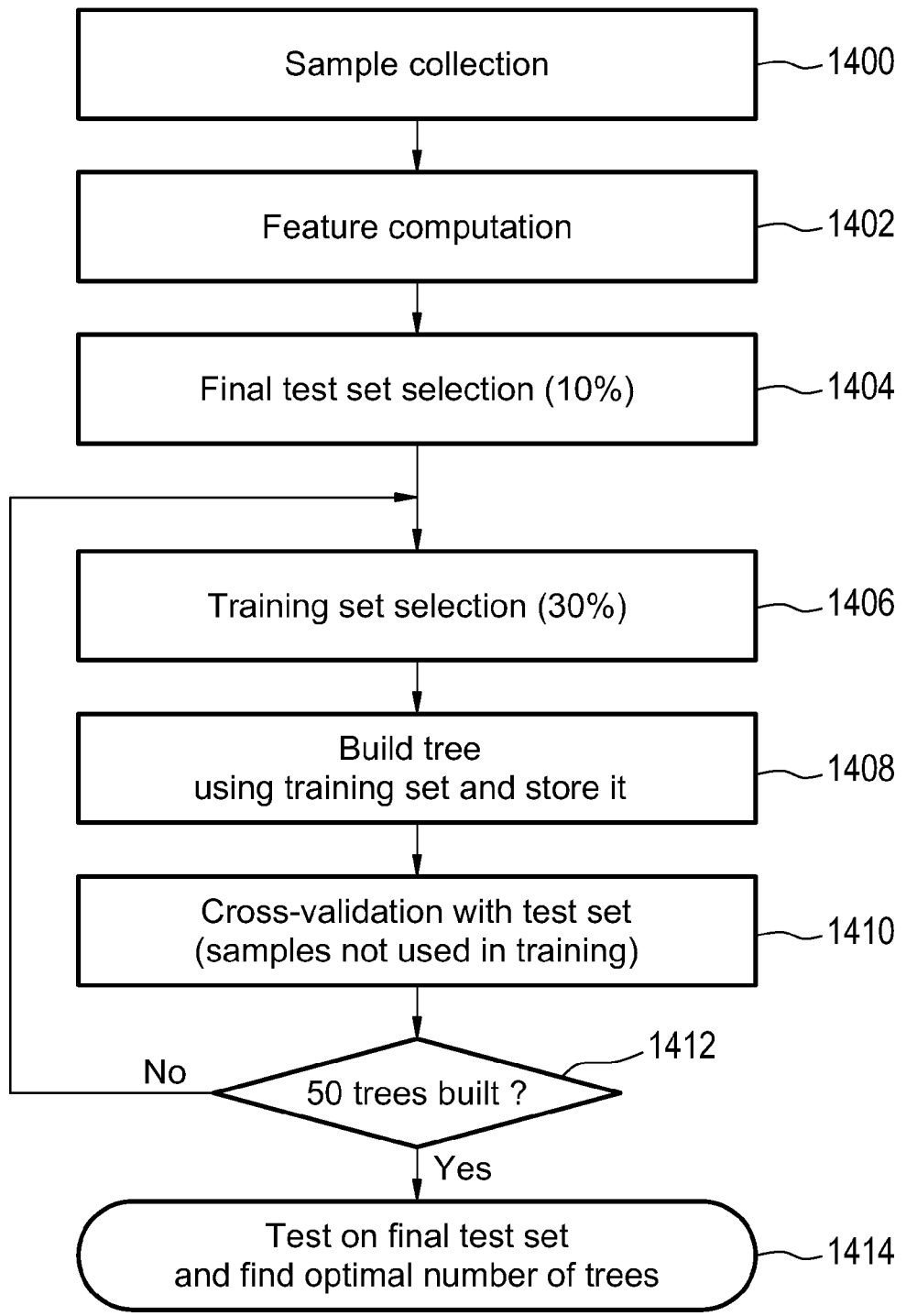
FIG. 14 shows an example of how to build an RT or randomized tree which is used as the trained classification module.

FIG. 14 shows an example of how to build an RT or randomized tree which is used as the trained classification module. First in step 1400 sample collection is performed. Next in step 1402 feature computation is performed. In step 1404 10% of the sample is withheld from performing the testing on. Next in step 1406 a training set selection is selected. The random selection is used to induce independence in trees. Twenty-five percent of all features are chosen randomly and used to build each tree. Next in step 1408 a tree is constructed using the training set and is stored. Next in step 1410 cross-validation is performed with the test set. These are the sets of data that were not used in training. Step 1412 is a decision box with the question: have 50 trees been built? If the answer is no then the method returns to step 1406 and steps 1406, 1408, and 1410 are repeated until 50 trees have been built. If 50 trees have been built, a test is performed.

Figure 15:
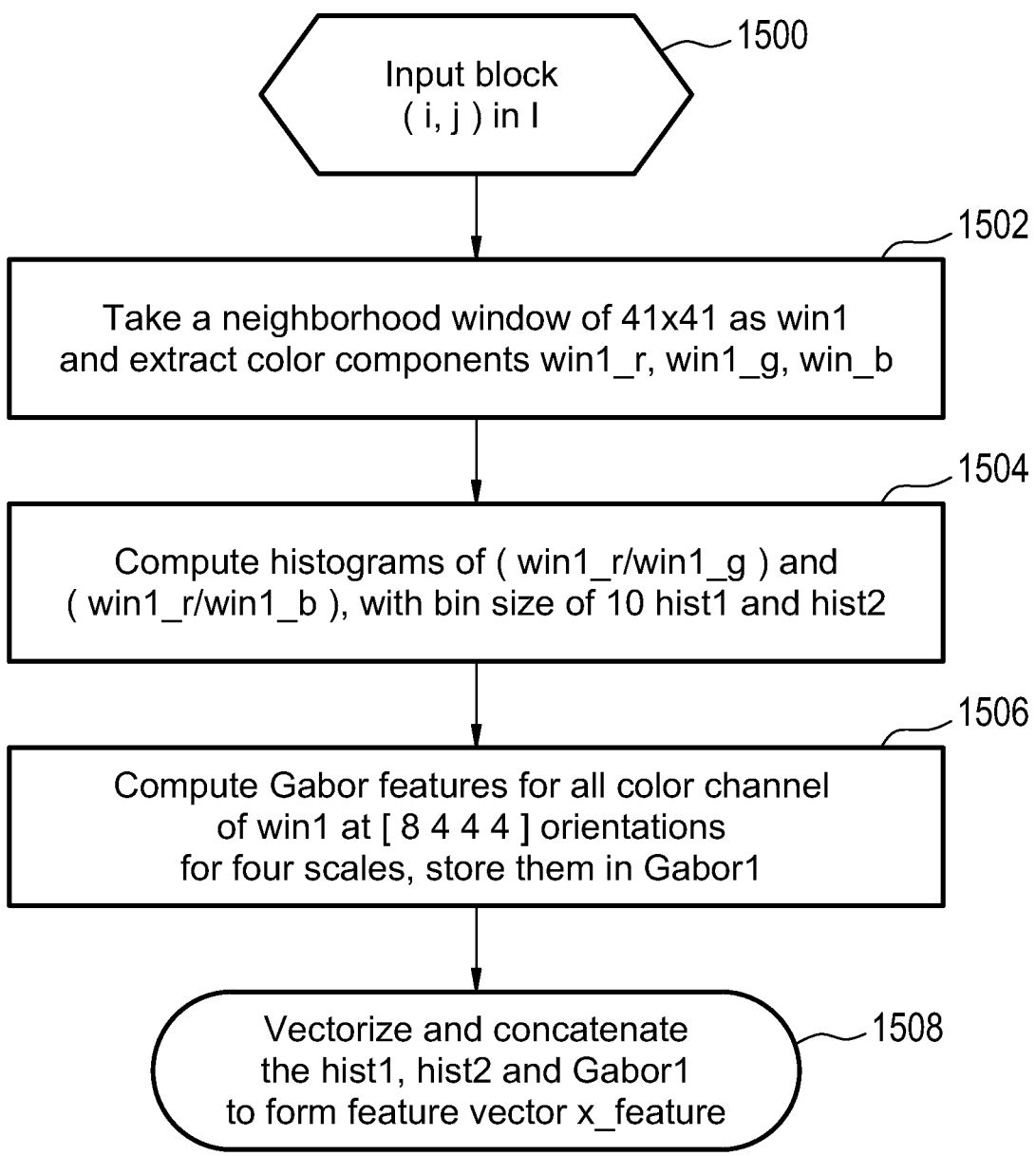
FIG. 15 shows a flow diagram which shows feature computation for building randomized tree classifiers.

FIG. 15 shows a flow diagram which shows feature computation for building randomized tree classifiers. In step 1500 an input block is taken. Next in step 1502 a neighborhood window of 41×41 pixels is examined. A window of 41×41 pixels was found to be the optimal size experimentally. Next in step 1504 histograms of the colored pixels are computed. Punctation marks are red dots, so the histogram of the color red is a useful for identifying punctation marks. Histogram ratios make the method more robust with respect to intensity variations. Next in step 1506 the Gabor features are computed for all color channels of the window. Gabor features are strong contenders for capturing the frequency domain characteristics of the image. As punctation has a sharp change in intensity it will have a specific Fourier domain nature or signature. The Fourier scales are used for each orientation. This is a total of 20 features for each color channel. Finally in step 1508 the histograms and the Gabor features are vectorized and form a feature vector.

Figure 16:
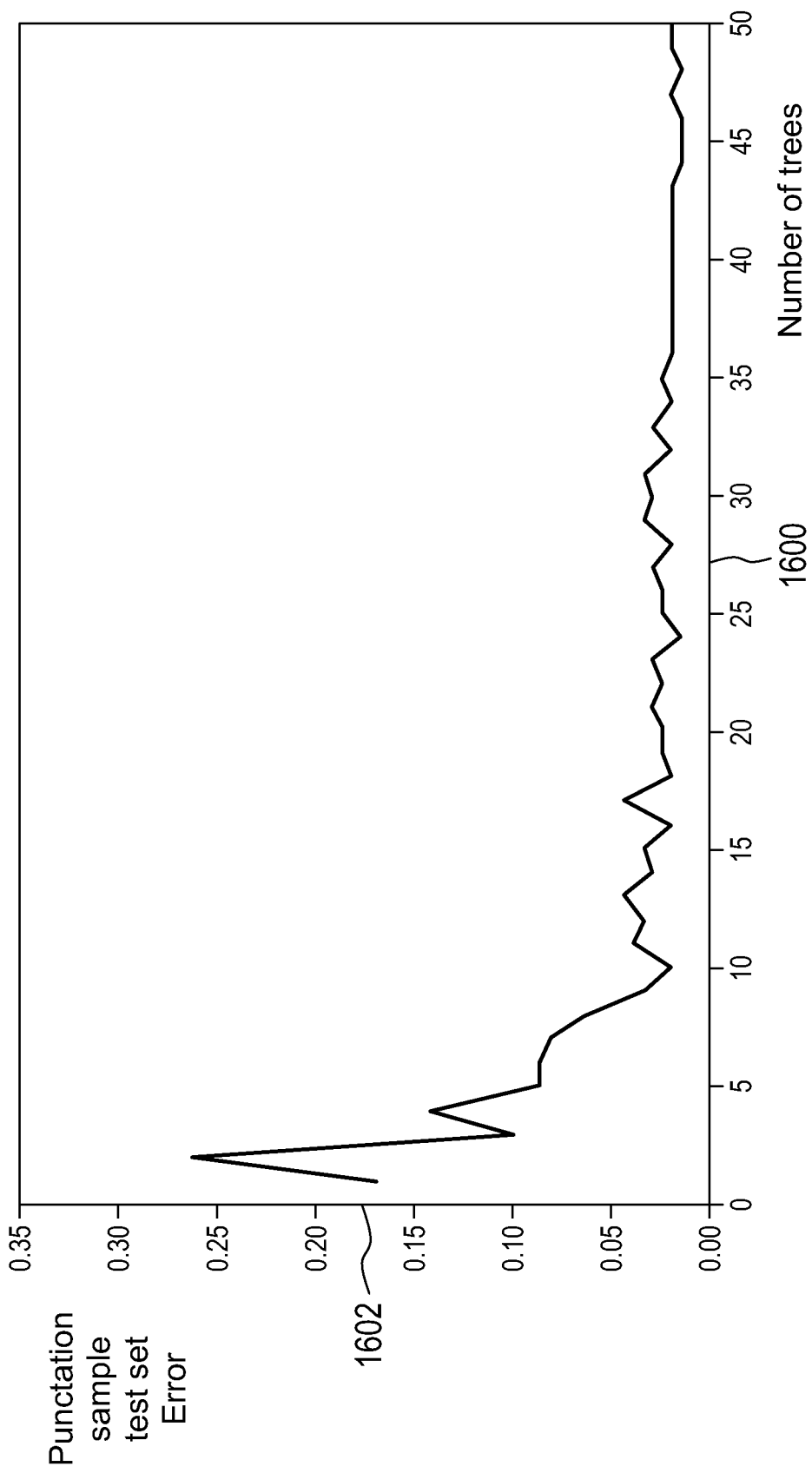
FIG. 16 shows a plot of the number of trees versus the punctation sample test
   set error.

FIG. 16 shows a plot of the number of trees 1600 versus the punctation sample test set error 1602. The test set error shown in FIG. 16 shows that one foreign 8% error or 98.2% accuracy is achieved with ten trees. This figure illustrates that the use of ten trees is sufficient for accurate punctation detection.

FIG. 16 shows an example image to illustrate the flow of a punctation detection system. Punctations in the endo-cervical region are visible as black dots. These are highlighted by black circles.

Figure 17:
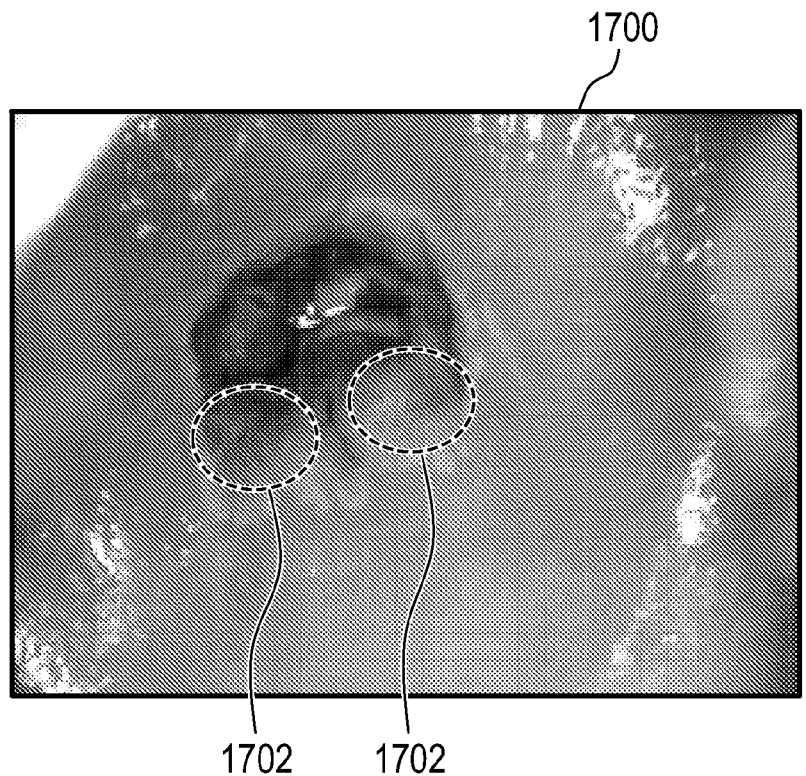
FIG. 17 shows a cervical image.

FIG. 17 shows a cervical image 1700. Within the cervical image 1700 are two regions 1702 with punctation. The filtered points in next step are highlighted in black circles.

An embodiment of the invention has been tested using 35 datasets with many intra-variations. The classifier was trained and it achieved a testing accuracy of 98.2% in comparison to an expert.

The punctation marks can be present in CIN1, CIN2 and CIN3 cases. It can also be present in endo-cervical regions as well as ecto-cervical regions. Some exemplary results are shown below with remarks.

Figure 18:
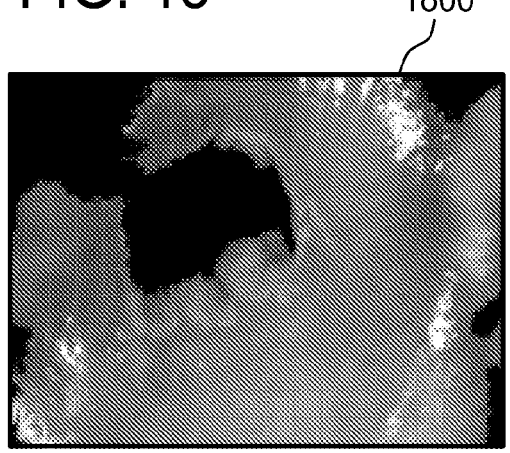
FIG. 18 shows image 1700 after pre-processing.

FIG. 18 shows image 1700 after pre-processing 1800.

Figure 19:
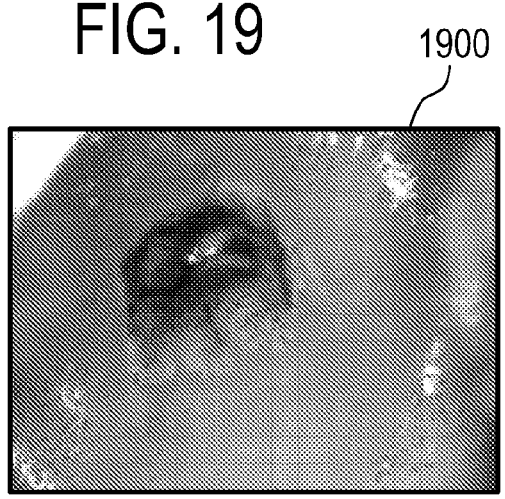
FIG. 19 shows image 1700 showing detected interest points located in image 1800.

FIG. 19 shows image 1700 showing detected interest points 1900 located in image 1800. All point like objects have been detected, total points=1022

FIG. 20 shows image 1900 after morphological filtering 2000. This figure shows an output after morphological filtering of points detected in last step, number of points=384.

FIG. 21 shows image 2000 after neighborhood filtering 2100. The output after applying the neighborhood authenticity method, number of points=183.

FIG. 22 shows image 2100 after using an RT classifier. Region of interest 2202 is marked in image 2200. The region 2302 is shown in a zoom image 2204. Output after classifying each point with Randomized trees, number of points=183.

FIG. 23 shows image 2200 after using a second neighborhood filter. Isolated punctation detection and filtering based on RT output, number of points=45. Region of interest 2302 is shown within image 2300. Image 2304 is a zoom of region 2302.

Figure 24:
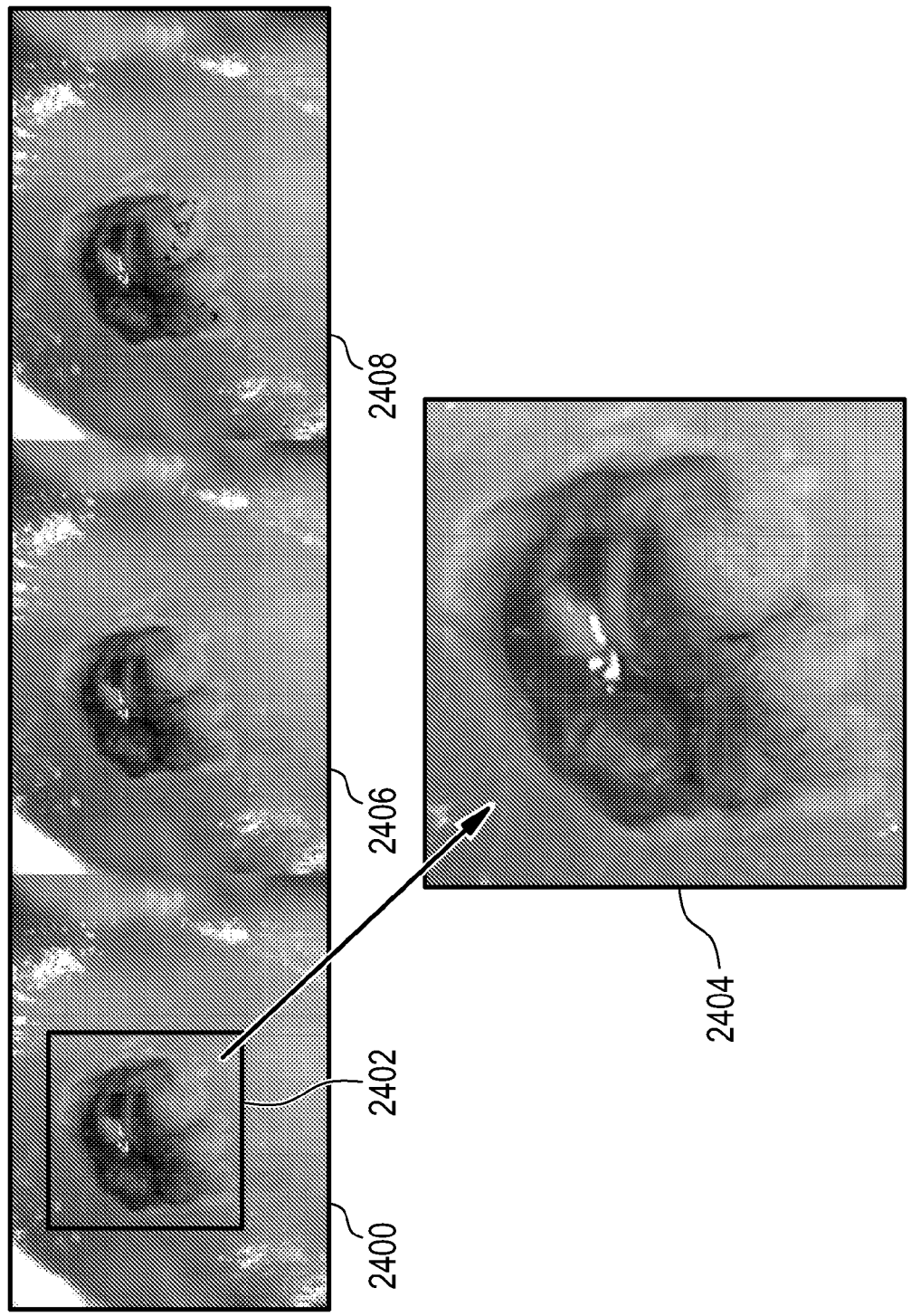
FIG. 24 shows punctation found in an endo-cervical region.

FIG. 24 shows punctation found in an endo-cervical region. A cervical image 2400 is shown. There is a region of interest 2402 marked in image 2400. The region of interest 2402 is zoomed-in or blown up and shown in image 2404. Image 2406 shows image 2400 with punctation locations. Image 2408 shows image 2400 with punctation regions.

Figure 25:
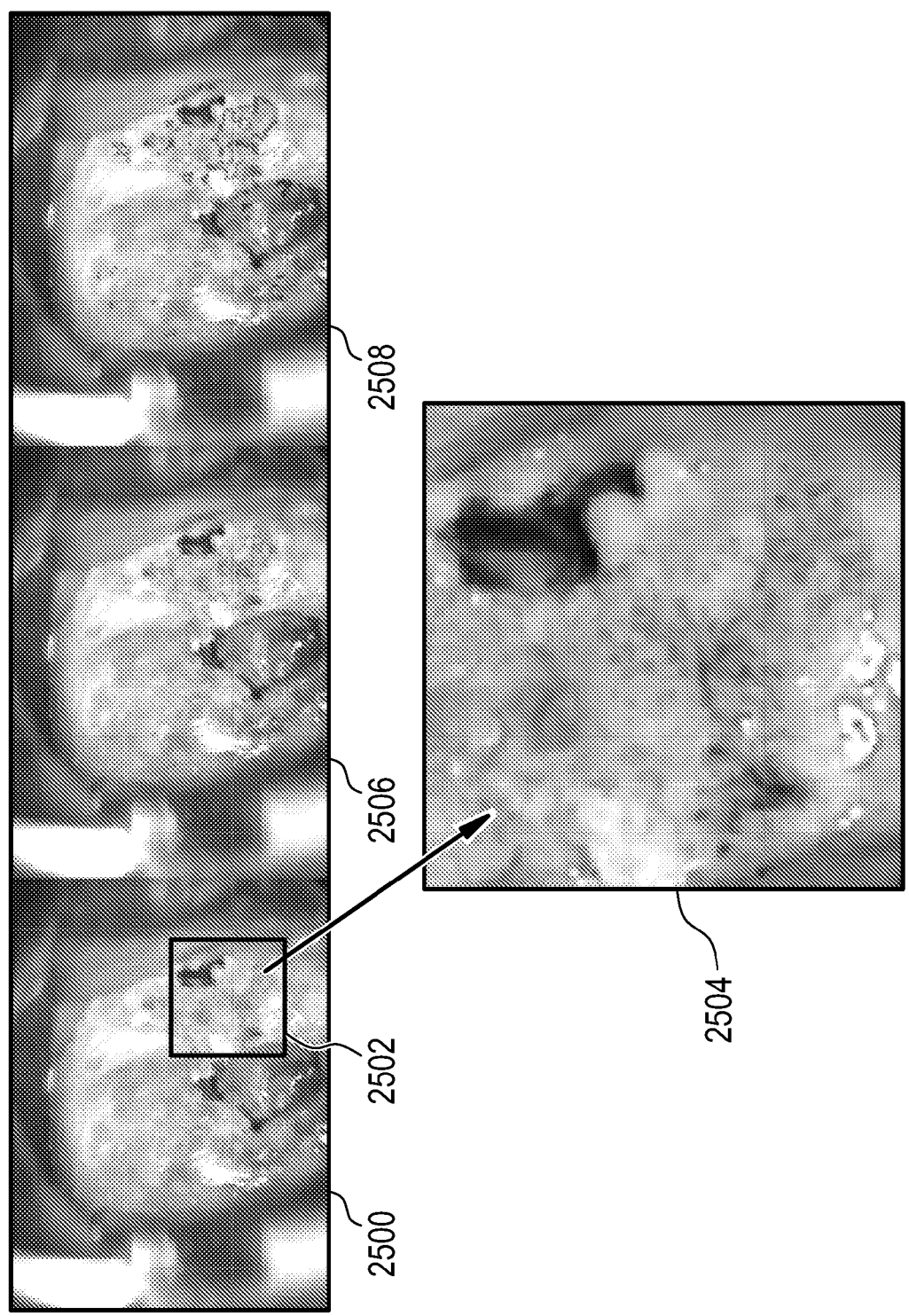
FIG. 25 shows a green filter image of a cervix with highlighted punctation.

FIG. 25 shows a green filter image with highlighted punctation. Image 2500 is a cervical image. Within image 2500 there is a region of interest 2502 marked. The image 2504 shows a zoom-in of the region 2502. Image 2506 shows image 2500 with punctation locations. Image 2508 shows image 2500 with punctation regions.

Figure 26:
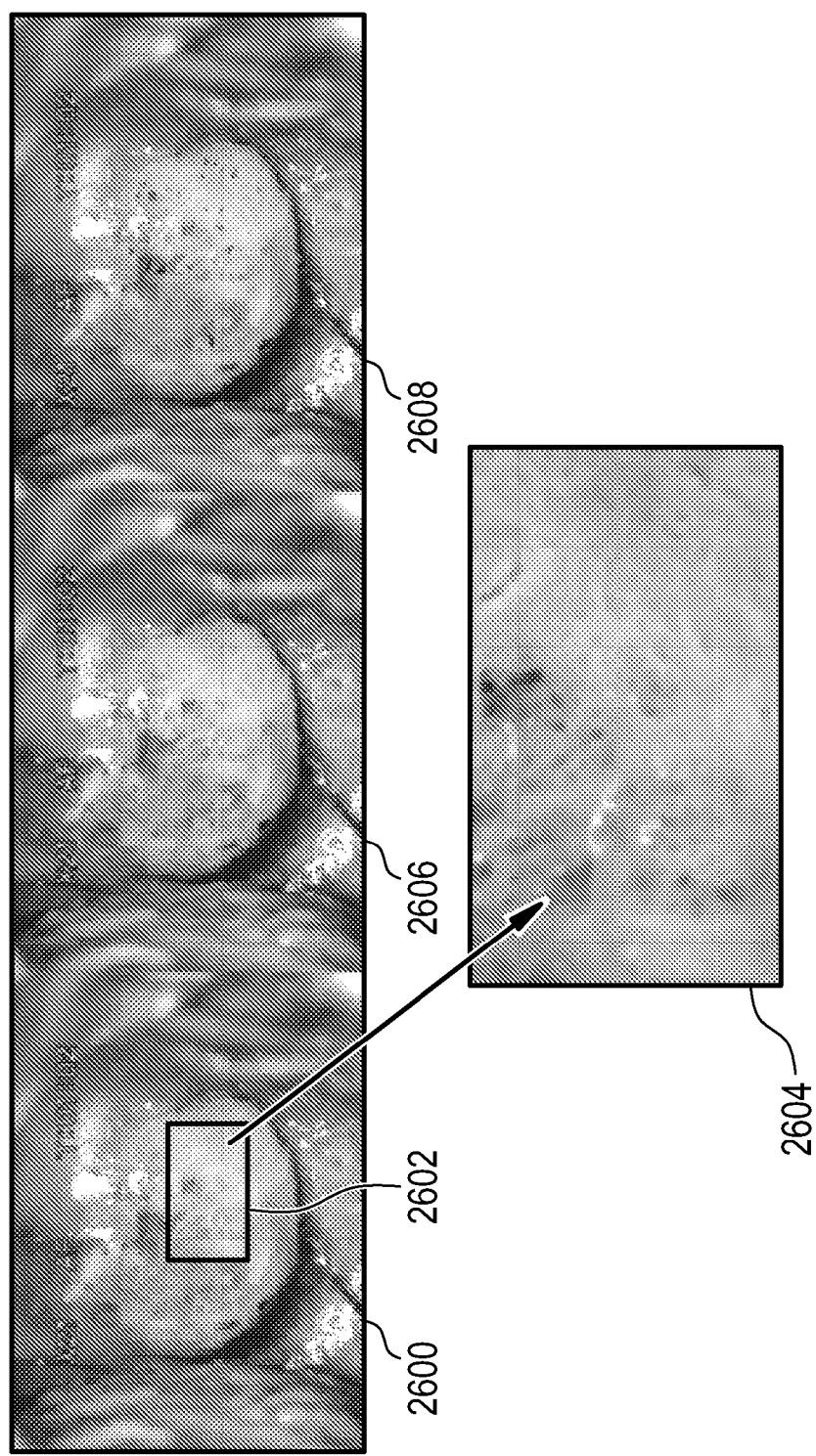
FIG. 26 shows a post-acetic acid image of a cervix with subtle punctation.

FIG. 26 shows a post-acetic acid image with subtle punctation. Image 2600 is a cervical image. Within image 2600 there is a region of interest 2602 marked. Image 2604 is a zoomed image of region 2602. Image 2606 is image 2600 with punctation locations. Image 2608 is image 2600 with punctation regions.

Figure 27:
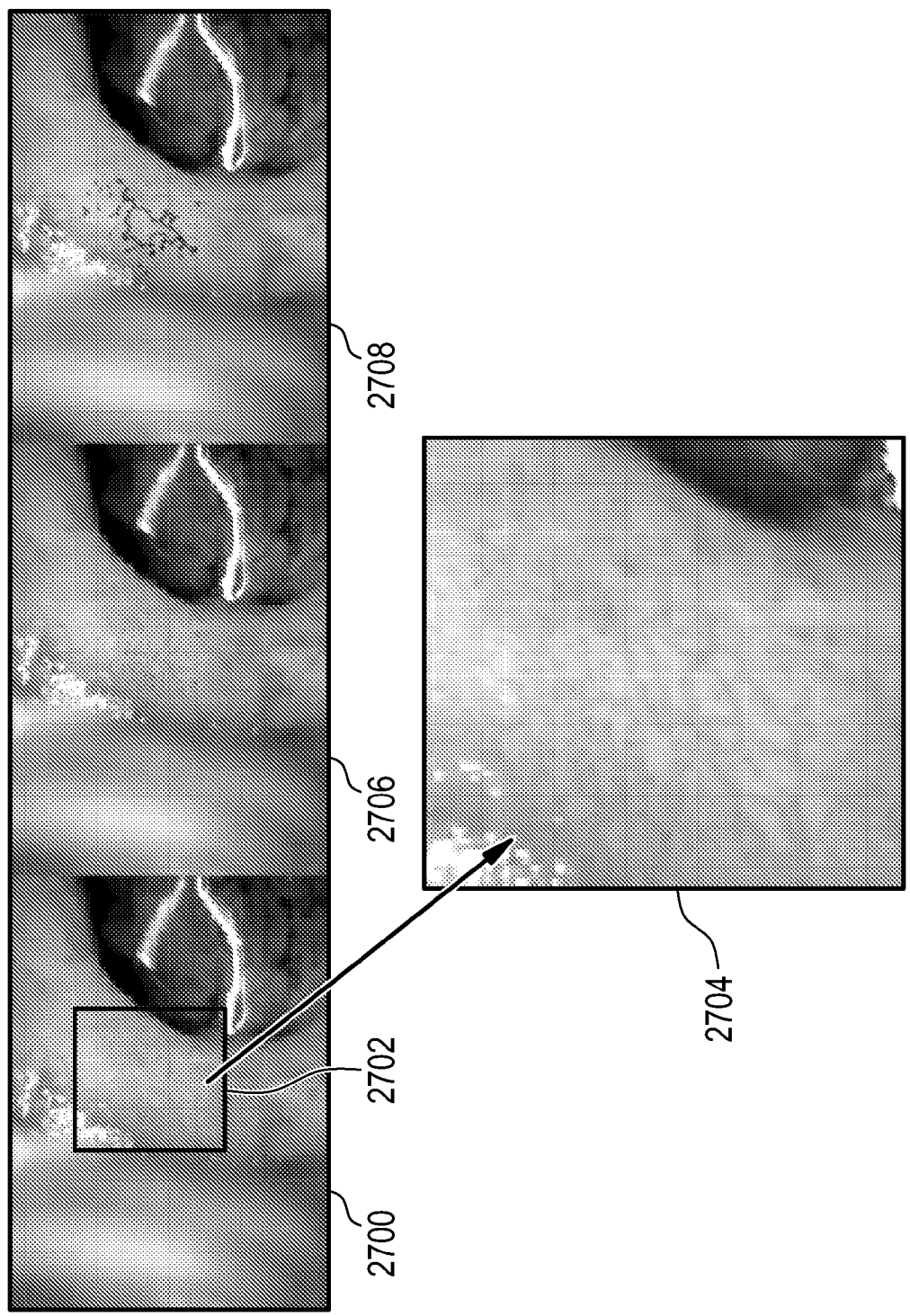
FIG. 27 shows a zoomed image of a cervix with low-strength punctation.

FIG. 27 shows a zoomed image with low-strength punctation. Image 2700 is a cervical image that has been zoomed. 2702 is a region of interest marked in image 2700. Image 2704 is a zoom of the region of interest 2702. Image 2706 is image 2700 with punctation locations. Image 2708 is image 2700 with punctation regions.

Figure 28:
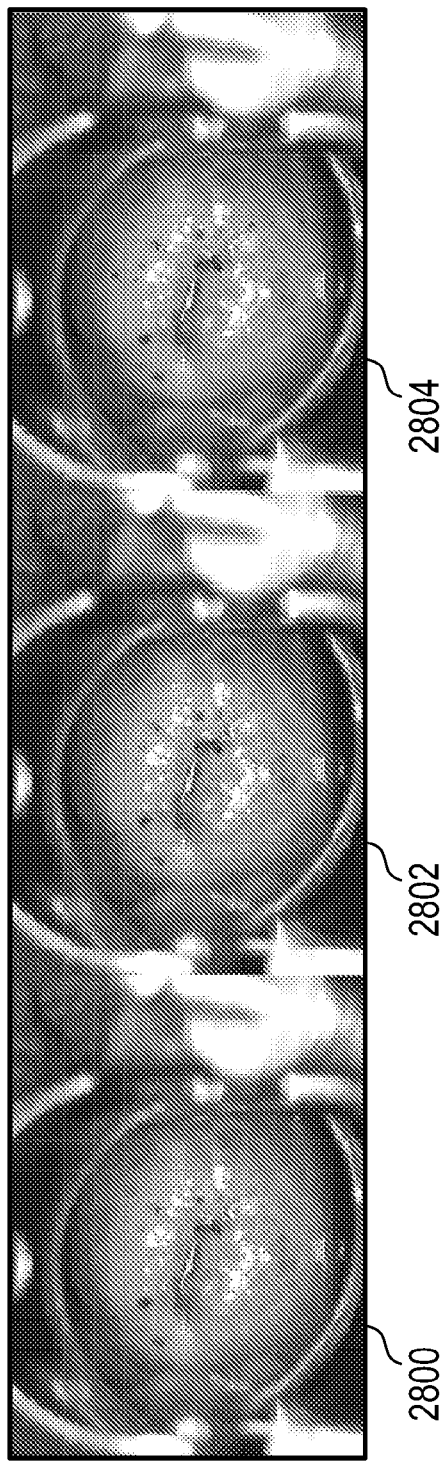
FIG. 28 shows a cervical image with inflammation and no punctation present.

FIG. 28 shows a cervical image 2800 with inflammation and no punctation present. Image 2802 is image 2800 with punctation locations. Image 2804 is image 2800 with punctation regions marked. It should be noticed that there are no punctation locations or regions visible in images 2802 and 2804.

Figure 29:
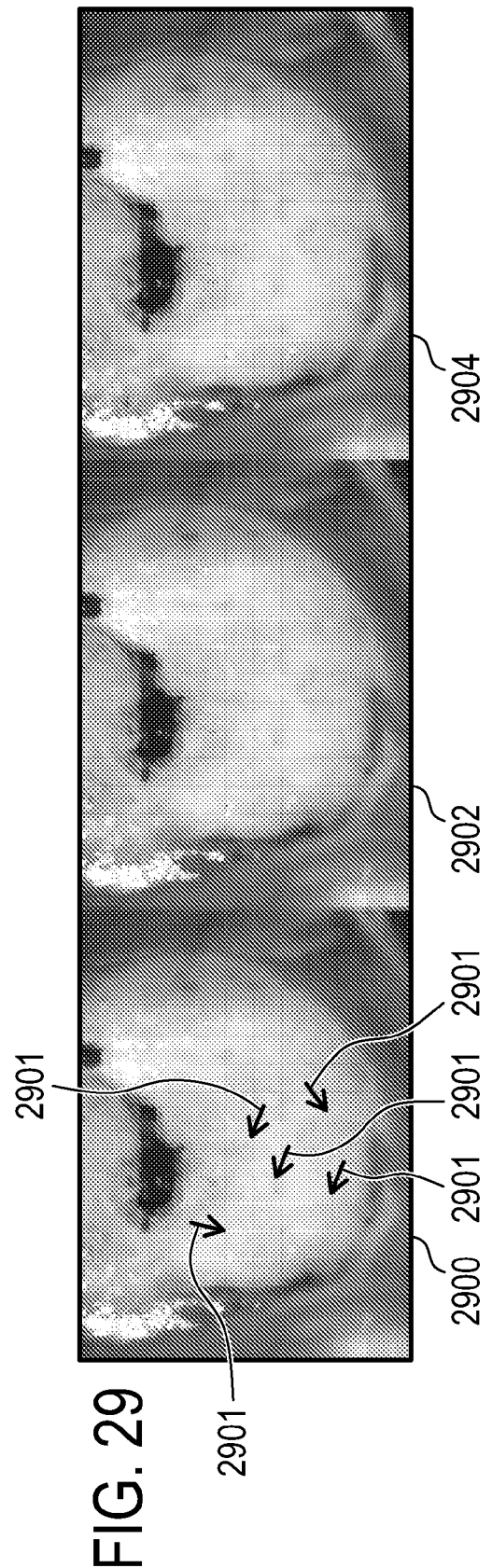
FIG. 29 shows a post-acetic acid cervical image with many white glands similar to punctation in the cervical region present.

FIG. 29 shows a post-acetic acid image with many white glands similar to punctation in the cervical region present. Image 2900 shows the original cervical image. The arrows 2901 show the location of white glands. Image 2902 is image 2900 with punctation locations. Image 2904 is image 2900 with punctation regions. It should be noted that punctation locations and regions are not visible on images 2902 and 2904.

Figure 30:
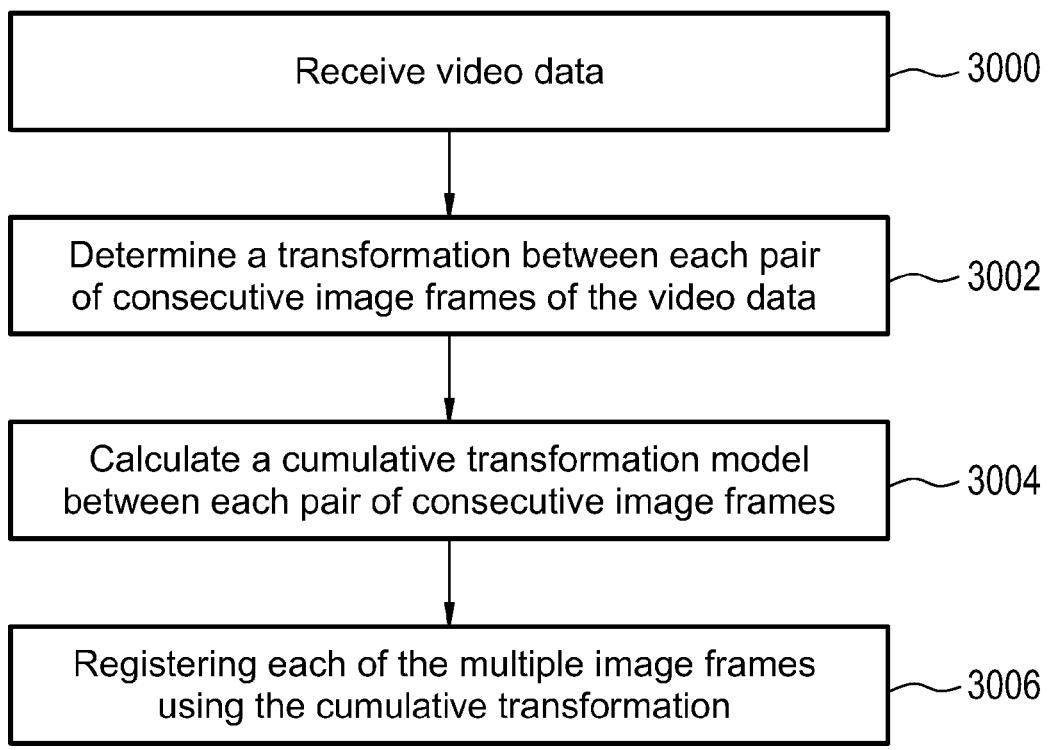
FIG. 30 shows a flow diagram illustrating a method according to a further embodiment of the invention.

FIG. 30 shows a flow diagram illustrating a method according to an embodiment of the invention. In step 3000 video data comprising multiple image frames is received. In step 3002 a transformation between each pair of consecutive image frames selected from the multiple image frames is determined. Next in step 3004 a cumulative transformation model is calculated from the transformation between each pair of consecutive image frames. Finally in step 3006 each of the multiple image frames are registered using the cumulative transformation.

Figure 31:
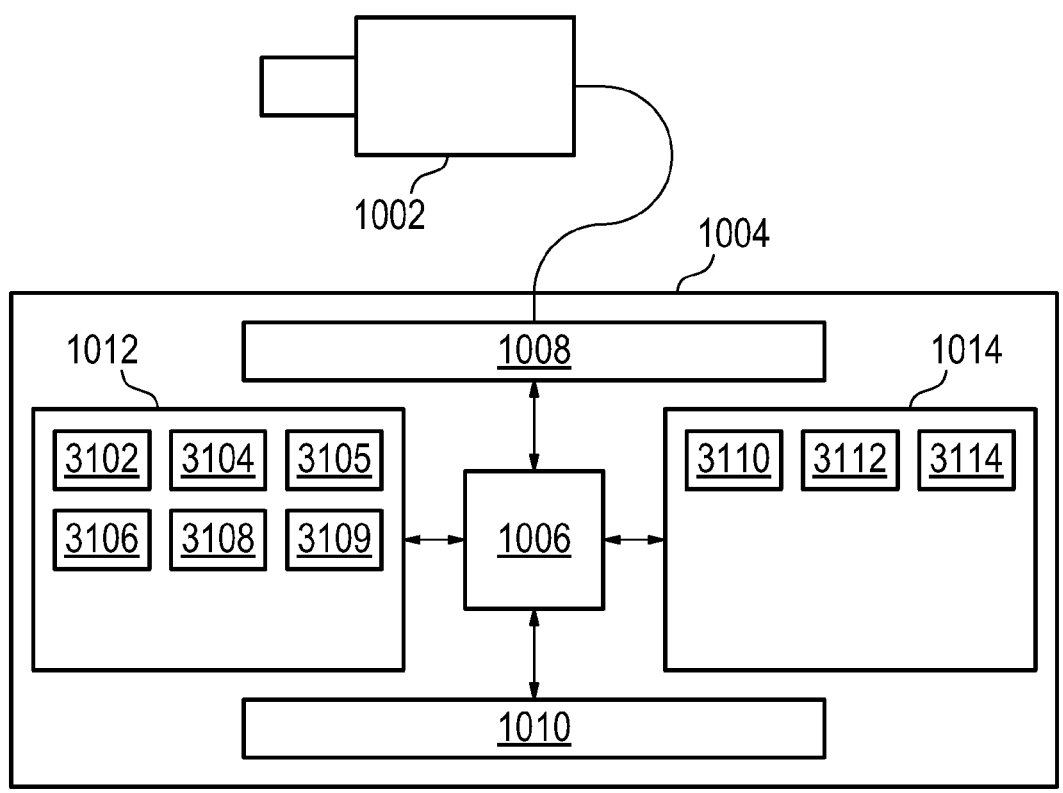
FIG. 31 shows an example of a medical instrument according to an embodiment of the invention.

FIG. 31 shows an example of a medical instrument 3100 according to an embodiment of the invention. It should be noted that the features of the embodiment shown in FIG. 31 may be combined with the features shown in FIG. 10. In particular the features shown in FIG. 31 may be useful for registering multiple images acquired during the course of an examination. These may be at the same magnification or they may even be between zoomed images.

The functioning of the computer 1004 and the optical examination system 1002 are equivalent to that shown in FIG. 10. The computer storage 1012 is shown as containing video data 3102 acquired with the optical imaging system 1002. The computer storage 1012 is further shown as containing a set of transformations 3104 calculated between frames of the video data 3102. The computer storage 1012 is further shown as containing a cumulative transformation 3105 calculated from the set of transformations 3104. The cumulative transformation 3105 is between a first image 3106 and a second image 3108 which are both also shown as being stored in the computer storage 1012. The first image 3106 and the second image 3108 are selected from the video data 3102. The computer storage 1012 is further shown as containing a registration of the first 3106 and second 3108 image that has been calculated from the cumulative transformation 3105.

The computer memory 1014 is shown as containing an image transformation module 3110. The image transformation module 3110 is used to calculate the set of transformations 3104 between adjacent frames of the video data 3102. The computer memory 1014 is shown as containing a cumulative transformation calculation module 3112 that was used to calculate the cumulative transformation 3105 from the set of transformations 3104. The computer memory 1014 is further shown as containing an image registration module 3114. The image registration module 3114 contains computer-executable code which was used to calculate the registration 3109 between the first image 3106 and the second image 3108 using the cumulative transformation 3105.

Figure 1:
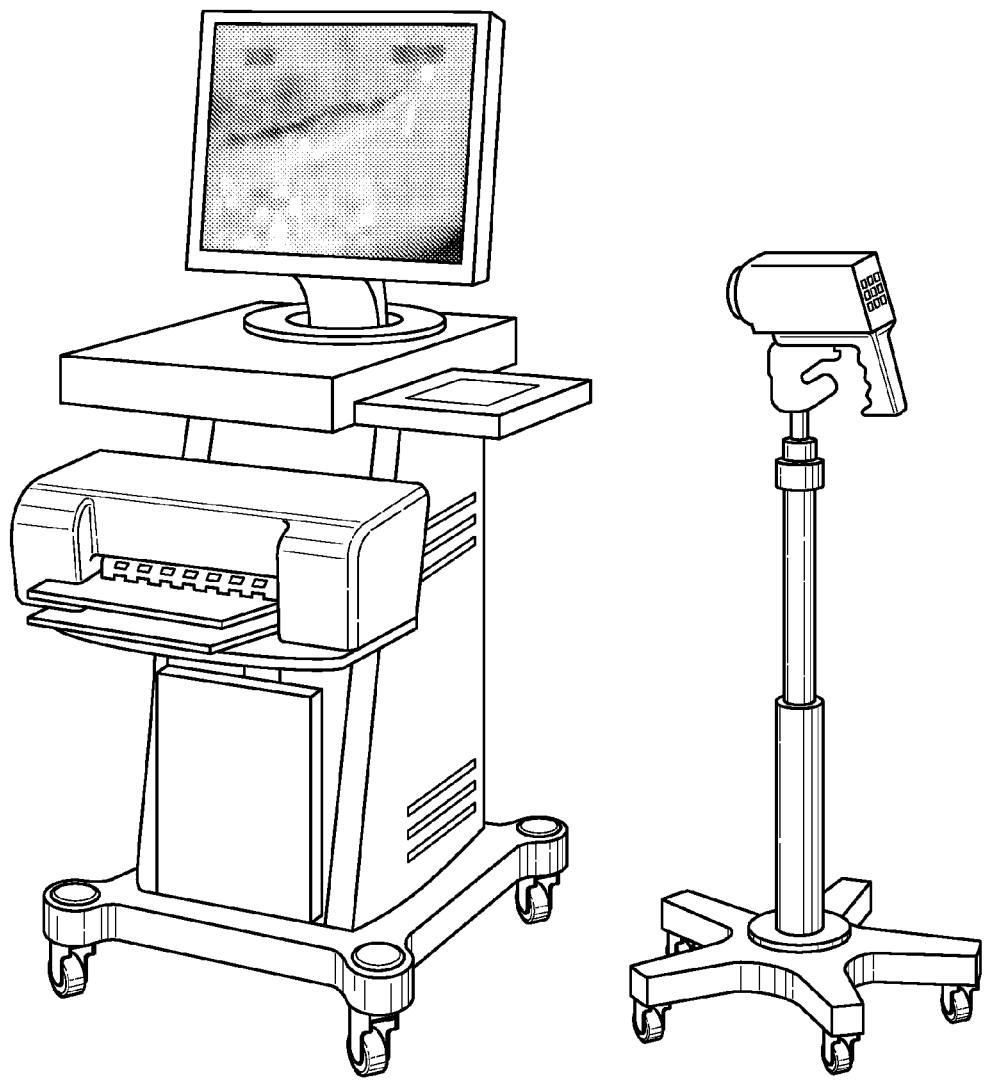
FIG. 1 shows a Philips Goldway Colposcope.

Colposcopy is being widely used for cervical cancer diagnosis and screening, especially in the developing countries like India and China. FIG. 1 shows the digital colposcope from Philips Goldway and an example images acquired by the colposcope is shown in FIG. 4. Interpretation of the colposcopic video data is not trivial and requires years of expertise. For developing countries, especially in remote rural areas, this expertise may not be present.

Figure 32:
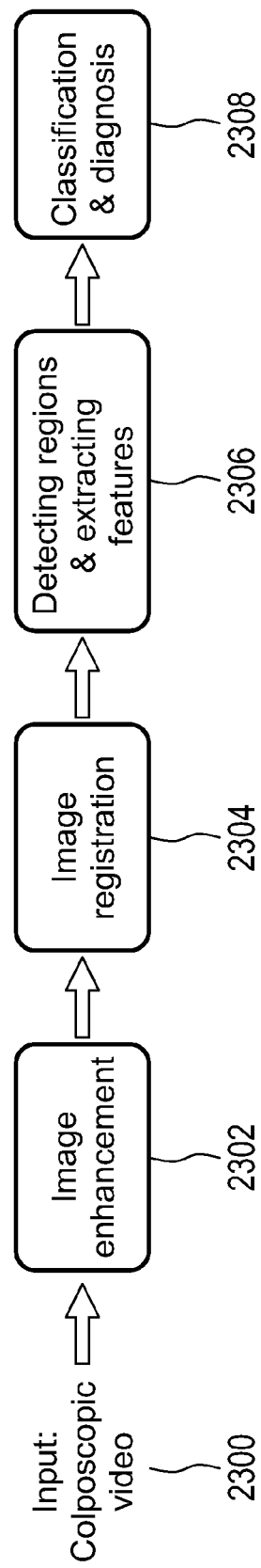
FIG. 32 shows a flow diagram which illustrates a general workflow for automated colposcopy.

FIG. 32 shows a flow diagram which illustrates the general workflow for automated colposcopy. In step 3200 colposcopic video is input. Next the image goes through image enhancement 3202. This may include such things as glint removal and green filtering. Next in step 3204 image registration is performed. Alignment of images to correct for inter-frame motion, pre- and post-acetic acid and post-iodine imaging and also during the zooming of images is performed. Next in step 3206 the images are processed to detect regions and extract features. For example during an acetowhite image, the margin and temporal delay might be determined along with iodine staining and the underlying blood vessel structure which is visible. Finally in step 3208 classification of the data that has been collected is performed and in some embodiments a diagnosis may also be performed. The diagnosis in some situations may be performed by a physician who is presented with data.

FIG. 32 shows the steps or components for the automated colposcopy system, where image registration is needed to align the input video frames, in order to
  compensate for the tissue and body movement of the patient;
  compensate for the camera motion: in the colposcopic examination, the clinician needs to move the camera to examine different parts of cervix;
  align images with different stain (Saline, Acetic acid, Lugol's Iodine);
  align images of different zooms: in the colposcopic examination, the clinician needs to zoom in and out to see different diagnostic features. Accurate image registration is crucial for extracting diagnostic features. Without image registration, it may not be possible to extract the diagnostic features that involve multiple images (e.g., acetowhitening kinetics).

Embodiments of the invention may provide:
  accurate image registration can be done with the current colposcope products of Philips Goldway, without introducing any new hardware (e.g., 3D imaging); and
  new features which can be added to the current colposcope products, for example, providing the stabilized colposcopic video to the gynecologist.

Embodiments of the invention may have the following features:
  Video registration is done by iteratively concatenating the transformation models of pair-wise registration between consecutive frames in the video;
  Region of Interest (ROI) segmentation is integrated with image registration
    In case registration fails, ROI segmentation is used to re-initialize image registration;
    Feature matching derived for registration can be used for ROI segmentation;

Image registration is done by finding correspondence of local features between two frames;

Three embodiments of feature matching: Lukas-Kanade tracking (KLT), SIFT feature detection and matching, and SLAM (Simultaneous Localization and Mapping);

The number of detected feature matches is examined as confidence/accuracy level for registration; if too few, registration of the current frame is skipped.

Colposcope video registration is used to align all the input video frames to a reference frame (or template frame); normally the first frame is selected. An alternative is to use the frame in the first part of colposcopic video where the segmentation algorithm (see below) successfully detects the region of interest (e.g., cervix). In the colposcopic examination process, the appearance of the cervix varies significantly due to 1) the camera movements, 2) the changes induced by the contrast agent like acetic acid, 3) the camera zoom factors. Therefore, it is very difficult (or impossible) to align two video frames acquired with a large time interval. The proposed solution is:

do pair-wise registration between consecutive frames, e.g., registering frame n+1 to frame n, and keep the transformation model T[n+1->n]. Because the relatively small changes in appearance between consecutive frames, the registration can be done with high accuracy;

for a given frame t, registration with frame 1 is done by iteratively concatenating the transformation models T[t->t-1], T[t-1->t-2], ... T[2->1].

1) Region of Interest (ROI) Segmentation

Region of Interest (ROI) segmentation is integrated with image registration. In the input video frames, the region of interest (e.g., cervix region) that is relevant for colposcopic diagnosis is first segmented. The registration will then be focused on the segmented region. That is, feature (extraction and) matching will only be performed in this region. The benefits of this may include:

speeding up the process of deriving feature correspondence, by focusing on an image patch (compared to the whole video frame). This could reduce the computational cost, for example, for KLT tracking;

reduce the unreliable feature matches or mis-matches (i.e., false positives). For instance, for SIFT feature matching, without ROI segmentation, it is possible that one feature in the ROI in frame one is matched with the feature outside ROI in frame two; with ROI segmentation, this kind of mis-matches can be avoided.

The ROI segmentation may be done manually, semi-automatically, or automatically. For example, for semi-automatic, the clinician can click in the video to indicate where the ROI is. For automatic ROI segmentation, it can be done in different ways, for instance, clustering in the color space or using a pre-trained object detector. The feature matches derived for registration can be used to improve ROI segmentation, for example, the extracted feature matches between frame one and frame two is used as additional evidence for ROI segmentation in frame two (if all features in frame one are inside ROI).

Image registration could fail, for example, in case of extremely large movements (causing motion blur) and occlusion (when the clinician is cleaning the cervix with cotton or is applying a contrast agent like acetic acid). In these cases, ROI segmentation will be adopted to re-initialize registration when the ROI is detected in the input frame. As an alternative, feature based registration may be considered.

2) Feature Detection and Matching

For the segmented ROI, registration is done by finding correspondence of local features. The feature matching can be implemented with different methods.

In one embodiment, Lucas-Kanade tracking (or KLT tracker) is adopted to track the features or find the correspondence in a local neighborhood.

In another embodiment, SIFT features are detected and then matched between the two video frames.

In another embodiment, Simultaneous Localization and Mapping method is used to derive feature matches.

The amount of feature matches found in the given video frames depends on the similarity between the two frames. Normally, for gradual appearance changes or small movements between two consecutive video frames, a large number of feature correspondences can be derived. The number of feature matches can be used as a confidence (or accuracy level) indicator about the registration. If it is below a threshold, this indicates there is much dissimilarity between the two frames (e.g., due to large movements or occlusion). In this case, the registration on the current frame is skipped, moving on to the next input frame. In this way, registration errors will not be accumulated (in the iteration mentioned above). If many frames have been skipped, the risk has increased that the two frames (i.e., the current frame and the reference frame) have become much dissimilar, indicating registration is difficult or risky. The registration will be re-initialized by the ROI segmentation, i.e., re-setting the template frame.

3) Image Registration

Finally, based on the detected feature matching, a transformation model (for aligning frame one with frame two) is estimated. Different transformation models can be adopted, according to the image variations in the video. With the transformation model, frame one is registered with frame two. As said above, pair-wise image registration is done for consecutive frames.

Figure 33:
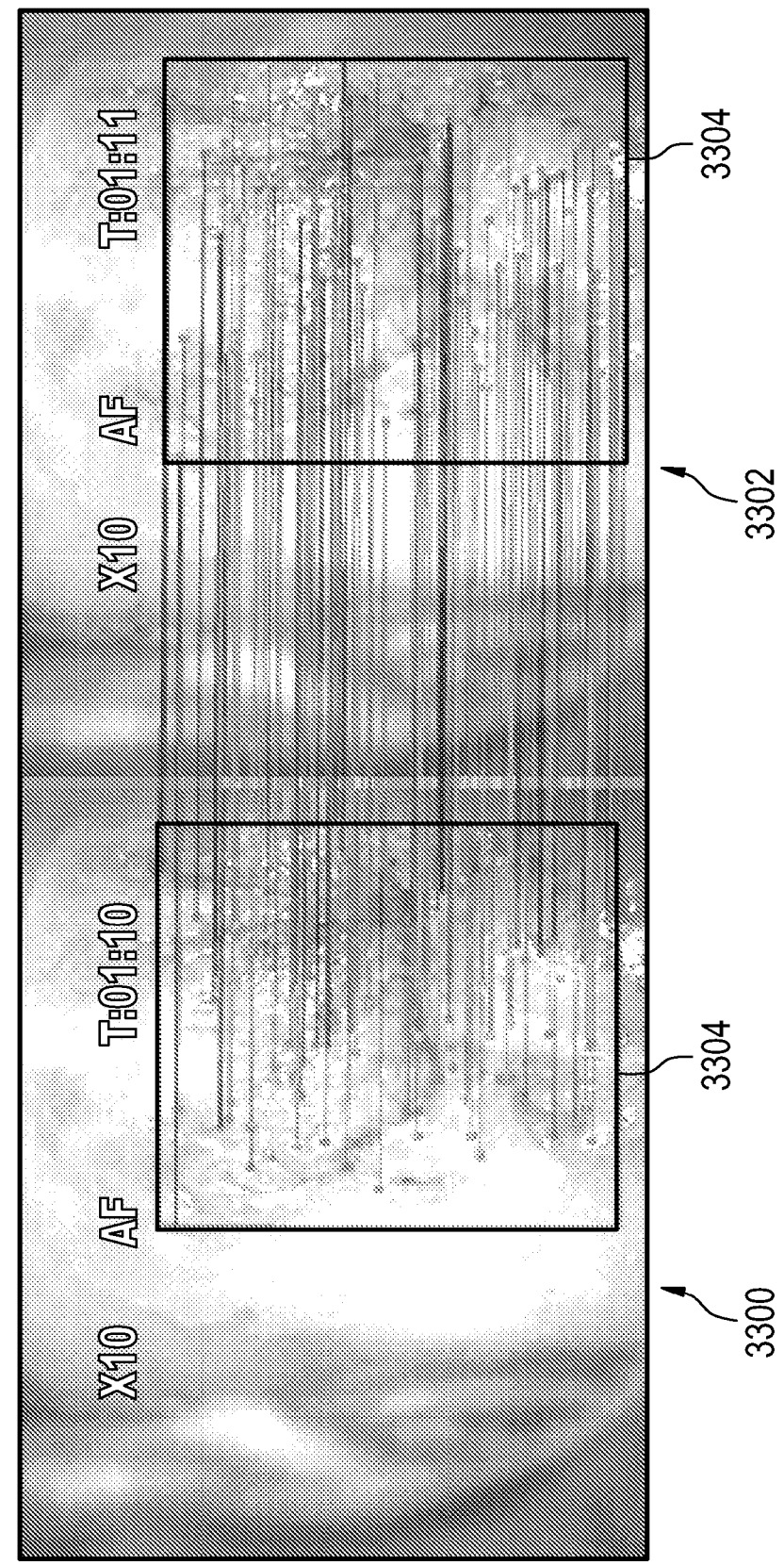
FIG. 33 illustrates an example of feature-based tracking.

FIG. 33 illustrates an example of feature-based tracking. There is an image 3300 and an image 3302 shown side-by-side. Image 3300 is at time t and image 3302 is at time t+1. Dots connected by a line show corresponding features. The boxes 3304 represent the same location in both images and are used to illustrate motion between frames 3300 and 3302. Such feature based tracking may be used to determine the transformation between each pair of consecutive image frames selected from the multiple image frames.

Figure 34:
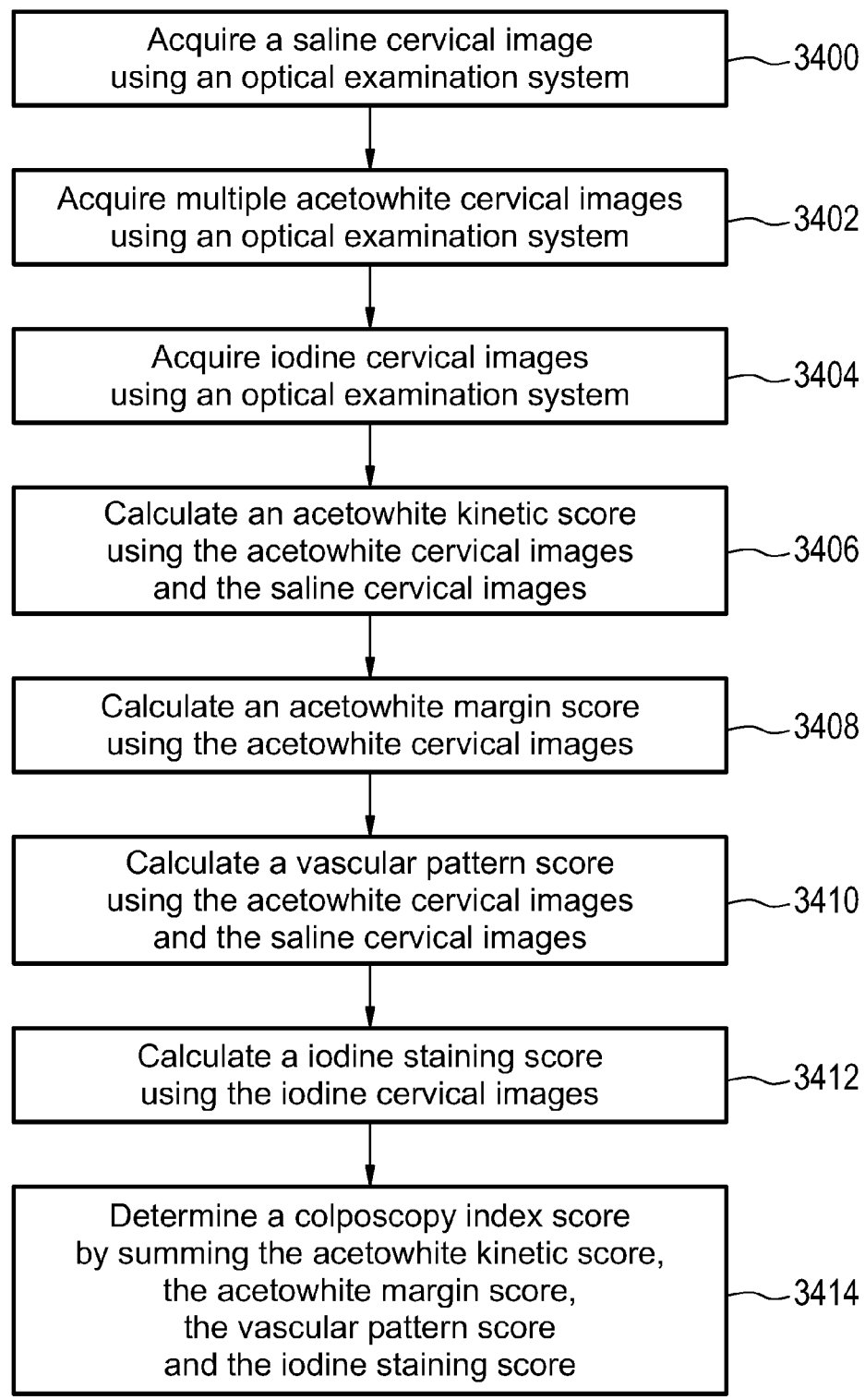
FIG. 34 shows a flow diagram illustrating a method according to a further embodiment of the invention.

FIG. 34 shows a flow diagram illustrating a method according to an embodiment of the invention. First in step 3400 a saline cervical image is acquired using the optical examination system. Next in step 3402 multiple acetowhite cervical images are acquired using an optical examination system. Next in step 3404 an iodine cervical image is acquired using an optical examination system. Next in step 3406 an acetowhite kinetic score is calculated using the acetowhite cervical images and the saline cervical images. Next in step 3408 an acetowhite margin score is calculated using the acetowhite cervical images. Next in step 3410 a vascular pattern score is calculated using the acetowhite cervical images and the saline cervical images. Next in step 3412 an iodine staining score is calculated using the iodine cervical image. Finally in step 3414 a colposcopy index score is determined by summing the acetowhite kinetic score, the acetowhite margin score, the vascular pattern score, and the iodine staining score.

Figure 35:
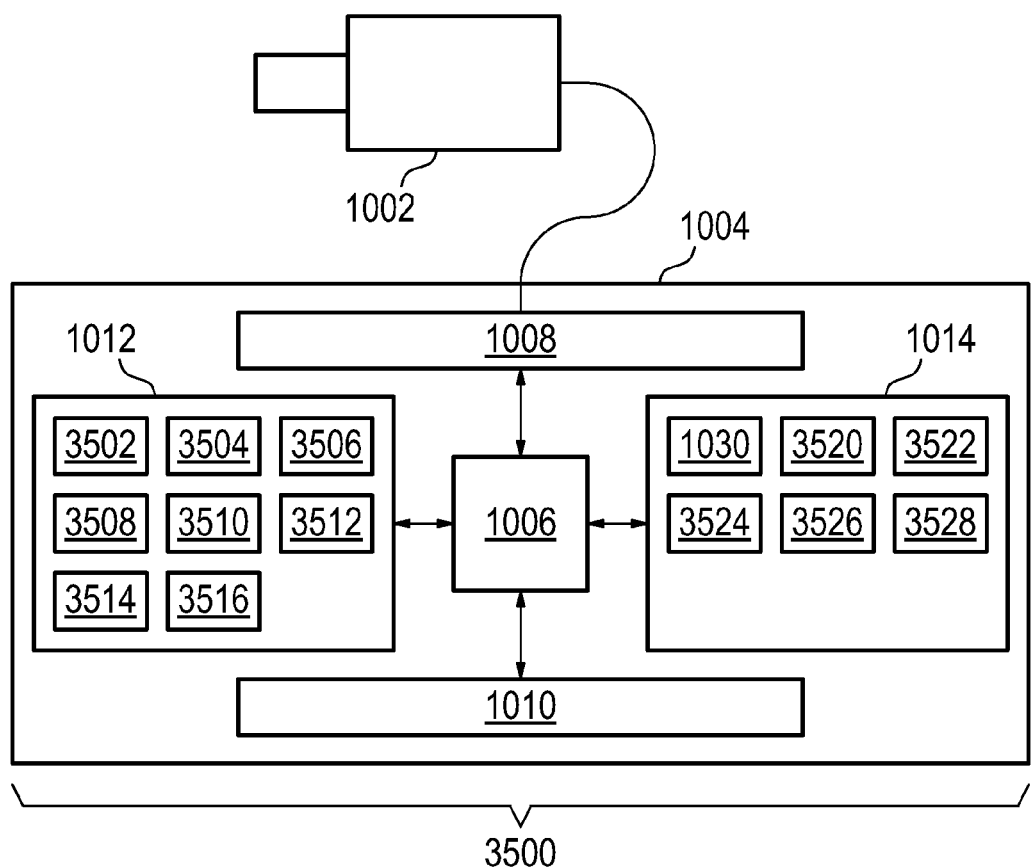
FIG. 35 illustrates a medical instrument according to a further embodiment of
   the invention.

FIG. 35 illustrates a medical instrument 3500 according to a further embodiment of the invention. The embodiment shown in FIG. 35 is very similar to the embodiment shown in FIG. 10. The computer storage 1012 and memory 1014 may also show the data objects and executable code shown in the computer storage 1012 and computer memory 1014 of the embodiment shown in FIG. 10.

The computer storage 1012 is shown as containing a saline cervical image 3502, acetowhite cervical images 3504 and an iodine cervical image 3506 which were acquired using the optical examination system 1002. The computer storage 1012 is further shown as containing an acetowhite kinetic score 3508, an acetowhite margin score 3510, a vascular pattern score 3512, and an iodine staining score 3514. The computer storage 1012 is further shown as containing a colposcopy index score 3516.

The computer memory 1014 is further shown as containing an acetowhite kinetic score calculation module 3520. The acetowhite kinetic score calculation module 3520 contains computer executable code which enables the processor 1006 to calculate the acetowhite kinetic score 3508 using the acetowhite cervical images 3504 and the saline cervical image 3502. The computer memory 1014 is further shown as containing an acetowhite margin score calculation module 3522. The acetowhite margin score calculation module 3522 contains computer executable code which enables the processor 1006 to calculate the acetowhite margin score 3508 using the acetowhite cervical images 3504.

The computer memory 1014 is further shown as containing a vascular pattern score calculation module 3524. The vascular pattern score calculation module 3524 contains computer executable code which enables the processor 1006 to calculate the vascular pattern score 3512 using the acetowhite cervical images 3504 and the saline cervical image 3502. The computer memory 1014 is further shown as containing an iodine staining score calculation module 3526. The iodine staining score calculation module 3526 contains computer executable code which enables the processor 1006 to calculate the iodine staining score 3514 using the iodine cervical image 3506. The computer memory 1014 further contains a colposcopy index score calculation module 3528. The colposcopy index score calculation module 3528 contains computer executable code which enables the processor 1006 to calculate the colposcopy index score 3516 using the acetowhite kinetic score 3508, the acetowhite margin score 3510, the vascular pattern score 3512 and the iodine staining score 3514.

The embodiment described in FIG. 35 may be useful eliminating the subjectivity from the process and reduce the learning period for a user, such as a Gynecologist. Such a system may be beneficial, because cancer arising from cervix is the 2nd most common cancer in women in world. India accounts for about 23% of the cases occurring globally. Colposcopes are used by gynecologists for the diagnosis/grading of precancerous and early invasive cervical cancer lesions and for identifying the biopsies' locations. Colposcopists follow the steps outlined below however it may vary in different settings and may be based on their training, e.g., in USA Lugol's Iodine step is skipped.

There are several steps in a colposcopic examination. First, a normal saline is applied to douche and clean any secretions. Next, images may then be acquired. A green filter may then be used and more images may be acquired. The green filter allows the inspection of the blood vessel pattern. Next a 3-5% acetic acid solution may be applied. The change in the appearance of the cervix over time and the duration of the change and the time is noted as part of the examination. Next Lugol's iodine may be applied and the partial and complete uptake of the iodine is examined. Finally a biopsy may be taken from any abnormal tissue regions. These steps involve huge subjectivity. Therefore there is also a huge subjectivity involved in using the colposcopes to provide an index for grading cervical cancer.

It has also been observed that the diagnosis using a colposcope has a long learning curve for new colposcopists. Interactive learning based on actual patients has been cited in the literature to accelerate the learning curve for new colposcopists.

Embodiments of the invention may provide a method and/or system to automatically generate an index for colposcopic examinations to grade the severity of precancerous and early cancerous lesions which should also accelerate the learning curve for new colposcopists. Unlike existing methods the claimed method may generate a colposcopic index that is used or reviewed by a clinician.

The automated scoring methodology for colposcopes may have the following benefits:

Decreases the interobserver variability in grading the severity of cancer

Objectively scores cervical cancer and also does this automatically

Provide on job training to a gynaecologist in an interactive way to accelerate their learning curve Embodiments of the invention may provide for an automated or semi-automated method to provide Colposcopy index in an interactive way with colposcopes using a combination of image/video analysis algorithms.

Features of such a system may include:

1. Automatic scoring: The proposed system analyzes the data captured from a video colposcope while performing the colposcopy procedure and provides colposcopy index automatically.

2. Parameter selection for score computation: The criteria for selecting the parameters or clinical findings for computing the score is displayed to the user. The clinical findings are mainly the acetowhite kinetics, acetowhite margins, vascular patterns and iodine staining. Each finding is associated with a "confidence level" provided by the algorithm. With a confidence level, the doctors can know which finding is in doubt (for automatic analysis software). For low-confidence findings, the doctor can check them manually, to confirm the findings. The user has the option to agree/disagree to the selected parameters. The colposcopist could focus on analyzing the selected parameters to give a better diagnosis.

3. Region annotation for selected parameters: The proposed system would annotate regions in the images which are indicative of the selected parameters. The annotated regions can be used by the colposcopist to train his or her self or others.

4. Storing the annotated region: These annotated regions would be stored with the history of the patient to refer in the future to track the prognosis of the abnormality or even for the biopsy/treatment.

5. Selecting the type of score: The Colposcopist can chose from a list of clinically used indices, e.g., Reid's score, Modified Reid's score, Simplified Reid, Swede score, and etc., for grading the severity of cancerous lesions.

6. Future developments or changes in scoring methodology of the colposcopic examinations can also be incorporated as the essential parameters are being computed automatically by the system.

A typical colposcope may have four components: 1) camera with light source, 2) video capture unit, 3) display unit, and 4) data management unit to manage patient information. A block diagram of the colposcope is shown in FIG. 36.

Figure 36:
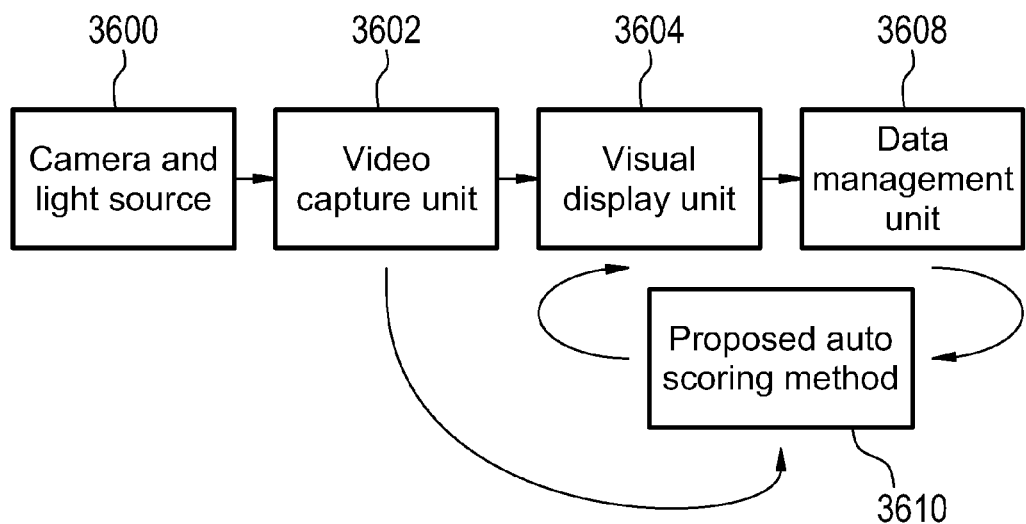
FIG. 36 shows a block diagram which illustrates the functional components of a medical instrument according to a further embodiment of the invention.

FIG. 36 shows a block diagram which illustrates the functional components of a medical instrument according to an embodiment of the invention. Block 3600 is a camera and light source. The camera and light source provides data to a video capturing unit 3602. Images from the video capturing unit can be transferred to a visual display unit 3604 and also to a processor running software which provides an automatic scoring method 3610 which can also be provided to a data management unit 3608. The data management unit 3608 can also provide data to the processor which does the auto scoring 3610 and the results of the auto scoring may also be displayed on the visual display unit 3604.

Figure 37:
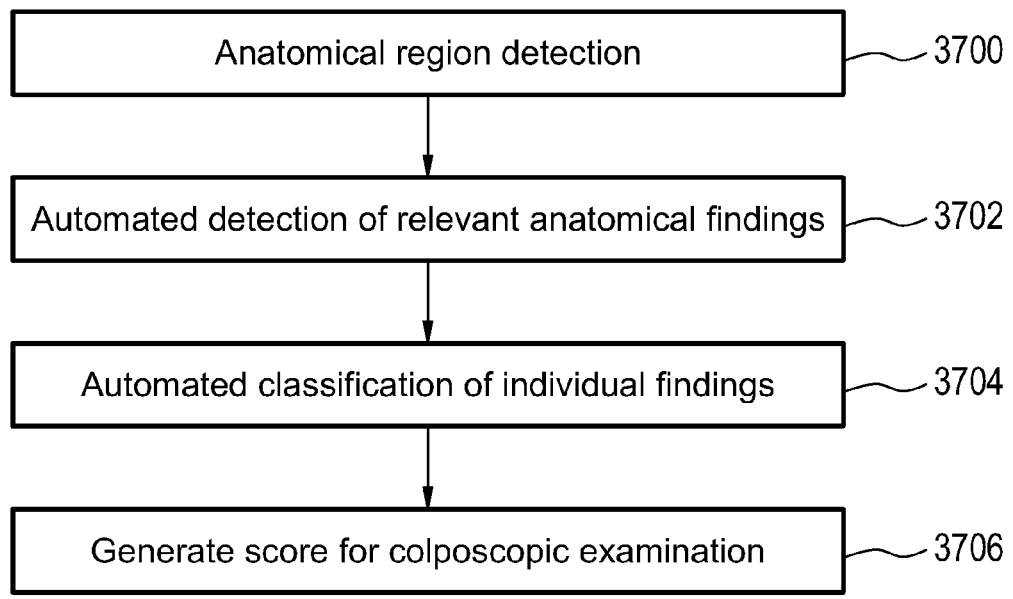
FIG. 37 shows a block diagram which illustrates a method according to a further embodiment of the invention.

FIG. 37 shows a block diagram which illustrates a method according to an embodiment of the invention. First in step 3700 anatomical region detection is performed. Next in step 3702 automated detection of relevant anatomical findings is performed. Next in step 3704 the automated classification of individual findings is performed and finally in step 3706 a score for the colposcopic examination is generated.

Figure 38:
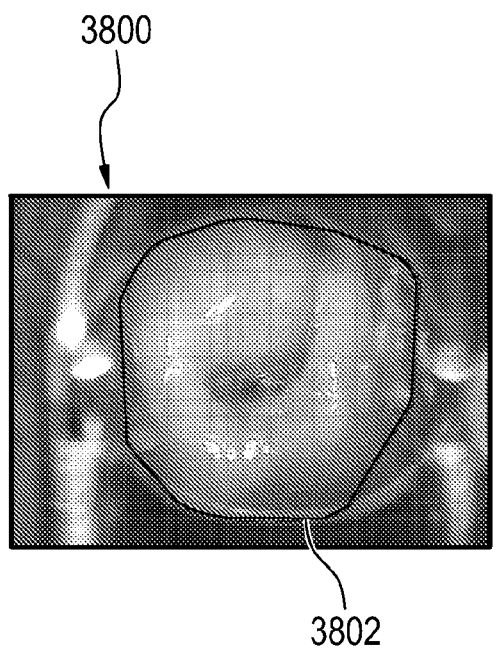
FIG. 38 shows an example of an acetowhite cervical image.

The anatomical region detection by an embodiment of the invention is now discussed. First, relevant objects are identified in a cervical image, i.e., Os, Transformation Zone (TZ is the region determined by old Squamo Columnar Junction (SCJ) and new SCJ) and Cervix. The region of interest, i.e. Cervix region is automatically identified using a dynamic thresholding scheme on the red component of the image followed by a K means clustering for pre and post acetic acid images. If the cluster identifies a region with size less than one/tenth (this has been determined heuristically) of the size of the image then we conclude that the cervix is not visible in the image. Otherwise, the cluster is considered to be the cervix region. The algorithm has been verified on 201 pre and post acetic acid images and gives accurate segmentation results in 95% cases. In case of Lugol's Iodine images Otsu thresholding is used to differentiate the cervix region from non-cervix regions. The cervix region identified in an acetic acid applied image and a Lugol's Iodine applied image using the above mentioned algorithms is given below:

FIG. 38 shows an example of an acetowhite cervical image 3800. There is a cervical region 3802 identified in the image 3800.

Figure 39:
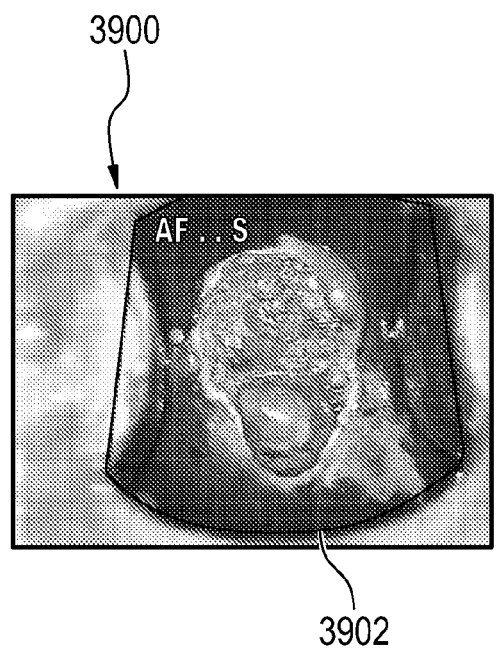
FIG. 39 shows an example of an iodine cervical image.

FIG. 39 shows an example of an iodine cervical image 3900. There is a cervical region 3902 identified in the iodine cervical image 3900.

Old SCJ detection is a two step approach. In the first step post Lugol's Iodine images are processed to tentatively detect the transformation zone based on the color changes that it depicts on the application of Lugo 1 Iodine. The post Lugol's Iodine image is segmented using color based Kmeans clustering into two clusters, IL1 and IL2. It is observed that the histogram of the red component (IL1(R)) of the cluster containing the transformation zone follows a normal distribution while it is not true for the other cluster. In order to automatically identify the cluster that contains the transformation zone, we model the normal distribution. Let the histogram for the red component of both the clusters be represented as H(IL1(R)).

Figure 40:
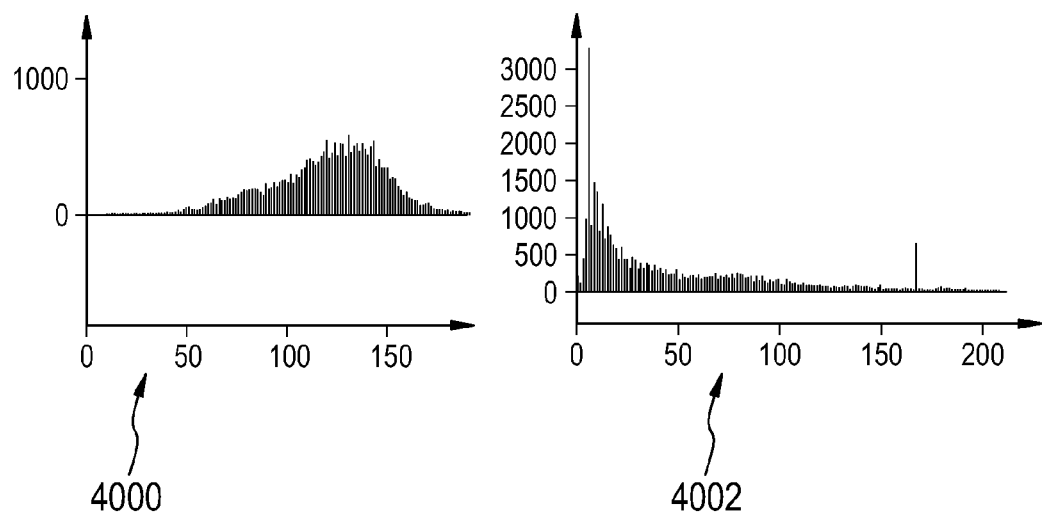
FIG. 40 shows two histograms.

FIG. 40 shows two histograms 4000, 4002. Histogram 4000 shows the normal distribution of red values in clusters representing a transformation zone. Histogram 4002 shows the random distribution of red values that do not contain the transformation zone. In image 4000 the normal distribution of red values in cluster representing transformation zone is examined and in image 4002 the Random distribution of red values that do not contain transformation zone and H(IL2(R)). Both the histograms 4000, 4002 are smoothed and the number of peaks in H(IL1(R)) and H(IL2(R)) are identified. The histogram containing only one peak is considered to belong to the cluster that contains the transformation zone. We then iteratively remove small and disjoint regions in this cluster. The convex hull of this cluster is defined as the tentative transformation zone in IL. In the second step, the tentative transformation zone identified in Lugol's Iodine images is mapped using registration techniques to post acetic acid image and pre acetic acid images. This demarcates the old SCJ region in pre acetic and post acetic acid images.

Figure 41:
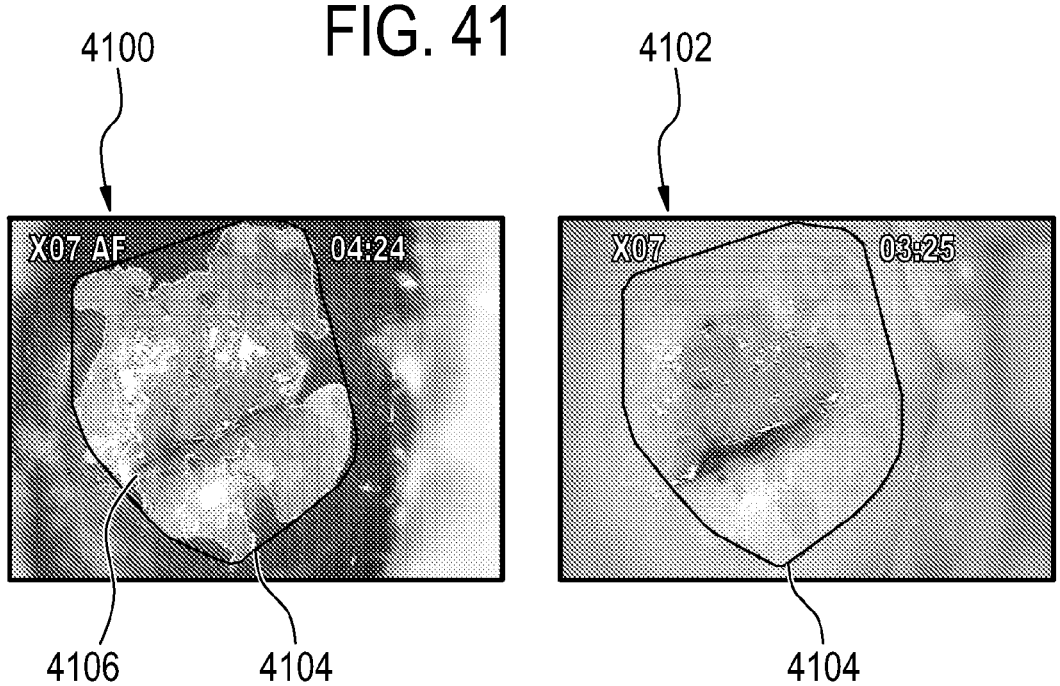
FIG. 41 shows an iodine cervical image and an acetic acid cervical image of the same cervix.

FIG. 41 shows an iodine cervical image 4100 and an acetic acid cervical image 4102 of the same cervix. There is a cervical region 4104 identified in both Figures. Also shown is an old SCJ 4106 that was mapped from the post-iodine image to a post-acetic acid image.

New SCJ region identification is a two step process of feature extraction and classification. It takes as input the cervix region to identify the features. Typical features used are mean red, standard deviation of red, spatial pixel location and red to green and red to blue ratios. Spatial pixel location, red to green ratio and red to blue ratio is applied on the entire cervix region while mean red and standard deviation of red is applied to blocks of 4×4 and 5×5 pixels in the cervix region. Initial thresholding for the New SCJ region is done on the basis of mean-red and standard deviation of red.

Figure 42:
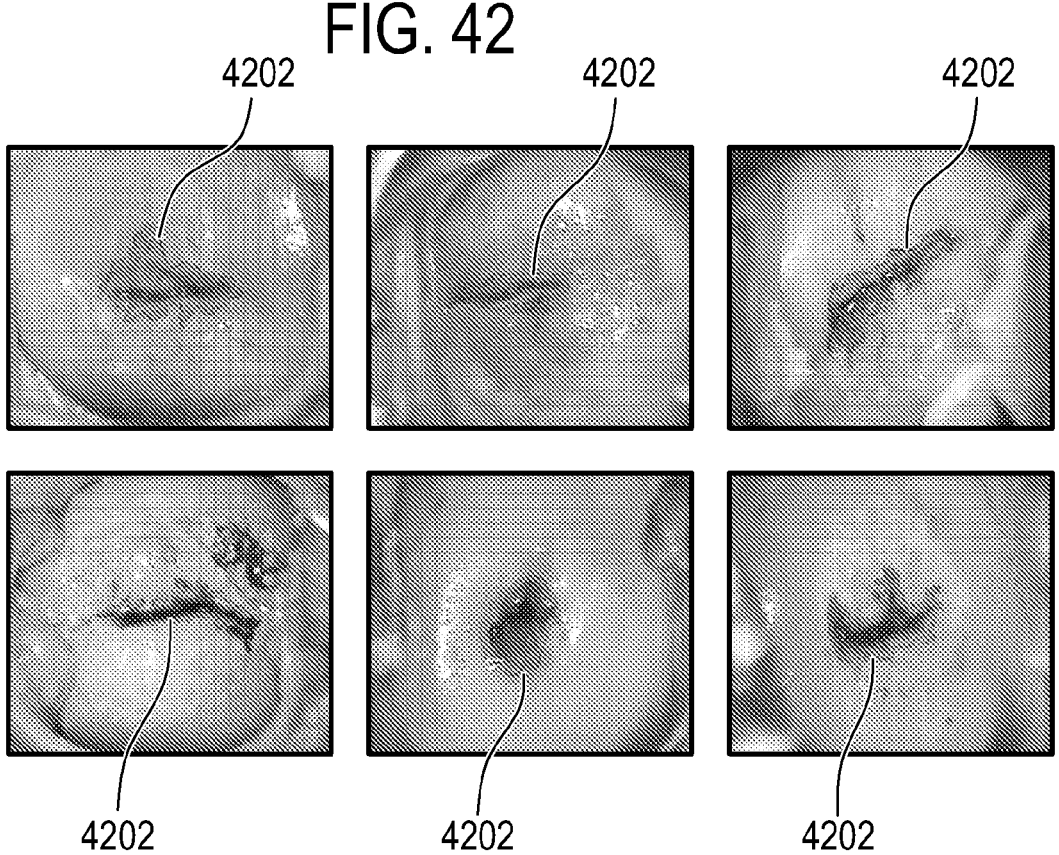
FIG. 42 shows a series of six different cervical images.

This thresholded image with R/G, R/B and spatial location gives us the initial probability using the function: Prob_pixel_NewSCJ=ImgRed.*(R2G).*(R2B).*Gradient. Using that initial probability and the primary classification the posterior probability is computed by Conditional Random Field Model. After the image had been classified by the CRF the major area is extracted which is considered to be the New SCJ. Some of the results to identify New SCJ is shown in FIG. 42, which shows a series of six different cervical images. In each of these images the new SCJ region 4202 is identified.

Os detection in pre and post acetic acid images is applied on the New SCJ region identified. The New SCJ region contains the columnar epithelium and the Os. Both of these regions are separated using minimum variance quantization which is followed by iteratively removing the small disjoint regions in columnar epithelium and Os. Alternatively both the regions could also be separated using Otsu thresholding. Anatomically in a two dimensional representation of the cervix the Os lies inside the columnar epithelium. This is used as a clue to identify the Os region from columnar epithelium region. Some of the results of the Os detection algorithms are shown in FIG. 43.

Figure 43:
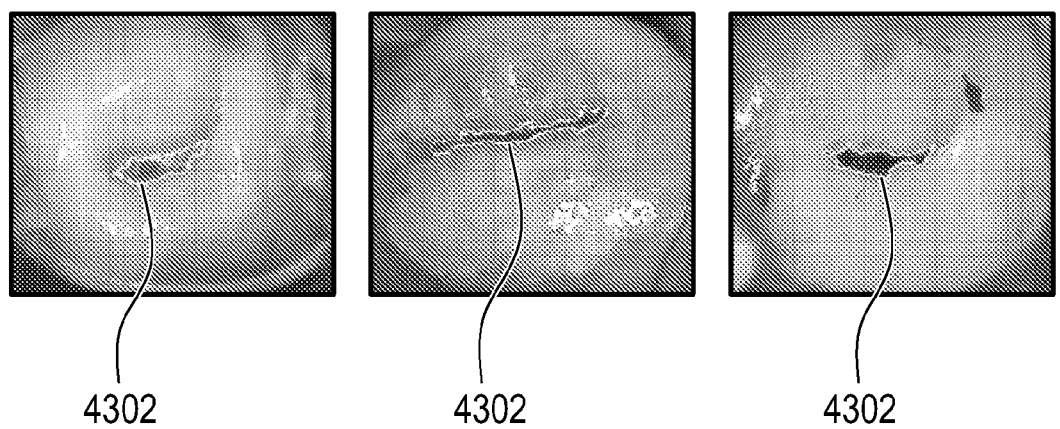
FIG. 43 shows a series of three cervical images which illustrate the detection of the Os in pre- and post-acetic acid images.

FIG. 43 shows a series of three cervical images which illustrate the detection of the Os in pre- and post-acetic acid images. The Os are labeled 4302.

Next, the automated detection of relevant colposcopy findings is discussed. Once the relevant anatomical regions are identified in an image, the user is shown a list of colposcopy findings that are automatically computed from the anatomical regions identified.

Figure 44:
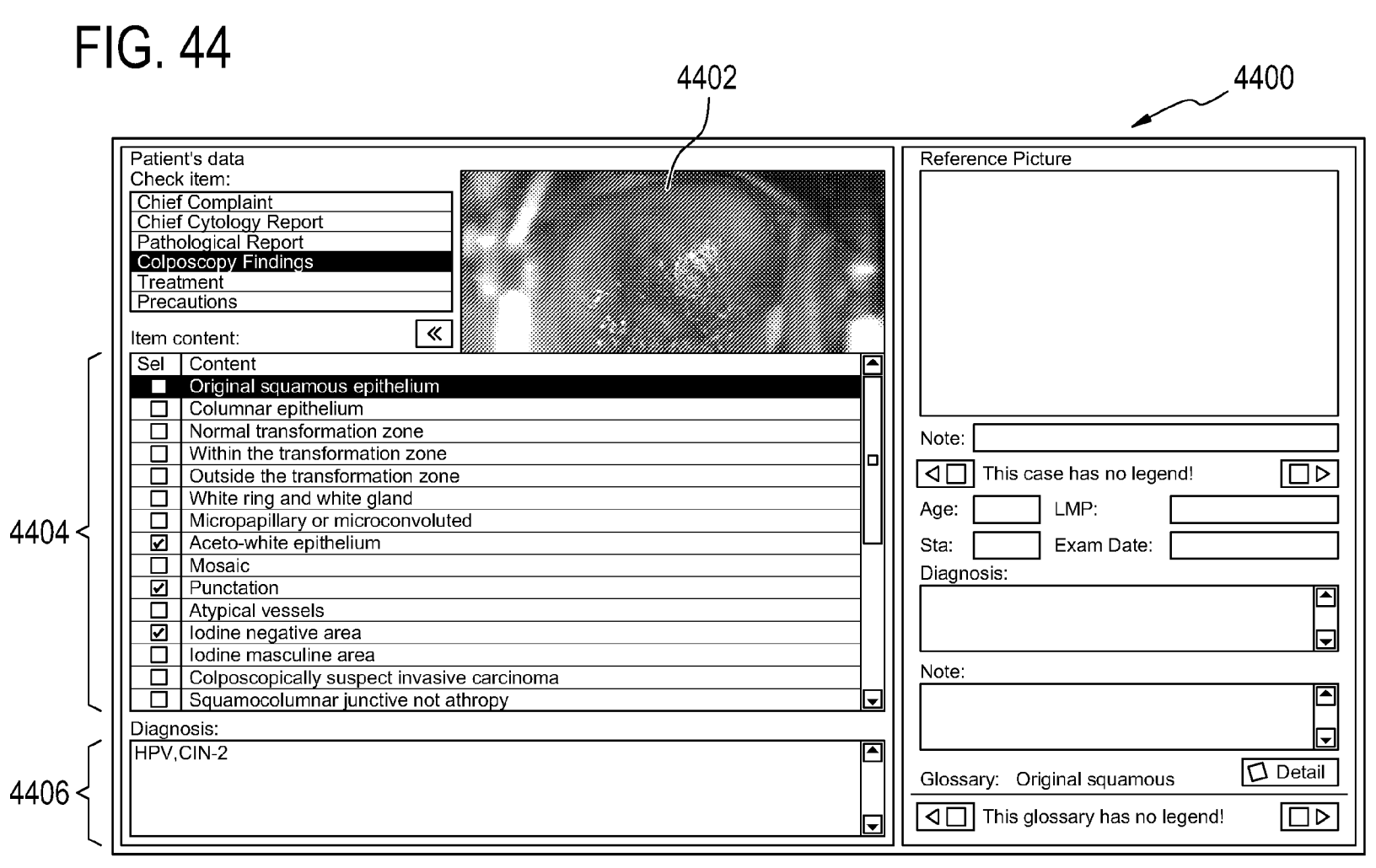

FIG. 44 illustrates a user interface 4400 according to an embodiment of the invention. In this user interface 4400 a cervical image 4402 is displayed. The region 4404 shows colposcopic findings or boxes which allow different regions of the cervical image 4402 to be selected. Box 4406 shows a likely diagnosis. In this user interface, relevant colposcopic findings displayed to the user automatically.

Automated identification of some of the relevant clinical findings that contributes to the scoring of a colposcopic examination is as follows:

Acetowhite kinetics: The transformation zones identified in the pre and post acetic acid images are the regions between old SCJ and new SCJ. Opacity difference score is computed for all post acetic acid images with respect to the pre acetic acid images may provide information of the presence, size, location, location with respect to transformation zone and grading of acetowhite epithelium. An example of opacity difference score obtained for a set of post acetic acid images with respect to pre acetic acid images is shown in FIG. 45.

Figure 45:
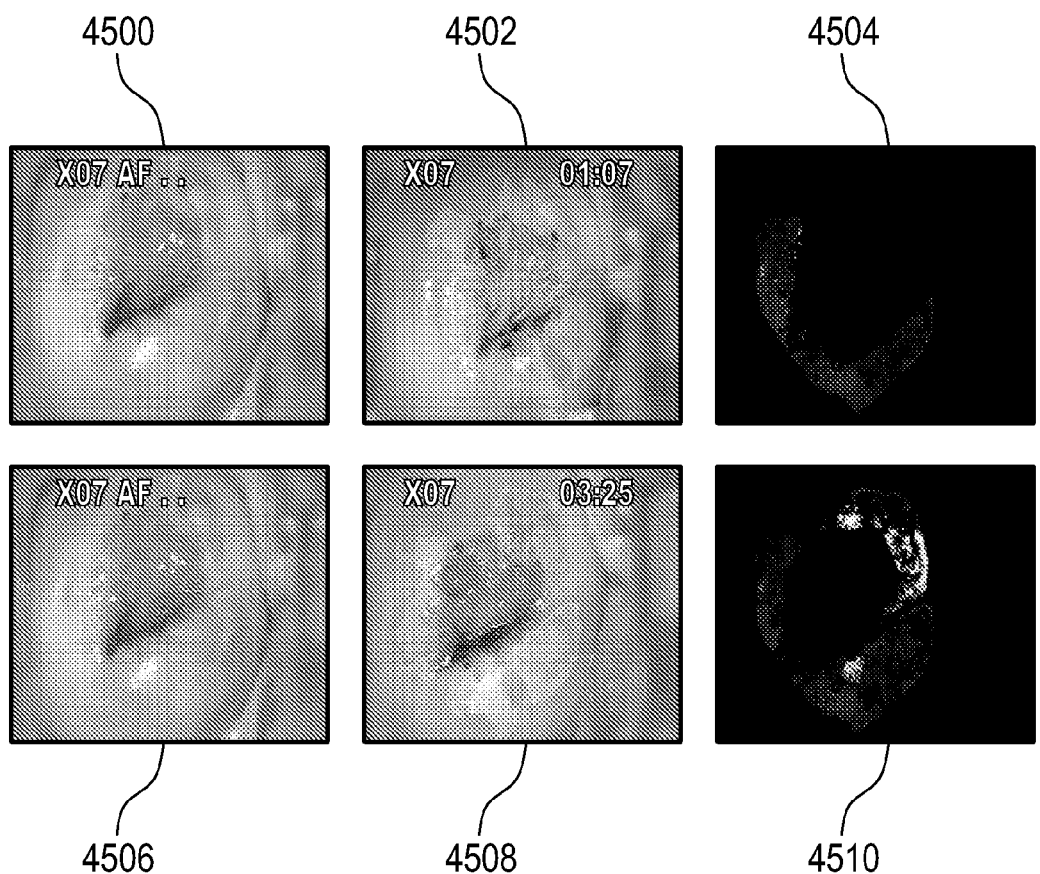
FIG. 45 shows a series of six cervical images.

FIG. 45 shows a series of six cervical images 4500, 4502, 4504, 4506, 4508, 4510. Image 4500 shows a pre-acetic acid image. Image 4502 shows the same cervix after the application of acetic acid after one minute. Image 4504 shows the opacity image with an opacity difference score of 18.46. Image 4506 is the same as image 4500. Image 4508 shows the same cervix three minutes after acetic acid has been applied. Image 4510 shows the opacity image calculated from images 4506 and 4508. The opacity difference score of image 4510 is 43.28.

This process may be followed by computing features from the boundaries of acetowhite regions to classify them into sharp, indistinct or feathered. One of the features for classification is the number of zero crossings in the boundaries. A "zero-crossing" is a point in the boundary where the sign of a boundary changes from positive to negative or negative to positive. A sharp boundary has more zero crossings than an indistinct boundary.

Punctation marks present on the cervix region is another important feature for the diagnosis of cervical cancer. They are a marker of abnormal vessels' architecture and their presence is significantly correlated to the existence of pre- and cancerous lesions of the cervix. A hierarchical filtration approach is used followed by a learning based framework to detect different kinds of punctation (fine/coarse/diffused) and segment those areas for diagnostic assistance. This approach may comprise two stages: (1) Crude level punctation detection: It is based on interest point detection followed by several steps of object filtration to remove falsely detected objects. (2) Fine level punctation detection: a learning based framework is build to classify the crudely detected punctations robustly. An example of punctation detection is shown in FIG. 46.

Figure 46:
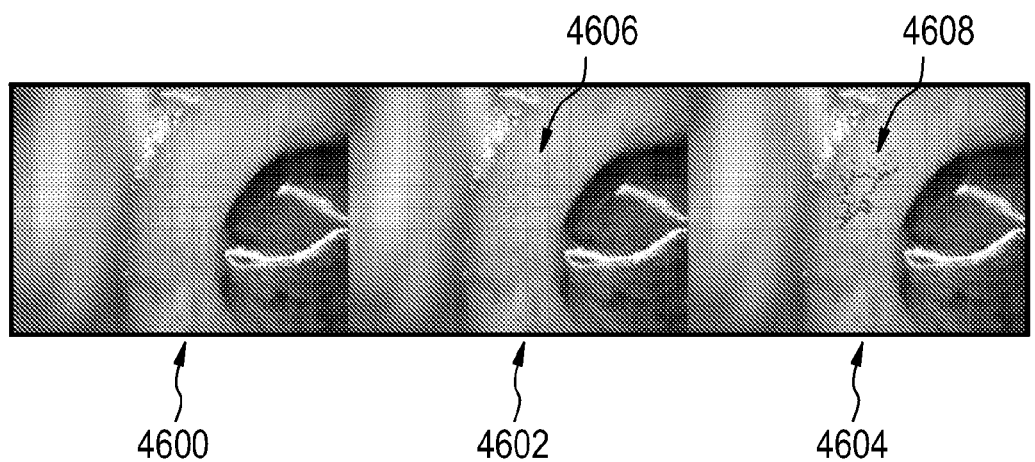
FIG. 46 shows three versions of the same acetowhite cervical image to illustrate the identification of punctation marks.

FIG. 46 shows three versions of the same acetowhite cervical image 4600, 4602, and 4604. FIG. 46 illustrates the identification of punctation marks. Image 4600 is the raw cervical image. Image 4602 illustrates the identification of individual punctation marks 4606. Image 4604 shows punctation mark regions 4608 where there is a concentration of punctation marks.

Mosaic patterns are another important characteristic which contribute to the computation of severity of the cancer. Their presence is significantly correlated to the existence of precancerous and cancerous lesions. They are detected using the texture based analysis. An example result is shown in FIG. 47.

Figure 47:
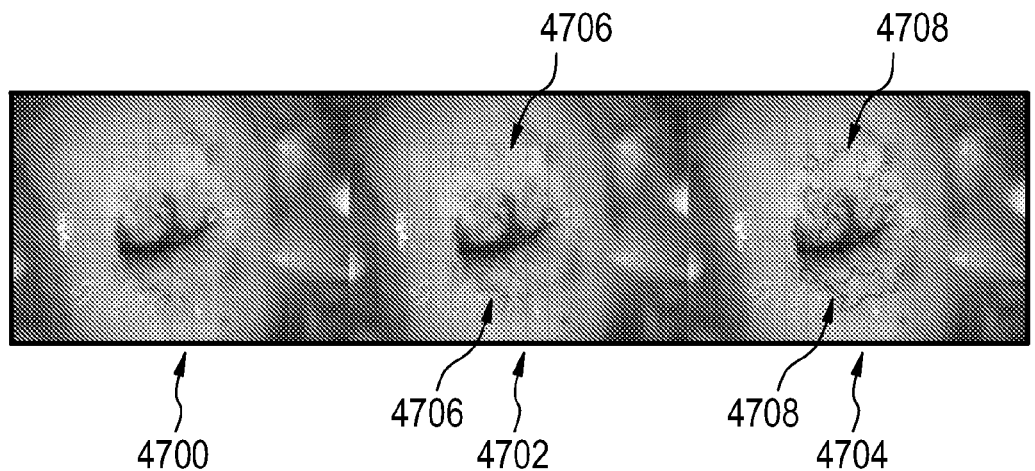
FIG. 47 shows three versions of the same acetowhite cervical.

FIG. 47 shows three versions of the same acetowhite cervical image 4700, 4702, 4704. In this image the identification of mosaic patterns is illustrated. Image 4700 is the raw image. Image 4702 shows the identification of mosaic regions 4606. Image 4704 shows lines which highlight the regions 4708 where there is a large number of mosaics present.

Atypical vessels present very important criterion for staging the severity of cancer. We detect the atypical vessels by color based filtering followed by line based detection. The presence of white rings and glands is a normal feature of the transformation zone, but in the case of abnormal pathology the rings are wider. White rings are identified as follows. Since the white rings are circular or elliptical in shape, a Hough transform for circle detection is used to identify candidates that have appearance of white glands. In the next step the identified candidates are filtered out based on certain features like white color, size, position within the transformation zone and etc. to identify the actual white glands.

Figure 48:
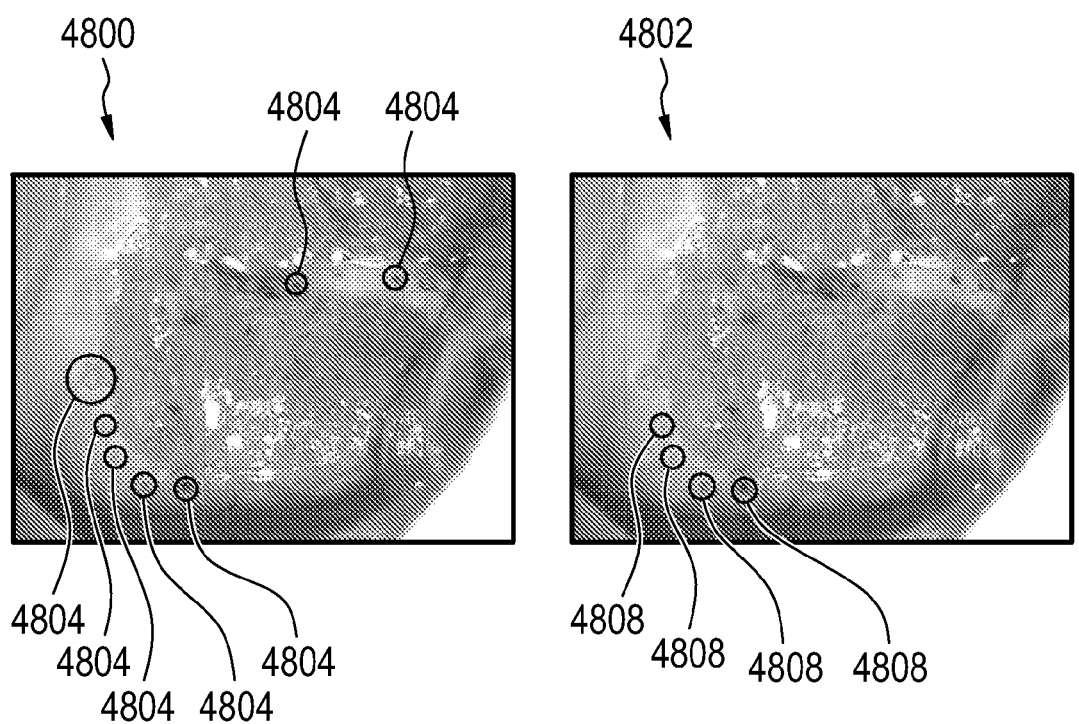
FIG. 48 shows two identical cervical images.

FIG. 48 shows two identical cervical images 4800, 4802. In image 4800, regions 4804 are identified or marked which may possibly be white glands. Image 4802 shows regions 4808 which are positively identified as white glands. Essentially candidates identified in image 4800 and white glands are identified after filtering as show in image 4802.

The results of iodine staining of the cervix are important for generating the score for the colposcopic examinations. Immature metaplastic epithelium turns iodine negative while mature metaplastic epithelium turns partially or completely stained brown with Lugol's Iodine. Low grade precancerous lesions are iodine negative while higher grade ones take a mustard yellow stain. In order to automatically determine the iodine changes, the iodine negative and positive regions are separated using Otsu thresholding. This is followed by identifying if the iodine negative area lies within the transformation zone or not. If the iodine negative region is identified in the transformation zone or regions where the acetowhite regions are present then the boundary for the iodine negative regions are analyzed. We compute the total number of zero crossings in the boundary. If the number of zero crossings is more than a threshold then the boundary is said to be indistinct or else it is considered as sharp.

Next, the automated classification of individual findings is discussed. In this step, each of the individual findings (the acetowhite kinetics, acetowhite margins, vascular patterns and iodine staining) is automatically given an independent score as shown in the following figures to the user based on the automatic detection of clinical findings as previously discussed. This section maps to the second feature discussed above. The system shows the confidence with which the score is given. The user has the option to agree or disagree with the score provided by the system.

The main purpose of this section is to give a score to a colposcopic recording based on 4 different clinical findings:
1. margins (represented by margins of acetowhite regions),
2. color (represented by aceto white kinetics),
3. vessels (represented by mosaics, punctations and atypical vessels), and
4. iodine staining (represented by color uptake of iodine).

Figure 49:
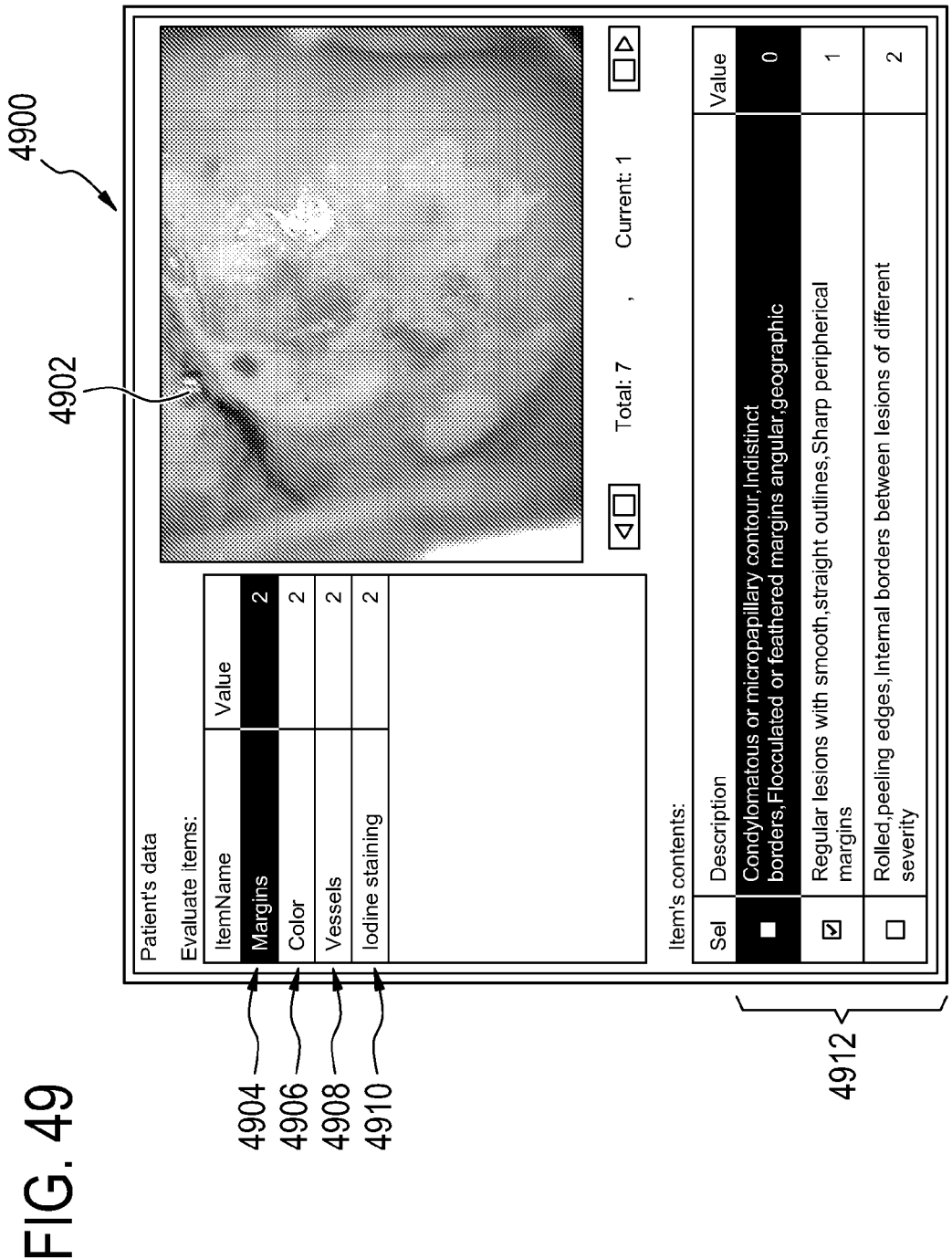
FIG. 49 shows a user interface according to an embodiment of the invention.

Once the aceto white regions are identified, the boundaries for these regions are obtained. Aceto white margins can be broadly subclassified into 3 types as shown in FIG. 49. FIG. 49 shows a user interface 4900 according to an embodiment of the invention. The user interface 4900 shows a cervical image 4902. Next to the cervical image 4902 is shown an acetowhite margin score 4904, an acetowhite kinetic score 4906, a vascular pattern score 4908, and an iodine staining score 4910. Below this there is a score adjustment selector. The score adjustment selector 4912 can be used by a healthcare provider to adjust the acetowhite margin score 4904 if he or she disagrees with the assessment. Using this user interface different scores can be selected and an image 4902 can be displayed and the score can be modified with the score adjustment selector 4912.

Figure 50:
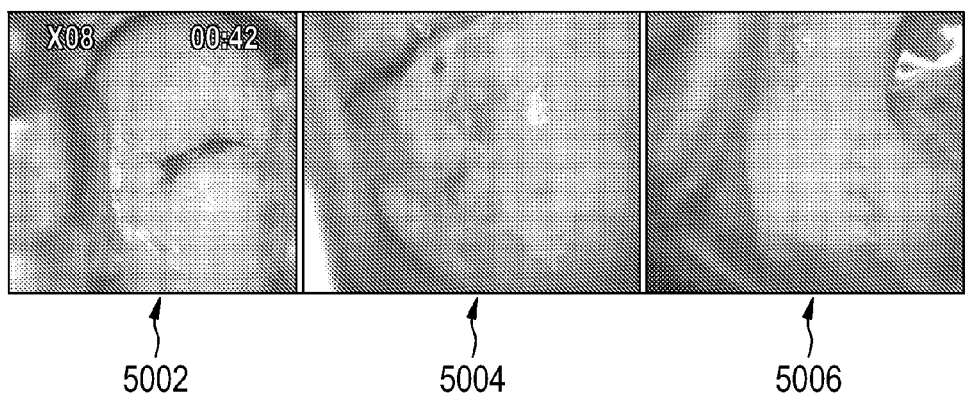
FIG. 50 shows three acetowhite images which illustrate a condylomatous cervical image, a sharp margins cervical image, and a rolled margins cervical image.

If the aceto white margins are outside the transformation zone then a score of zero is given. When the aceto white regions are inside the transformation zone, then we compute the number of zero crossings in the boundaries. A "zero-crossing" is a point in the boundary where the sign of a boundary changes from positive to negative or negative to positive. A sharp boundary has more zero crossings than an indistinct boundary. Threshold to distinguish sharp and indistinct boundary is determined experimentally. Aceto white region with sharp boundary is given a score of 1. An indistinct boundary surrounded by aceto white regions with different opacity index is given a score of 2. FIG. 50 shows examples with different margin scores.

FIG. 50 shows acetowhite images 5002, 5004, 5006 which illustrate a condylomatous cervical image 5002, a sharp margins cervical image 5004, and a rolled margins cervical image 5006.

Figure 51:
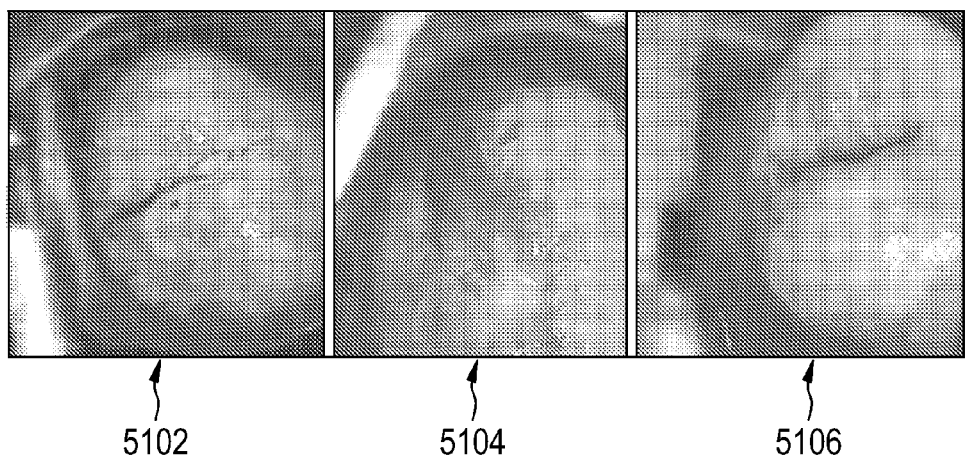
FIG. 51 shows three acetowhite cervical images for demonstrating three sub-classes of the opacity index.

Aceto white kinetics can be broadly subclassified into 3 types as shown in FIG. 51. FIG. 51 shows three acetowhite cervical images 5102, 5104, 5106 for demonstrating three sub-classes of the opacity index. Image 5102 shows a snow white appearance, image 5104 shows a shiny off white appearance, and image 5106 shows a dense white appearance. For each of the three subclasses, the opacity index shows the following patterns. This determines the score for clinical findings of color.

Figure 52:
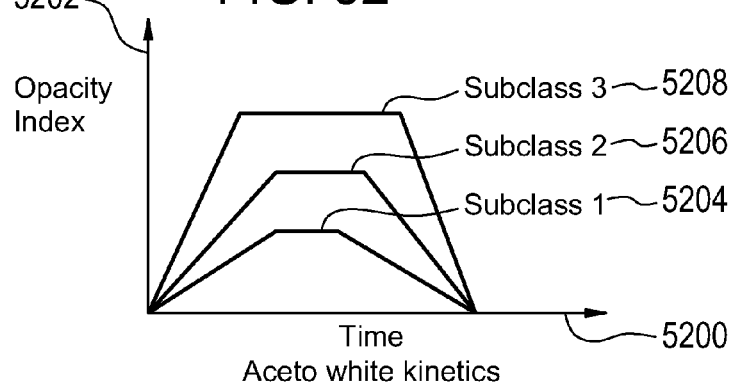
FIG. 52 shows a plot of the time versus the opacity index.

FIG. 52 shows a plot of the time 5200 versus the opacity index 5202. In this plot are three sub-classes; sub-class 1 5204 corresponds to image 5102, sub-class 2 5206 corresponds to image 5104 and sub-class 3 5208 corresponds to image 5106.

Figure 53:
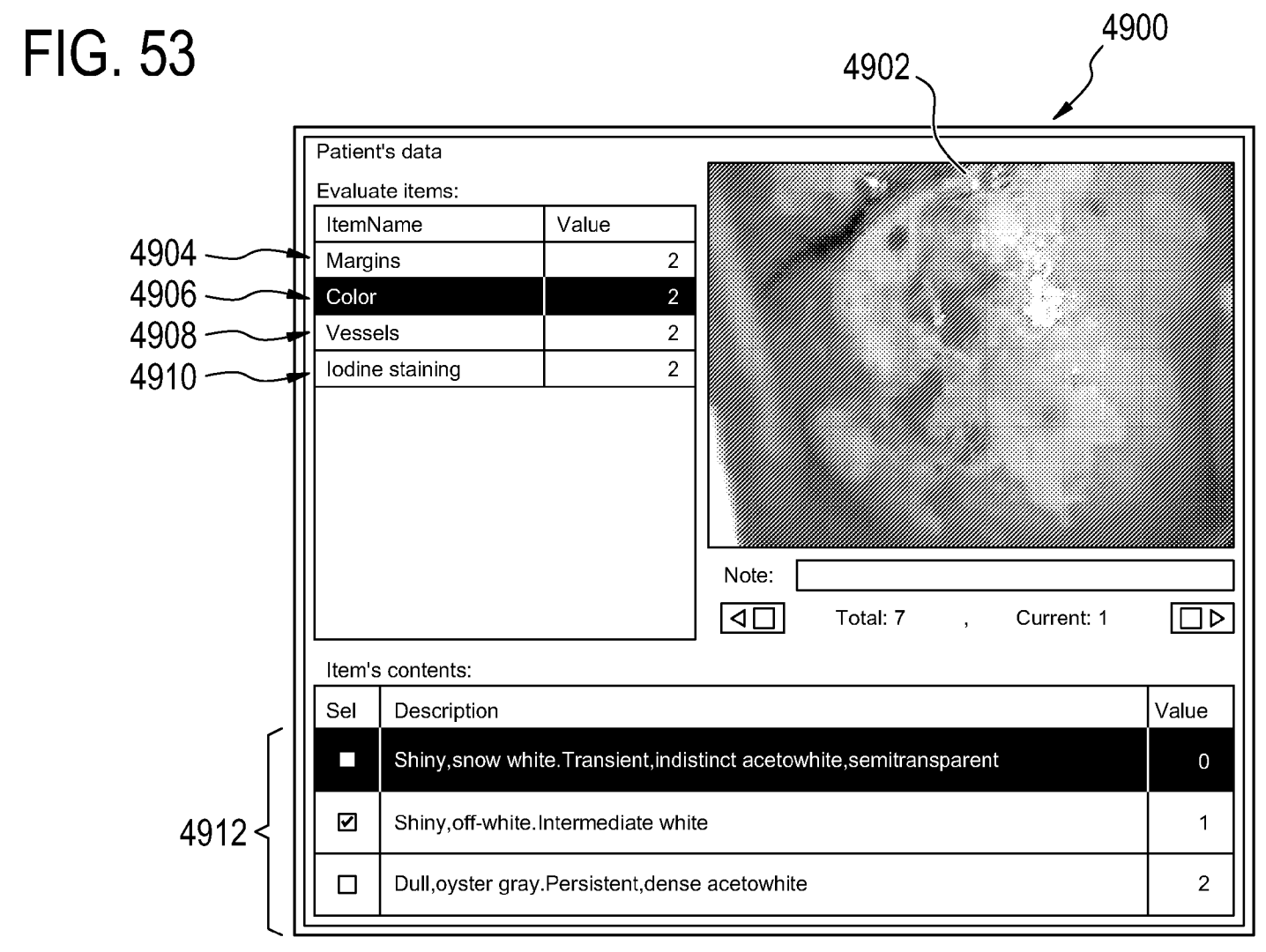

As shown in FIG. 53 subclass 1 is given a score of 0, subclass 2 is given a score of 1 and subclass 3 is given a score of 2. FIG. 53 shows another view of the user interface 4900. In this case the acetowhite kinetic score 4906 has been selected. In this case the score adjustment selector 4912 allows the user to select the acetowhite cervical images snow white, shiny off white, or dense white.

The identification of vessels represented by mosaics, punctations and atypical vessels is discussed next. Based on the coarseness or fineness of these punctations and mosaic patterns, the vessels findings are divided into three subclasses. A score of 0 is provided if the punctations and mosaics are fine. If the punctations and mosaics are coarse then a score of 2 is given. Absence of surface vessels is given a score of 1. Atypical vessels can be detected by color based filtering followed by line based detection. The following Figures show examples of fine/coarse mosaics and patterns and how they are given a score.

Diverse appearances of mosaic patterns can be observed and which can be given different tags like:
tiled and uniform structured,
coarse mosaic,
fine mosaic,
early mosaic partially visible and irregular structure,
bulged mosaic causing specular reflection,
weak mosaic not clearly visible,
mosaic interspersed with atypical/normal vessels,
mosaic interspersed with punctation, and
mosaic in areas near blood or columnar epithelium.

A robust learning based approach may be used to identify these patterns, which carries the inherent ability to deal with multiple variations like scale, uniformity, coarseness, specularity and noise in the appearance of mosaic patterns. Embodiments of the invention may also have the ability to distinguish with most resembling patterns and eventually detect true mosaic regions.

Feature Selection may be performed by object segmentation in order to address such an intra-class variation. A multi-stage classification approach based on co-occurrence of histogram of gradient features followed after fractal based features may be used. This may be a beneficial approach, because the robust discrimination of objects with different shapes. These are one of the most successful features in object detection especially to detect objects with different shapes and orientations. The whole framework is built upon random forests which have gained popularity in recent years in pattern recognition community.

A trained pattern recognition engine or program may be used for mosaic detection and classification. As mentioned previously with respect to punctation detection, the first step for training a learning engine is the training data creation. This is done in a supervised way with successive improvement of classifier by selecting samples on which it fails. Around fifty cases were used for training purpose with totaling of around 10,000 training samples. Each sample is a color image patch taken around in the neighborhood of the point selected for training with window size of 60×60. All these samples are stored and will be used for feature computation.

Next feature computation is discussed. As mentioned previously, two types of features are used, first is the co-occurrence of histogram of oriented gradients (cohog), which is computed over all the samples obtained in training stage. These are mixed with a simple 60×1 color histogram (Each channel 20 bins, three color channels) features to make it robust with respect to lighting variation. The second set of features are fractal which helps in extracting natural geometry of objects like lines, circles and self-similarity. It has been used for classifying breast ultrasound images.

A multi-stage random forest has been used to achieve the robustness and sensitivity. The system consists of two stages. First stage is based on fractal based features and second stage is based on cohog features.

The testing accuracy with fractal features is 84% using a randomly selected testing set selected from 6% of 10,000 test samples. A second classifier with cohog features achieved 86% testing accuracy also using a randomly selected testing set selected from 6% of 10,000 test samples. As a practice, the training and testing sets are kept separate and excluded.

Figure 54:
FIG. 54 shows an example of a cervical image.
Figure 55:
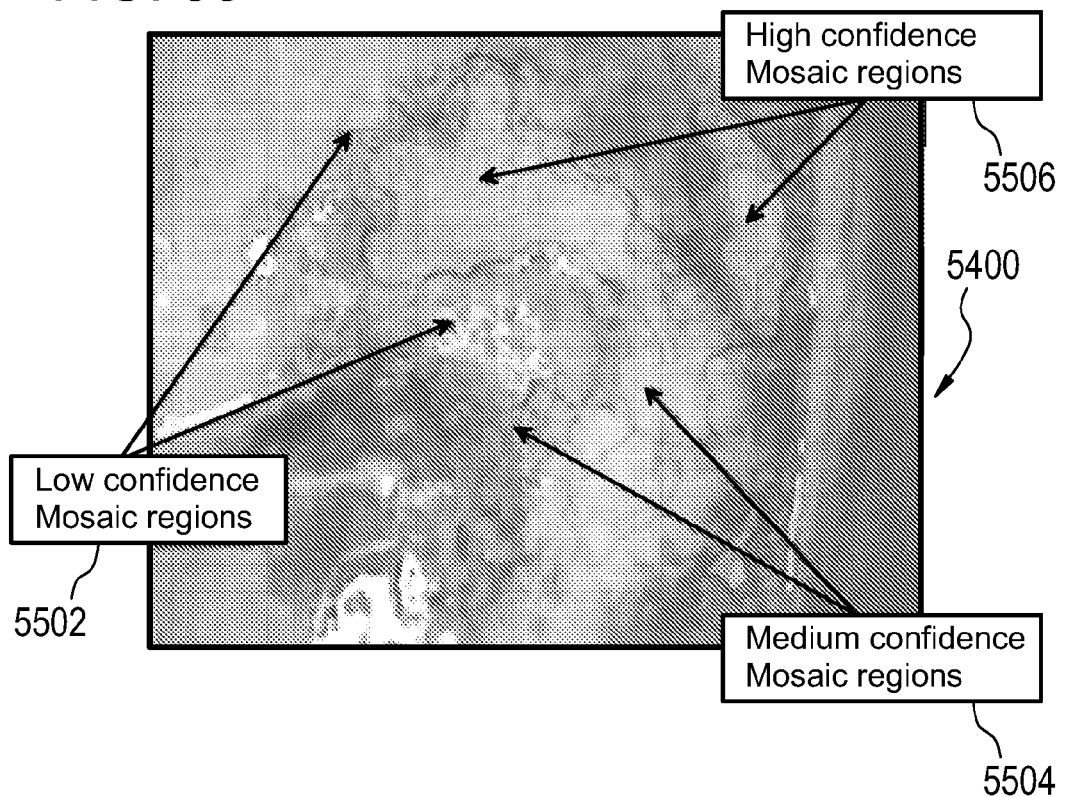
FIG. 55 shows the same cervical image shown in FIG. 54 with mosaic regions indicated.

FIG. 54 shows an example of a cervical image 5400. FIG. 55 shows the same cervical image 5400 with mosaic regions 5502, 5504, 5506 indicated. Region 5502 indicates a region where there is low confidence that there is a mosaic present. Region 5504 indicates regions where there is medium confidence that there are mosaics present. Regions 5506 indicate regions where there is a high confidence that there is a mosaic region present.

Figure 56:
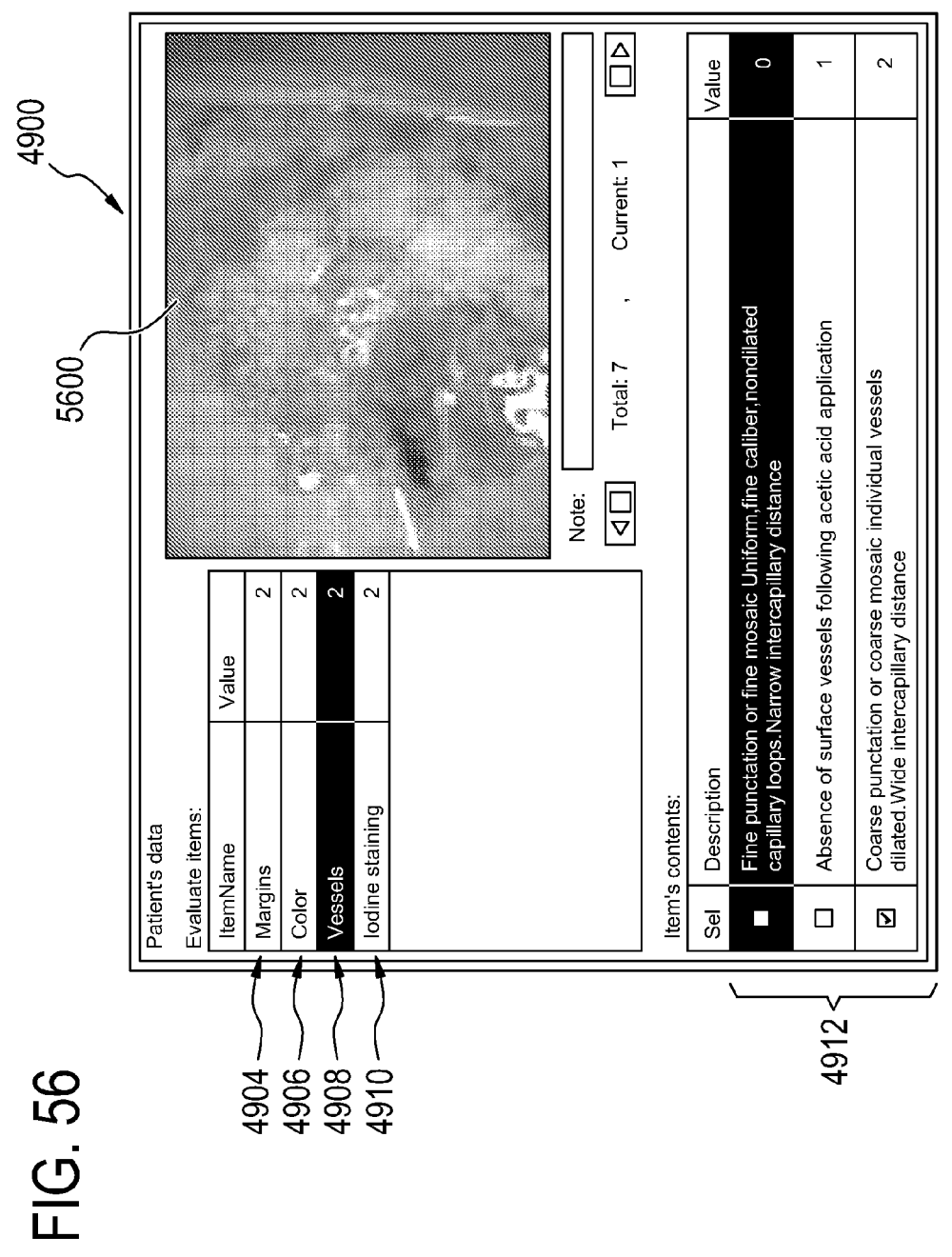

FIG. 56 illustrates the user interface 4900 again. In FIG. 56 the cervical image 5600 shows fine mosaic patterns on the cervix.

Figure 57:
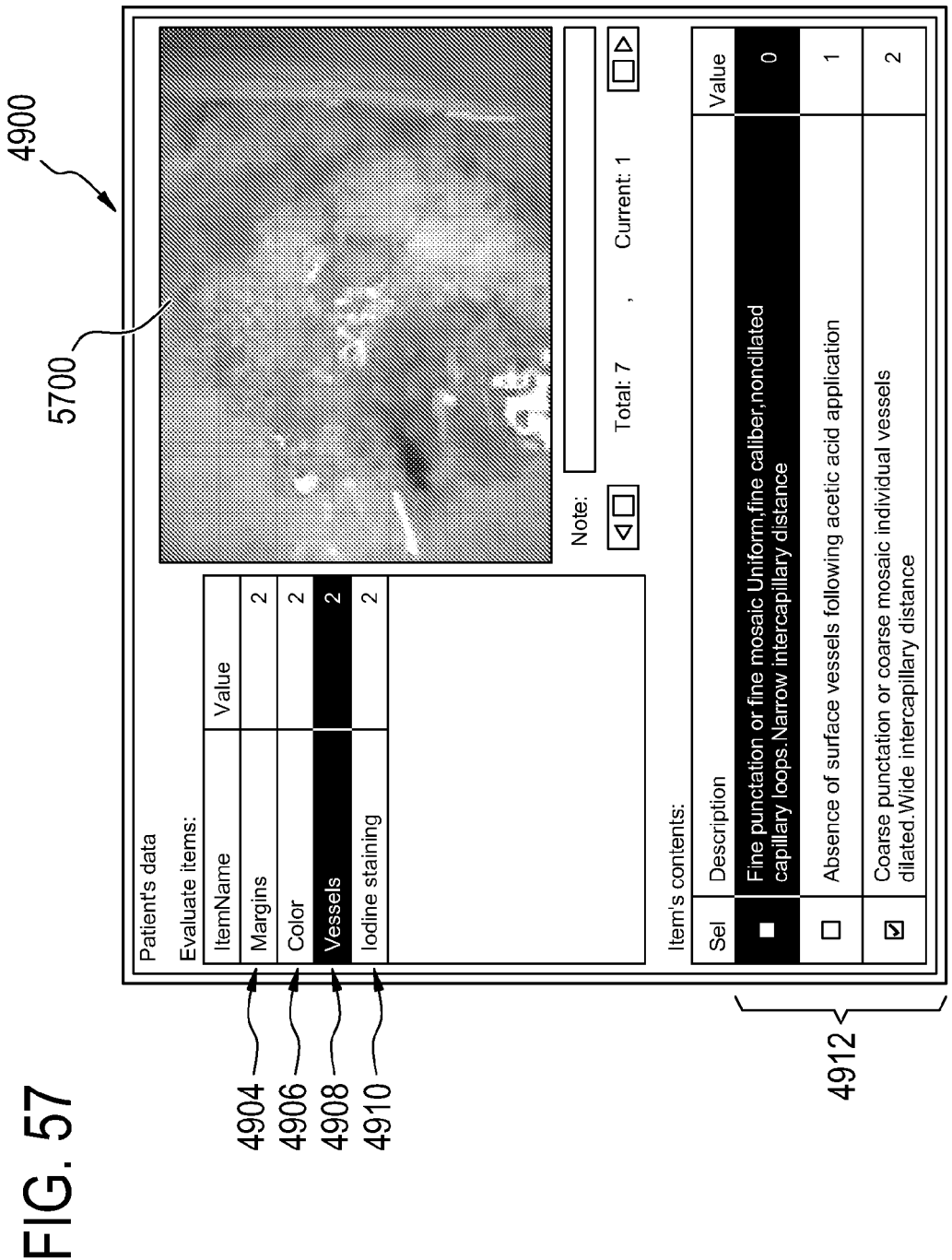
FIG. 57 illustrates a different view of the user interface shown in FIG. 49.

FIG. 57 illustrates the user interface 4900 again. In this example the cervical image 5700 shows course mosaic patterns on the cervix.

Figure 58:
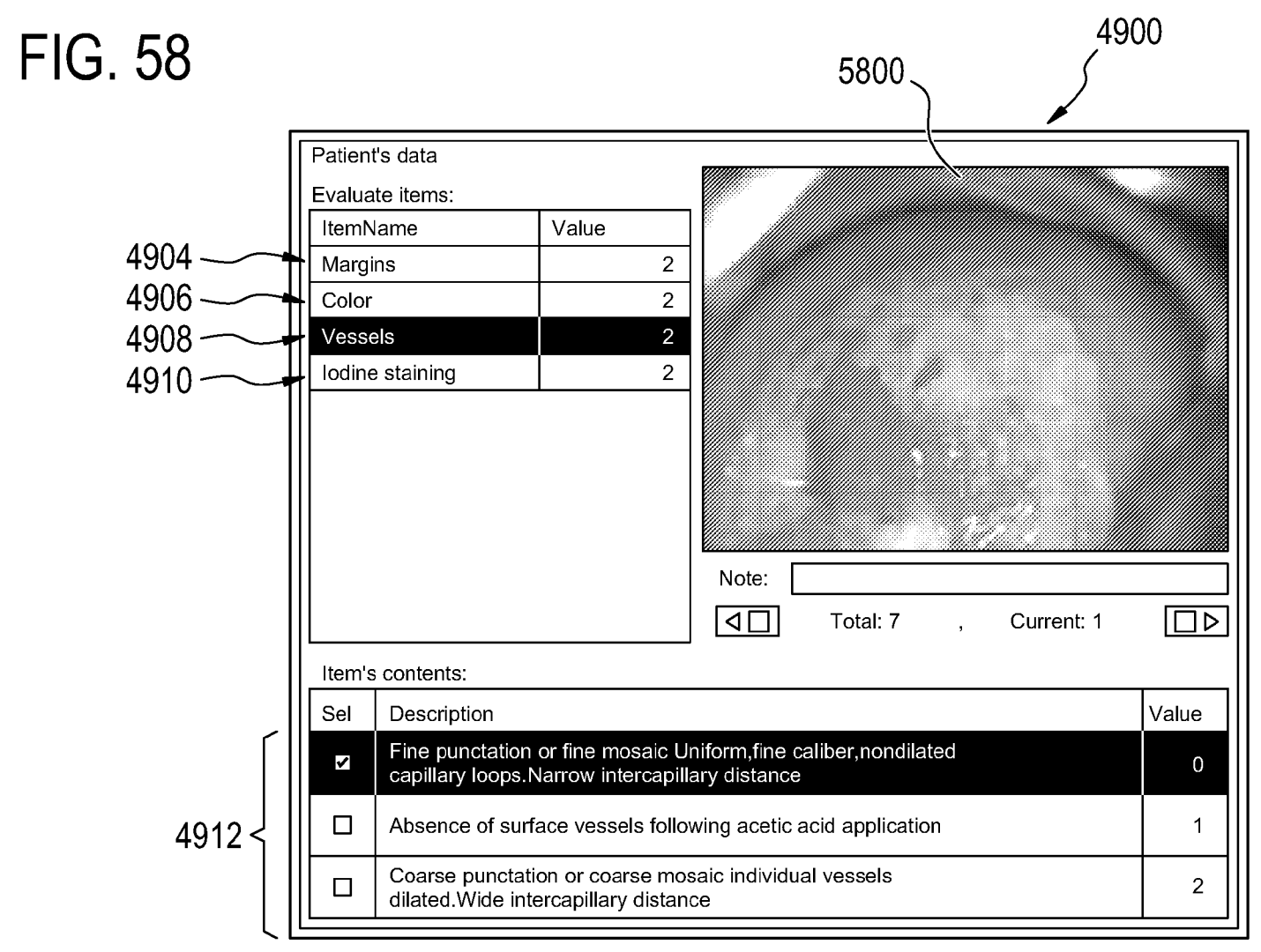

FIG. 58 illustrates the user interface 4900 again. In this example the cervical image 5800 shows fine punctation marks on the cervix.

Figure 59:
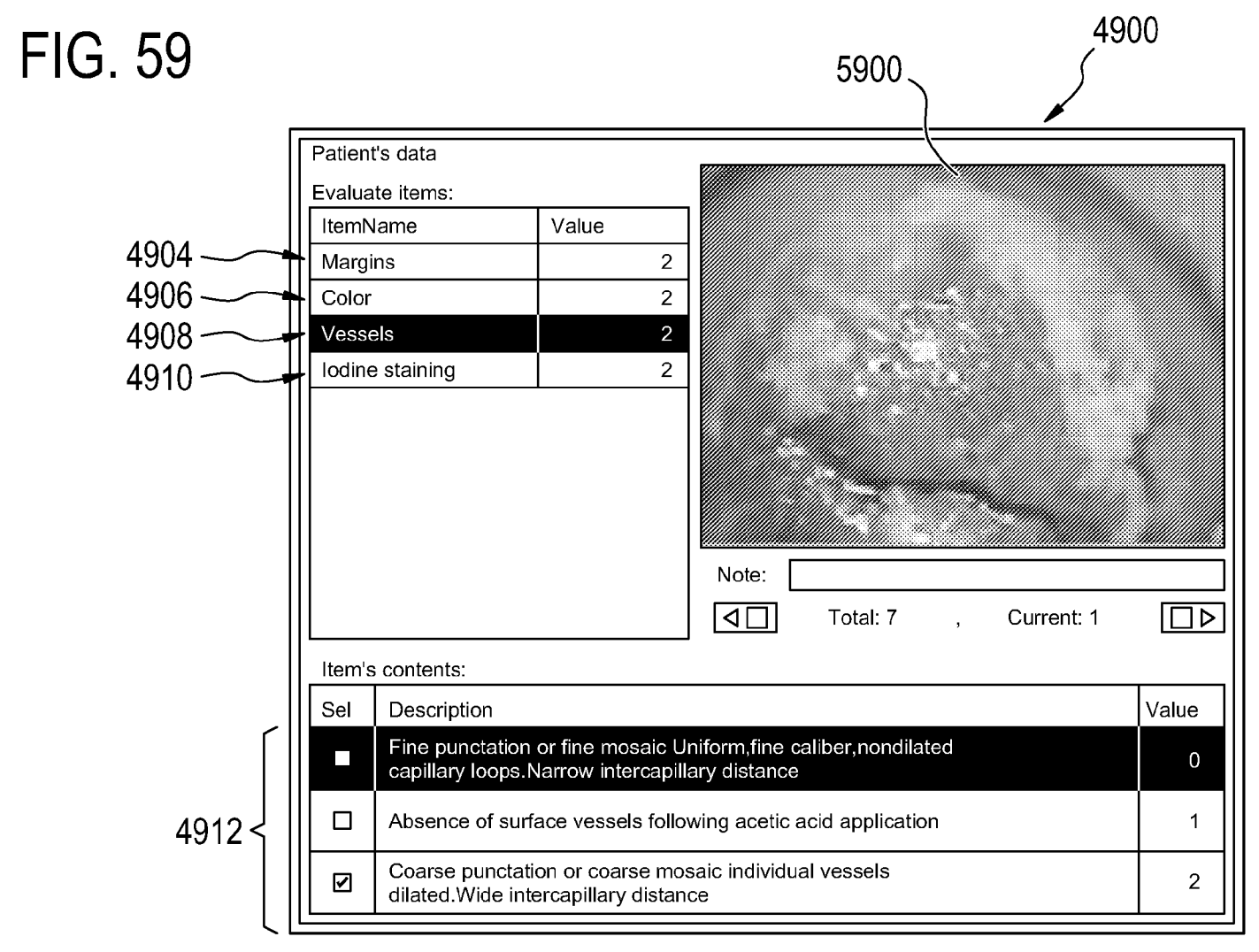

FIG. 59 again illustrates the user interface 4900. In this example the cervical image 5900 shows a cervix with course punctation marks.

Figure 60:
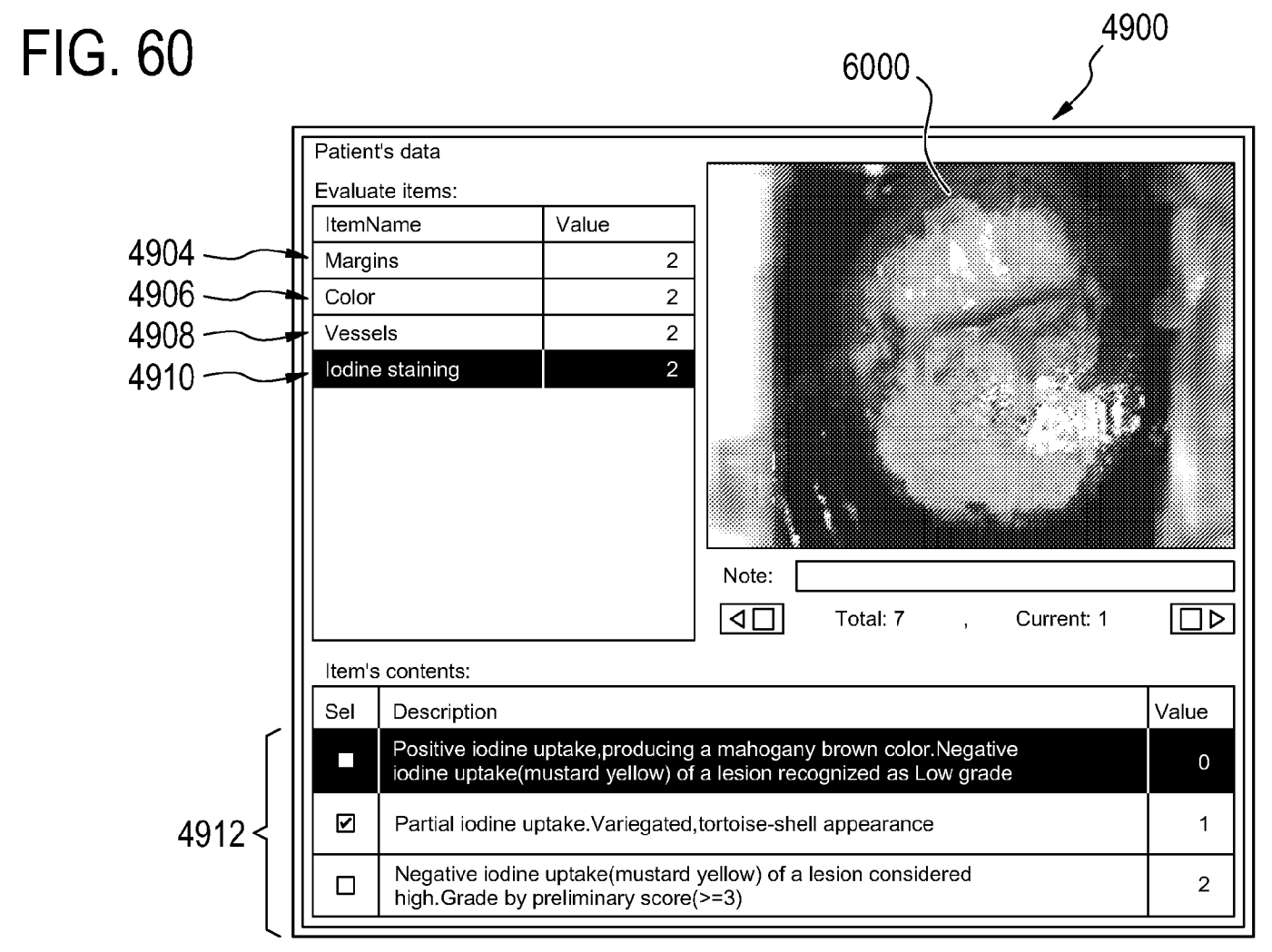
Figures 61, 62:
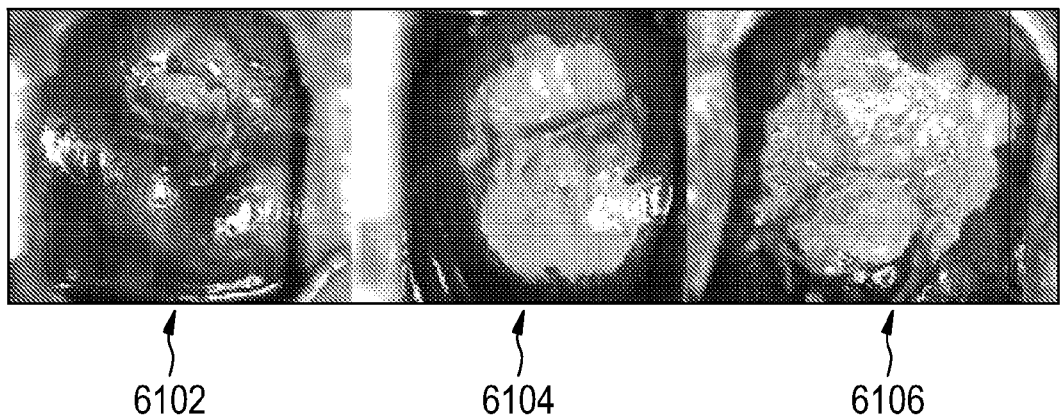
FIG. 61 shows iodine cervical images illustrating positive iodine uptake, shows partial iodine uptake, and negative iodine uptake 6106.
FIG. 62 shows a table which illustrates scoring based on the Reid colposcopic index.

Iodine staining: Iodine staining is broadly subclassified into 3 types as shown in FIGS. 60 and 61. FIG. 60 illustrates the user interface 4900 again. In this example the cervical image is an iodine cervical image 6000.

FIG. 61 illustrates three iodine cervical images 6102, 6104, 6106. Image 6102 shows positive iodine uptake. Image 6104 shows partial iodine uptake. Image three shows negative iodine uptake 6106. Image 6102 corresponds to a first sub-class, image 6104 corresponds to a second sub-class and image 6106 corresponds to a third sub-class.

In order to automatically determine the iodine changes, the iodine negative (yellow) and positive regions (deep brown) are separated using Otsu thresholding. A histogram based approach is used to classify if a region is iodine negative or iodine positive. This is followed by identifying if the iodine negative area lies within the transformation zone or not. If there is positive iodine uptake in the transformation zone then a score of zero is given. If there are both yellow and brown regions in the transformation zone then a score of one is given. If an acetowhite region shows yellow color then a score of two is given.

Once all the four clinical findings are given a score, they are summed up to give a final/overall score to the colposcopic examination/recording.

FIG. 62 shows a table with scores 6200 on the Reid colposcopic index. The score 6200 can be determined by summing the values of the acetowhite kinetic score, the acetowhite margin score, the vascular pattern score and the iodine staining score. Depending upon the score there is a corresponding histology 6202 which is a likely diagnosis. With a score of 0-2 the histology is likely to be CIN1. In this case the lesion may be pre-cancerous. If the score is between 3 and 4 there may be an overlapping lesion and the cancer is likely to be CIN1 or CIN2. In this case the patient may want to follow up with further examinations. If the score is 5-8 the histology is likely to be CIN2 or 3 and likely the patient or subject needs treatment.

Various colposcopy indices are used clinically and Colposcopists have a preference for using any one of them. To name a few: Reid's, modified Reid, Simplified Reid, Swede score etc. In some embodiments essential anatomical features may be detected automatically so that the user may be able to select for any of the indexing methods used clinically.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

LIST OF REFERENCE NUMERALS 1 cervix
2 transformation zone
3 columnar epithelium
4 Os
1000 medical instrument
1002 optical examination system
1004 computer
1006 processor
1008 hardware interface
1010 user interface
1012 computer storage
1014 computer memory
1016 cervical image
1018 set of interest points
1020 filtered set of interest points
1022 reduced set of interest points
1024 classified set of interest points
1026 set of punctation locations
1028 punctation mark regions
1030 control module
1032 digital filter
1034 morphological filter
1036 neighborhood based filter
1038 trained classification module
1040 second neighborhood based filter
1100 cervical image
1102 region with easily located punctation points
1104 first region
1106 second region
1108 zoom of first region
1110 punctation region
1112 zoom of second region
1114 punctation region
1116 image 1100 with punctation points emphasized
1600 number of trees
1602 punctation sample test error
1700 cervical image
1702 regions with punctation
1800 image 1700 after preprocessing
1900 image 1700 showing detected interest points
2000 image 1900 after morphological filtering
2100 image 2000 after neighborhood filtering
2200 image 2100 after using RT classifier
2202 region of interest
2204 zoom of region of interest
2300 image 2200 after using second neighborhood filtering
2302 region of interest
2304 zoom of region of interest
2400 cervical image
2402 region of interest
2404 zoomed image of region 2402
2406 image 2400 with punctation locations
2408 image 2400 with punctation regions
2500 cervical image
2502 region of interest
2504 zoomed image of region 2502
2506 image 2500 with punctation locations
2508 image 2500 with punctation regions
2600 cervical image
2602 region of interest
2604 zoomed image of region 2602
2606 image 2600 with punctation locations
2608 image 2600 with punctation regions
2700 cervical image
2702 region of interest
2704 zoomed image of region 2702
2706 image 2700 with punctation locations
2708 image 2700 with punctation regions
2800 cervical image
2802 image 2800 with punctation locations
2804 image 2800 with punctation regions
2900 cervical image
2902 image 2900 with punctation locations
2904 image 2900 with punctation regions
3100 medical instrument
3102 video data
3104 set of transformations
3105 cumulative transformation
3106 first image
3108 second image
3109 registration of first and second image
3110 image transformation module
3112 cumulative transformation calculation module
3114 image registration module
3300 image
3302 image
3304 box
3500 medical instrument
3502 saline cervical image 3504 acetowhite cervical images
3506 iodine cervical image
3508 acetowhite kinetic score
3510 acetowhite margin score
3512 vascular pattern score
3514 iodine staining score
3516 colposcopy index score
3520 acetowhite kinetic score calculation module
3522 acetowhite margin score calculation module
3524 vascular pattern score calculation module
3526 iodine staining score calculation module
3528 colposcopy index score calculation module
3800 acetowhite cervical image
3802 cervical region
3900 iodine cervical image
3902 cervical region
4000 histogram
4002 histogram
4100 iodine cervical image
4102 acetic acid cervical image
4104 cervical region
4106 old SCJ region
4202 new SCJ region
4302 Os
4400 user interface
4402 cervical image
4404 colposcopic findings
4406 diagnosis
4500 saline cervical image
4502 acetowhite cervical image
4504 opacity image
4506 saline cervical image
4508 acetowhite cervical image
4510 opacity image
4600 acetowhite cervical image
4602 acetowhite cervical image
4604 acetowhite cervical image
4606 punctation marks
4608 punctation regions
4700 acetowhite cervical image
4702 acetowhite cervical image
4704 acetowhite cervical image
4706 mosaic regions
4708 highlighted mosaic regions
4800 cervical image
4802 cervical image
4804 candidate white gland
4808 white gland
4900 user interface
4902 cervical image
4904 acetowhite margin score
4906 acetowhite kinetic score
4908 vascular pattern score
4910 iodine staining score
4912 score adjustment selector
5002 condylomatous cervical image
5004 sharp margins cervical image
5006 rolled margins cervical image
5102 snow white cervical image
5104 shiny off white cervical image
5106 dense white cervical image
5200 time
5202 opacity index
5204 subclass 1
5206 subclass 2
5208 subclass 3
5400 cervical image
5502 low confidence mosaic region
5504 medium confidence mosaic region
5506 high confidence mosaic region
5600 cervical image showing fine mosaics
5700 cervical image showing coarse mosaics
5800 cervical image showing fine punctation
5900 cervical image showing coarse punctation
6000 iodine cervical image
6102 positive iodine uptake in iodine cervical image
6104 positive iodine uptake in iodine cervical image
6106 positive iodine uptake in iodine cervical image
6200 score
6202 histology

The invention claimed is:

1. A medical instrument comprising:
an optical examination system for acquiring a cervical image;
a processor for controlling the medical instrument;
a memory containing machine executable instructions for execution by the processor, wherein execution of the instructions causes the processor to:
acquire the cervical image using the optical examination system;
calculate a set of interest point locations using a digital filter;
calculate a filtered set of interest point locations using the set of interest point locations and a morphological filter;
calculate a reduced set of interest points locations using the filtered set of interest point locations and a neighborhood based filter;
calculate a classified set of interest point locations reduced set of interest points and a trained classification module;
calculate a set of punctation locations using the classified set of interest point locations and a second neighborhood based filter;
calculate punctation mark regions using the punctation point locations; and
outputting the punctation mark regions;
wherein execution of the instructions further causes the processor to:
acquire a second cervical image using the optical examination system;
calculate a second set of interest point locations using the digital filter;
calculate a second filtered set of interest point locations using the second set of interest point locations and the morphological filter;
calculate a second reduced set of interest points locations using the second filtered set of interest point locations and the neighborhood based filter;
calculate a second classified set of interest point locations using the trained classification module and the second reduced set of interest points; and
calculate a second set of punctation locations using the second neighborhood based filter and the second classified set of interest point locations, wherein the punctation mark regions using the punctation point locations and the second punctation point locations;
register the cervical image and the second cervical image using an image registration module;
acquire the first cervical image and the second cervical image by acquiring video data comprising multiple image frames;
select the first cervical image and the second cervical image from the multiple image frames;

receive the video data comprising multiple image frames;

determine a transformation model between each pair of consecutive image frames selected from the multiple image frames;

calculate a cumulative transformation model from the transformation model between each pair of consecutive image frames;

register each of the multiple image frames using the cumulative transformation model; and provide the registration of the first cervical image and the second cervical image using the cumulative transformation model.

2. The medical instrument of claim 1, wherein the cervical image is a saline cervical image, wherein execution of the instructions further causes the processor to:

acquire multiple acetowhite cervical images using the optical examination system;

acquire an iodine cervical image using the optical examination system;

calculate an acetowhite kinetic score using the acetowhite cervical images;

calculate an acetowhite margin score using the acetowhite cervical images;

calculate a vascular pattern score using the acetowhite cervical images and the saline cervical image;

calculate an iodine staining score using the iodine cervical image; and determining a colposcopy index score by summing the acetowhite kinetic score, the acetowhite margin score, the vascular pattern score, and the iodine staining score.

3. The medical instrument of claim 2, wherein the medical instrument further comprises a display and a use interface.

4. The medical instrument of claim 3, wherein execution of the instructions further causes the processor to:

display at least one of the acetowhite cervical images on the display;

display the acetowhite kinetic score on the display; and receive a corrected acetowhite kinetic score from the user interface, wherein the colposcopy index score is at least partially determined using the corrected acetowhite kinetic score.

5. The medical instrument, of claim 3, wherein execution of the instructions further causes the processor to:

display at least one of the acetowhite cervical images on the display;

display the acetowhite margin score on the display; and receive a corrected acetowhite margin score from the user interface, wherein the colposcopy index score is at least partially determined using the corrected acetowhite margin score.

6. The medical instrument of claim 3, wherein execution of the instructions further causes the processor to:

display at least one of the acetowhite cervical images on the display;

display the vascular pattern score on the display; and receive a corrected vascular pattern score from the user interface, wherein the colposcopy index score is at least partially determined using the corrected vascular pattern score.

7. The medical instrument of claim 3, wherein execution of the instructions further causes the processor to:

identify mosaics, the punctation mark regions, and/or atypical vessels in the saline cervical image; and identify post acetic acid mosaics, post acetic acid punctation mark regions, and/or post acetic acid atypical vessels in an acetowhite cervical image selected from the acetowhite cervical images, wherein the vascular pattern score is calculated using the difference between any one of the following: the mosaics and the post acetic acid mosaics; the punctation mark regions and the post acetic acid punctation mark regions; and the atypical vessels and the post acetic acid atypical vessels; and combinations thereof.

8. The medical instrument of claim 1, wherein the cervical image is any one of the following: a first pre-acetic acid image, a first green filter image, and a first post-acetic acid image; and wherein the second cervical image is any one of the following: a second pre-acetic acid image, a second green filter image, and a second post-acetic acid image.

9. The medical instrument, of claim 1, wherein execution of the instructions further causes the processor to:

detect a failure of determining a transformation model between the at least one pair of consecutive image frames;

calculate a first image segmentation from a first image frame selected from the video data before the failure;

calculate a second image segmentation from a second image frame selected from the video data after the failure;

determine a second transformation between the first image frame and the second image frame;

correct the cumulative transformation model using the second transformation.

10. The medical instrument of claim 1, wherein execution of the instructions further cause the processor to:

detect a failure of determining a transformation between the at least one pair of consecutive image frames;

choose a first image frame from the video data before the failure;

choose a second image frame from the video data after the failure; and determine a second transformation between the first image and the second image; and correct the cumulative transformation model using the second transformation.

11. The medical instrument of claim 1, wherein the first cervical image is a pre-contrast and/or pre-stimulating agent image, and wherein the second cervical image is a post-contrast and/or post-stimulating agent image, wherein execution of the instructions further causes the processor to:

identify essential anatomical objects in the images, i.e, Os, columnar region, and transformation zone; and generate an opacity difference score.

12. The medical instrument of claim 1, wherein the second cervical image is a zoom image showing a zoomed region at least partially within the first cervical image.

13. The medical instrument of claim 1, wherein execution of the instructions further causes the processor to display the punctation mark regions superimposed on the first cervical image on a display.

14. A computer program product comprising non-transitory machine executable instructions for execution by a processor for controlling a medical instrument, the medical instrument comprises an optical examination system for acquiring a cervical image;

wherein execution of the instructions causes the processor to:

acquire the cervical image using the optical examination system;

calculate a set of interest point locations using a digital filter;

calculate a filtered set of interest, point locations using the set of interest point locations and a morphological filter;

calculate a reduced set of interest points locations using the filtered set of interest point locations and a neighborhood based filter;

calculate a classified set of interest point, locations using the reduced set of interest points and a trained classification module;

calculate a set of punctation locations using the classified set of interest point locations and a second neighborhood based filter; and calculate punctation mark regions using the punctation point locations;

wherein execution of the instructions further causes the processor to:

acquire a second cervical image using the optical examination system;

calculate a second set of interest point locations using the digital filter;

calculate a second filtered set of interest point locations using the second set of interest point locations and the morphological filter;

calculate a second reduced set of interest points locations using the second filtered set of interest point locations and the neighborhood based filter;

calculate a second classified set of interest point locations using the trained classification module and the second reduced set of interest points; and calculate a second set of punctation locations using the second neighborhood based filter and the second classified set of interest point locations, wherein the punctation mark regions using the punctation point locations and the second punctation point locations;

register the cervical image and the second cervical image using an image registration module;

acquire the first cervical image and the second cervical image by acquiring video data comprising multiple image frames;

select the first cervical image and the second cervical image from the multiple image;

receive the video data comprising multiple image frames;

determine a transformation model between each pair of consecutive image frames selected from the multiple image frames;

calculate a cumulative transformation model from the transformation model between each pair of consecutive image frames;

register each of the multiple image frames using the cumulative transformation model; and provide the registration of the first cervical image and the second cervical image using the cumulative transformation model.

15. A method of operating a medical instrument, the medical instrument comprises an optical examination system for acquiring a cervical image;

wherein the method comprises the steps of:

acquiring the cervical image using the optical examination system;

calculating a set of interest point locations using a digital filter;

calculating a filtered set of interest point locations using the set of interest point locations and a morphological filter;

calculating a reduced set of interest points locations using the filtered set of interest point locations and a neighborhood based filter;

calculating a classified set of interest point, locations using the reduced set of interest points and a trained classification module;

calculating a set of punctation locations using the classified set of interest point locations and a second neighborhood based filter; and calculating punctation mark regions using the punctation point locations;

wherein execution of the instructions further causes the processor to:

acquiring a second cervical image using the optical examination system;

calculating a second set of interest point locations using the digital filter;

calculating a second filtered set of interest, point locations using the second set of interest point locations and the morphological filter;

calculating a second reduced set of interest, points locations using the second filtered set of interest point locations and the neighborhood based filter;

calculating a second classified set of interest point locations using the trained classification module and the second reduced set of interest points; and calculating a second set of punctation locations using the second neighborhood based filter and the second classified set of interest point locations, wherein the punctation mark regions using the punctation point locations and the second punctation point locations;

registering the cervical image and the second cervical image using an image registration module;

acquiring the first cervical image and the second cervical image by acquiring video data comprising multiple image frames;

selecting the first cervical image and the second cervical image from the multiple image frames;

receiving the video data comprising multiple image frames;

determining a transformation model between each pair of consecutive image frames selected from the multiple image frames;

calculating a cumulative transformation model from the transformation model between each pair of consecutive image frames;

registering each of the multiple image frames using the cumulative transformation model; and providing the registration of the first cervical image and the second cervical image using the cumulative transformation model.

* * * * *